United States Patent [19]

Shiokari et al.

[11] Patent Number: 4,757,066

[45] Date of Patent: Jul. 12, 1988

[54] COMPOSITION CONTAINING A PENEM OR CARBAPENEM ANTIBIOTIC AND THE USE OF THE SAME

[75] Inventors: Takashi Shiokari; Seigo Ueda; Masayuki Iwata; Yukinori Kawahara, all of Tokyo, Japan

[73] Assignee: Sankyo Company Limited, Tokyo, Japan

[21] Appl. No.: 917,793

[22] Filed: Oct. 10, 1986

[30] Foreign Application Priority Data

| Oct. 15, 1984 [JP] | Japan | 59-215683 |
| Jan. 28, 1985 [JP] | Japan | 60-14001 |
| Oct. 24, 1985 [JP] | Japan | 60-238283 |
| Apr. 10, 1986 [JP] | Japan | 61-81218 |

[51] Int. Cl.$^4$ ............................................. A61K 31/40
[52] U.S. Cl. ...................................... 514/210; 424/85; 540/350
[58] Field of Search ..................... 514/210; 540/350; 424/85

[56] References Cited

U.S. PATENT DOCUMENTS

| 4,427,690 | 1/1984 | Cole et al. | 514/210 |
| 4,536,335 | 8/1985 | Kim et al. | 540/350 |
| 4,543,257 | 9/1985 | Cama et al. | 540/350 |
| 4,552,873 | 11/1985 | Miyadera et al. | 514/210 |
| 4,576,939 | 3/1986 | Ross et al. | 514/210 |

OTHER PUBLICATIONS

Cecil Textbook of Medicine, 16th Edition, editor Wyngaarden et al., W. B. Saunders Company, Philadelphia, Pa., 1970, pp. 62–65.
Kagan, Antimicrobial Therapy, W. B. Saunders Company, Philadelphia, Pa., 1970, pp. 68–70 and 170–173.

*Primary Examiner*—Ronald W. Griffin
*Attorney, Agent, or Firm*—Frishauf, Holtz, Goodman & Woodward

[57] ABSTRACT

Administration of an N-acylated amino acid in association with a penem or carbapenem antibiotic relieves or eliminates the renal problems associated with administration of the antibiotic alone. The amino acid derivative and antibiotic may be formulated together as a composition or administered separately, either simultaneously or sequentially.

116 Claims, No Drawings

COMPOSITION CONTAINING A PENEM OR CARBAPENEM ANTIBIOTIC AND THE USE OF THE SAME

CROSS-REFERENCE TO RELATED APPLICATION

This is a continuation-in-part of U.S. patent application Ser. No. 787,609 filed Oct. 15, 1985, now abandoned.

BACKGROUND OF THE INVENTION

The present invention relates to a novel composition comprising a penem or carbapenem antibiotic in association with an amino acid derivative. The invention also provides a method of treating bacterial infections by administering to the patient, simultaneously or sequentially, a penem or carbapenem antibiotic and at least one amino acid derivative selected from a class of acylated amino acids.

The class of compounds known as "penem and carbapenem antibiotics" is, of course, very well known and is potentially of great value for the treatment of bacterial infections. Although, as a group, these penem and carbapenem antibiotics exhibit excellent anti-bacterial activity and a variety of other properties which render them highly suitable for pharmaceutical use, they do have a number of disadvantages. One of the problems of these antibiotics is that, in general, they exhibit a degree of renal toxicity, and some degree of kidney damage is a frequent side effect of their use; accordingly, such penem and carbapenem antibiotics should not be used for the treatment of patients with actual or suspected impaired renal function. As a result, the penem and carbapenem antibiotics cannot be used for many patients for whom otherwise they would be the antibiotic of choice. The problem of renal toxicity is particularly acute when the antibiotics are administered by intravenous or intramuscular injection in a high dose.

We have now surprisingly discovered that the concurrent, or effectively concurrent, administration, with the penem or carbapenem antibiotic, of one or more of a certain class of acylated amino acid derivatives significantly reduces this renal toxicity.

EP Publication No. 7614 discloses the use of a dipeptidase inhibitor in association with antibiotics similar to those to which the present invention relates. However, the dipeptidase inhibitors employed are structurally different from the amino acid derivatives of the present invention and are employed for a totally different purpose. The amino acid derivatives employed in the present invention possess little or no dipeptidase inhibitory activity.

BRIEF SUMMARY OF INVENTION

It is, therefore, an object of the present invention to provide a composition comprising a penem or carbapenem antibiotic having lower renal toxicity than does the antibiotic on its own.

It is a further object of the invention to provide a method of treating a bacterial infection in a mammal by administering to said mammal, simultaneously or sequentially, a penem or carbapenem antibiotic and an acylated amino acid derivative.

Accordingly, in one aspect, the present invention provides a composition comprising:

(a) an antibiotic selected from the group consisting of penem antibiotics and carbapenem antibiotics; and (b) a pharmaceutically acceptable N-acylated derivative of an amino acid wherein the amino group and the carboxylic acid group are attached to a saturated aliphatic carbon chain or carbon atom, or a salt thereof.

In another aspect, the invention provides a method of treating a mammal suffering from a bacterial infection by administering to said mammal:

(a) an antibiotic selected from the group consisting of penem antibiotics and carbapenem antibiotics; and (b) a pharmaceutically acceptable N-acylated derivative as defined above.

DETAILED DESCRIPTION OF INVENTION

There is no particular limitation on the nature of the penem or carbapenem antibiotic to which the present invention can be applied and it is believed that the beneficial effects of the concurrent administration of an N-acylated amino acid derivative will be achieved regardless of the particular antibiotic chosen. However, the penem and carbapenem antibiotics which are currently of most actual or potential interest may be represented by the general formula (I):

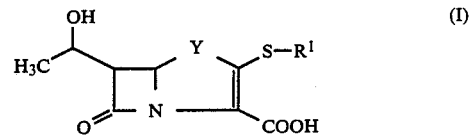

in which:

Y represents a sulfur atom, a methylene group or a methylene group having 1 or 2 substituents selected from the group consisting of methyl and methoxy groups; and $R^1$ represents a $C_1$–$C_6$ alkyl group, a $C_1$–$C_6$ alkyl group having at least one substituent selected from the group consisting of substituents (i) or a heterocyclic group having from 4 to 14 ring atoms of which from 1 to 5 are hetero-atoms selected from the group consisting of nitrogen, oxygen and sulfur atoms where said heterocyclic group is unsubstituted or has at least one substituent selected from the group consisting of substituents (ii):

substituents (i):

halogen atoms, amino groups, amino groups having at least one substituent selected from the group consisting of substituents (iii), $C_1$–$C_4$ alkylideneamino groups, $C_1$–$C_4$ aminoalkylideneamino groups, amidino groups, amidino groups having from 1 to 3 substituents selected from the group consisting of substituents (iii), heterocyclic groups having from 4 to 14 ring atoms of which from 1 to 5 are hetero-atoms selected from the group consisting of nitrogen, oxygen and sulfur hetero-atoms wherein said heterocyclic group is unsubstituted or has at least one substituent selected from the group consisting of substituents (ii), imino groups, cyano groups, carbamoyl groups and carbamoyl groups having at least one substituent selected from the group consisting of $C_1-C_4$ alkyl groups and $C_1-C_4$ alkoxy groups;

substituents (ii):

$C_1-C_6$ alkanimidoyl groups, $C_1-C_6$ alkyl groups, alkoxyalkyl groups where the alkoxy and alkyl parts are each $C_1-C_4$, carbamoyl groups, carbamoyl groups having at least one substituent selected from the group consisting of $C_1-C_4$ alkyl groups and $C_1-C_4$ alkoxy groups. $C_1-C_4$ haloalkyl groups, heterocyclic acylimidoyl groups where the heterocyclic part has from 5 to 9 ring atoms of which from 1 to 3 are heteroatoms selected from the group consisting of nitrogen, oxygen and sulfur hetero-atoms, amidino groups, amidino groups having from 1 to 3 substituents selected from the group consisting of substituents (iii), imino groups, oxygen atoms, $C_1-C_6$ alkanoyl groups, $C_1-C_6$ alkanesulfonyl groups, $C_1-C_6$ alkanesulfinyl groups, hydroximino groups, $C_1-C_4$ alkoximino groups, carbamoyloxy groups, carbamoyloxy groups having at least one substituent selected from the group consisting of $C_1-C_4$ alkyl groups and $C_1-C_4$ alkoxy groups, carbamoyloxyalkyl groups where the alkyl part is $C_1-C_4$ and the carbamoyl part is unsubstituted or has at least one substituent selected from the group consisting of $C_1-C_4$ alkyl groups and $C_1-C_4$ alkoxy groups and $C_1-C_4$ iminoalkyl groups;

substituents (iii):

$C_1-C_6$ alkyl groups, $C_2-C_6$ alkenyl groups, $C_2-C_6$ alkynyl groups, oxygen atoms and said alkyl, alkenyl and alkynyl groups having at least one substituent selected from the group consisting of halogen atoms, carbamoyloxy groups and carbamoyloxy groups having at least one substituent selected from the group consisting of $C_1-C_4$ alkyl groups and $C_1-C_4$ alkoxy groups.

Preferably Y represents a sulfur atom, a methylene group, or the group $CH_3-CH<$, $CH_3O-CH<$ or $(CH_3)_2C<$.

Preferred examples of groups which may be represented by $R^1$ include the ethyl, 2-fluoroethyl, 2-(aminomethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)-$N^1$-methylamidinomethyl, $N^1$-(3-fluoropropyl)-$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidoyl-3-pyrrolidinyl, $N^1,N^1$-diallylamidinomethyl, $N^1$-methyl-$N^1$-(2-propynyl)amidino, $N^1$-(2-fluoroethyl)-$N^1$-methylamidino, $N^1$-(3-fluoropropyl)-$N^1$-methylamidino, $N^1$-methyl-$N^1$-(2,2,2-trifluoroethyl)amidino, $N^1$-allyl-$N^1$-methylamidinomethyl, cyanomethyl, 2-cyanoethyl, 1-cyanoethyl, 2-cyano-1-methylethyl, 2-aminoethyl, 1-carbamoylethyl, 2-(1-aminoethylideneamino)ethyl, 1-amidino-3-pyrrolidinyl, 2-methyl-1,3-diazabicyclo[3.3.0]oct-2-en-7-yl, 2-methoxymethyl-1,3-diazabicyclo[3.3.0]oct-2-en-7-yl, 5-imino-2-pyrrolidinyl, 2-imino-5-piperidinyl, 1-acetimidoyl-5-methylcarbamoyl-3-pyrrolidinyl, 1-acetimidoyl-5-methoxycarbamoyl-3-pyrrolidinyl, 2-imino-2-(S-oxothiomorpholino)ethyl, 2-imino-2-(1,1-dioxo-1,3-thiazolidin-3-yl)ethyl, 2-imino-2-(S,S-dioxothiomorpholino)ethyl, 2-imino-2-(3,5-dioxo-1-piperazinyl)ethyl, 2-imino-2-(4-methyl-3,5-dioxo-1-piperazinyl)ethyl, 2-imino-2-(3-oxo-1-piperazinyl)ethyl, 2-imino-2-(4-methyl-3-oxo-1-piperazinyl)ethyl, 2-imino-2-(4-acetyl-3-oxo-1-piperazinyl)ethyl, 2-imino-2-(4-methanesulfonyl-3-oxo-1-piperazinyl)ethyl, $N^1$-(2-carbamoyloxyethyl)-$N^1$-methylamidinomethyl, 2-(3-hydroximino-1-pyrrolidinyl)-2-iminoethyl, 2-imino-2-(3-methoximino-1-pyrrolidinyl)ethyl, 2-(4-hydroximinopiperidino)-2-iminoethyl, 2-imino-2-(4-methoximinopiperidino)ethyl, 2-(3-carbamoyloxy-1-pyrrolidinyl)-2-iminoethyl, 2-imino-2-(3-oxo-1-piperazinyl)ethyl, 2-(3-carbamoylpiperidino)-2-iminoethyl, 2-(3-carbamoyloxypiperidino)-2-iminoethyl, 2-(2-carbamoyloxy-1-pyrrolidinyl)-2-iminoethyl, 2-(2-carbamoyloxymethyl-1-pyrrolidinyl)-2-iminoethyl, 2-(4-carbamoyloxypiperidino)-2-iminoethyl, 2-(4-formyl-1-piperazinyl)-2-iminoethyl, 2-(4-acetyl-1-piperazinyl)-2-iminoethyl, 1-formyl-3-azetidinyl, 1-iminomethyl-3-azetidinyl, 1-methyl-4-piperidyl, 1-acetimidoyl-4-piperidyl and 1-acetyl-3-pyrrolidinyl groups.

The invention may also be applied to pharmaceutically acceptable salts and esters of such antibiotics, such as are well known in the art.

Specific examples of compounds of formula (I) which may be employed in the present invention are those in which $R^1$ and Y are as defined below:

| Comp. No. | $R^1$ | Y |
|---|---|---|
| 1. | H, $-CH_2CH_2-N=C-NH_2$ | $CH_2$ |
| 2. | $-CH_2-C(=NH)-N(CH_3)_2$ | $CH_2$ |
| 3. | $-CH_2-C(=NH)-N(CH_3)_2$ | $CH_3, H$ (X) |
| 4. | $-CH_2-C(=NCH_3)-N(CH_3)_2$ | $CH_2$ |
| 5. | $-CH_2-C(=NH)-N(CH_3)_2$ | S |
| 6. | (S)-pyrrolidinyl, $N-C(CH_3)=NH$ | $CH_2$ |

| Comp. No. | R¹ | Y |
|---|---|---|
| 7. | pyrrolidine (R), N-C(CH₃)=NH | CH₂ |
| 8. | pyrrolidine (S), N-C(C₂H₅)=NH | CH₂ |
| 9. | tetrahydropyrimidine with CH₂OCH₃ | CH₂ |
| 10. | pyrrolidine (R), N-CH=NH | CH₂ |
| 11. | -CH₂-C(=NH)-N(CH₃)(CH₂CH₂F) | CH₂ |
| 12. | -CH₂-C(=NH)-N(CH₃)(CH₂CF₃) | CH₂ |
| 13. | -CH₂-C(=NH)-N(CH₃)(CH₂C≡CH) | CH₂ |
| 14. | -CH₂-C(=NH)-N(CH₃)(CH₂CH₂CH₂F) | CH₂ |
| 15. | azetidine with CH₃,H substituent, NH | CH₂ |
| 16. | azetidine with CH₃,H substituent, NH | CH₂ |
| 17. | azetidine, N-C(CH₃)=NH, with CH₃,H | CH₂ |
| 18. | -CH₂- tetrahydropyrimidine | CH₂ |
| 19. | -CH(CH₃)- thiazoline (N,S ring) | CH₂ |
| 20. | pyrrolidine (S), N-C(CH₃)=NH | C(CH₃)₂ |
| 21. | pyrrolidine, NH | C(CH₃)₂ |
| 22. | tetrahydropyrimidine with CH₂OCH₃ | C(CH₃)(H) |
| 23. | pyrrolidine (R), N-C(CH₃)=NH | C(CH₃)(H) |
| 24. | pyrrolidine (S), N-C(CH₃)=NH | C(CH₃)(H) |
| 25. | pyrrolidine (S), NH | C(CH₃)(H) |
| 26. | pyrrolidine (S), N-C(=NH)-pyridyl | CH₂ |
| 27. | pyrrolidine (S), N-C(CH₃)=NH | C(CH₃)(H) |
| 28. | pyrrolidine (S,S), N-C(CH₃)=NH, CONH₂ | CH₂ |
| 29. | tetrahydropyrimidine with CH₂Cl | CH₂ |
| 30. | pyrrolidine (S), N-C(=NH)(n-C₃H₇) | CH₂ |
| 31. | -CH₂-C(=NH)-N(allyl)₂ | CH₂ |

| Comp. No. | R¹ | Y |
|---|---|---|
| 32. | -CH₂-C(=NH)-N(CH₃)(CH₂CH₂F) | CH₃ ▲ H (wedge/dash) |
| 33. | -CH₂-C(=NH)-N(CH₃)(allyl) | CH₃ ▲ H |
| 34. | -CH₂-C(=NH)-N(CH₃)(CH₂CH₂CH₂F) | CH₃ ▲ H |
| 35. | -CH₂-C(=NH)-N(allyl)₂ | CH₃ ▲ H |
| 36. | -CH₂CH₃ | S |
| 37. | -CH₂CH₂F | S |
| 38. | pyrrolidin-3-yl (NH) | S |
| 39. | -CH₂CN | S |
| 40. | -CH(CH₃)CN | S |
| 41. | -CH(CH₃)CONH₂ | S |
| 42. | -CH₂CH₂NH₂ | S |
| 43. | -CH(CH₃)CH₂CN | CH₂ |
| 44. | -CH(CH₃)CH₂CN | S |
| 45. | -CH₂CH₂CN | CH₂ |
| 46. | -CH(CH₃)CN | CH₂ |
| 47. | 4-carbamoylpyrrolidin-2-yl (NH) | CH₂ |
| 48. | (2S,4S)-4-carbamoylpyrrolidin-2-yl | CH₃ ▲ H |
| 49. | (3R)-pyrrolidin-3-yl (NH) | CH₃ ▲ H |
| 50. | -CH₂-C(=NH)-N(3-oxopiperazin-1-yl) | CH₃ ▲ H |
| 51. | -CH₂-C(=NH)-N(3-oxopiperazin-1-yl) | CH₂ |
| 52. | -CH₂-C(=NH)-N(2,6-dioxopiperazin-1-yl) | CH₂ |
| 53. | -CH₂-C(=NH)-N(2,6-dioxopiperazin-1-yl) | CH₃ ▲ H |
| 54. | -CH₂-C(=NH)-N(3-carbamoyloxy-pyrrolidin-1-yl) | CH₂ |
| 55. | -CH₂-C(=NH)-N(3-carbamoyloxy-3-methylpyrrolidin-1-yl) | CH₃ ▲ H |
| 56. | -CH₂-C(=NH)-N(4-hydroxyiminopiperidin-1-yl) | CH₂ |
| 57. | -CH₂-C(=NH)-N(4-hydroxyiminopiperidin-1-yl) | CH₃ ▲ H |
| 58. | -CH₂-C(=NH)-N(CH₃)(CH₂CH₂OCONH₂) | CH₂ |
| 59. | -CH₂-C(=NH)-N(CH₃)(CH₂CH₂OCONH₂) | CH₃ ▲ H |
| 60. | -CH₂-C(=NH)-N(4-methyl-3-oxopiperazin-1-yl) | CH₂ |

-continued

| Comp. No. | R¹ | Y |
|---|---|---|
| 61. | -CH₂-C(=NH)-N(piperazine with N-CH₃ and C=O) | CH₃ ⫽ H (CH₃/H stereocenter) |
| 62. | -CH₂-C(=NH)-N(thiomorpholine-S,S-dioxide) | CH₂ |
| 63. | -CH₂-C(=NH)-N(thiomorpholine-S,S-dioxide) | CH₃ ⫽ H |
| 64. | -CH₂-C(=NH)-N(thiazolidine-S,S-dioxide) | CH₂ |
| 65. | -CH₂-C(=NH)-N(thiazolidine-S,S-dioxide) | CH₃ ⫽ H |
| 66. | pyrrolidine with CONH₂ and N-C(=NH)CH₃ | CH₂ |
| 67. | pyrrolidine with CONH₂ and N-C(=NH)CH₃ | CH₃ ⫽ H |
| 68. | pyrrolidine with CONH₂ and N-C(=NH)CH₃ | H₃CO ⫽ H |
| 69. | pyrrolidine with CONHCH₃ and N-C(=NH)CH₃ | CH₂ |
| 70. | pyrrolidine with CONHOCH₃ and N-C(=NH)CH₃ | CH₂ |
| 71. | pyrrolidine fused imidazoline with CH₃ | CH₂ |
| 72. | pyrrolidine fused imidazoline with CH₃ | CH₃ ⫽ H |
| 73. | pyrrolidine fused imidazoline with CH₂OCH₃ | CH₂ |
| 74. | pyrrolidine fused imidazoline with CH₂OCH₃ | CH₃ ⫽ H |
| 75. | pyrrolidine with N-C(CH₃)=NH | CH₂ |
| 76. | pyrrolidine with N-CH=NH | CH₂ |
| 77. | piperidine with N-CH₃ | CH₂ |
| 78. | piperidine with N-C(CH₃)=NH | CH₂ |
| 79. | pyrrolidine with N-COCH₃ | CH₂ |

Of the compounds listed above, we particularly prefer those which have the same configuration as thienamycin, i.e. (5R,6S)-6-[1(R)-hydroxyethyl]. In particular, the following compounds are preferred:

(5R,6S)-2-{2-[(aminomethylene)amino]ethylthio}-6-[1(R)-hydroxyethyl]-2-carbapenem-3-carboxylic acid (isomer of Compound No. 1)

(5R,6S)-2-[(3S)-1-acetimidoylpyrrolidin-3-ylthio]-6-[1(R)-hydroxyethyl]-2-carbapenem-3-carboxylic acid (isomer of Compound No. 6)

(5R,6S)-2-[(3R)-1-acetimidoylpyrrolidin-3-ylthio]-6-[1(R)-hydroxyethyl]-2-carbapenem-3-carboxylic acid (isomer of Compound No. 7)

(5R,6S)-2-[(3R)-1-acetimidoylpyrrolidin-3-ylthio]-6-[1(R)-hydroxyethyl]-1(S)-methyl-2-carbapenem-3-carboxylic acid (isomer of Compound No. 23)

(5R,6S)-2-[(3S)-1-acetimidoylpyrrolidin-3-ylthio]-6-[1(R)-hydroxyethyl]-1(R)-methyl-2-carbapenem-3-carboxylic acid (isomer of Compound No. 24)

(5R,6S)-2-[(3S)-1-acetimidoylpyrrolidin-3-ylthio]-6-[1(R)-hydroxyethyl]-1(S)-methyl-2-carbapenem-3-carboxylic acid (isomer of Compound No. 27)

(5R,6S)-2-[(3S)-1-acetimidoyl-5(S)-carbamoylpyrrolidin-3-ylthio]-6-[1(R)-hydroxyethyl]-2-carbapenem-3-carboxylic acid (isomer of Compound No. 28)

The above compounds may likewise be employed in the form of their pharmaceutically acceptable salts or esters, examples of which are well-known to those skilled in the art and which are given, for example, in U.S. Pat. No. 4,552,873, the disclosure of which is incorporated herein by reference.

The protective effect against renal toxicity appears to be exhibited by the whole range of amino acids wherein the amino and carboxylic acid groups are attached to a saturated aliphatic carbon chain or carbon atom. However, we have found that best results are achieved when employing N-acylated derivatives of those amino acids which may be represented by the formula (II):

$$H_2N\text{—}X\text{—}COOH \quad (II)$$

wherein X represents a $C_1$-$C_{10}$ alkylene group or a $C_1$-$C_{10}$ alkylene group having at least one substituent selected from the group consisting of hydroxy groups, $C_1$-$C_4$ alkoxy groups, $C_6$-$C_{14}$ aryloxy groups, substituted $C_6$-$C_{14}$ aryloxy groups, $C_7$-$C_9$ aralkyloxy groups, substituted $C_7$-$C_9$ aralkyloxy groups, mercapto groups, $C_1$-$C_4$ alkylthio groups, $C_6$-$C_{14}$ arylthio groups, substituted $C_6$-$C_{14}$ arylthio groups, $C_7$-$C_9$ aralkylthio groups, substituted $C_7$-$C_9$ aralkylthio groups, $C_2$-$C_5$ carboxyalkylthio groups, amino groups, amino groups having one or two substituents selected from the group consisting of $C_1$-$C_4$ alkyl groups, $C_6$-$C_{14}$ aryl groups, substituted $C_6$-$C_{14}$ aryl groups, $C_7$-$C_9$ aralkyl groups, substituted $C_7$-$C_9$ aralkyl groups and carboxylic acyl groups, $C_6$-$C_{14}$ aryl groups, substituted $C_6$-$C_{14}$ aryl groups, carboxy groups, amidino groups, sulfo groups, $C_1$-$C_4$ alkylsulfinyl groups, $C_1$-$C_4$ alkylsulfonyl groups and heterocyclic groups having from 5 to 14 ring atoms of which from 1 to 5 are hetero-atoms selected from the group consisting of nitrogen, oxygen and sulfur atoms, said substituted aryloxy, aralkyloxy, arylthio, aralkylthio, aryl and aralkyl groups having at least one substituent selected from the group consisting of $C_1$-$C_4$ alkyl groups, hydroxy groups, amino groups and $C_1$-$C_4$ alkoxy groups.

In general terms, the N-acylated derivatives of these amino acids may be represented by the formula (III):

$$R^2HN\text{—}X\text{—}COOH \quad (III)$$

wherein $R^2$ represents a carboxylic acyl group and X is as defined above.

N-acylated derivatives of ornithine and lysine may be represented by the general formula (IV):

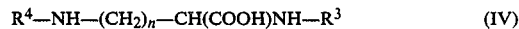

$$R^4\text{—}NH\text{—}(CH_2)_n\text{—}CH(COOH)NH\text{—}R^3 \quad (IV)$$

and phenylalanine and phenylglycine derivatives may be represented by the general formula (V):

$$Ph\text{—}(CH_2)_m\text{—}CH(COOH)\text{—}NHR^2 \quad (V)$$

In the above formulae, n represents the integer 3 or 4, whilst m represents the cypher 0 or the integer 1.

Ph represents the phenyl group.

$R^3$ and $R^4$ are independently selected from the group consisting of hydrogen atoms and carboxylic acyl groups, provided that $R^3$ and $R^4$ are not simultaneously hydrogen atoms.

Examples of carboxylic acyl groups which may be represented by $R^2$, $R^3$ and $R^4$ include:

alkanoyl groups, and preferably alkanoyl groups having from 1 to 18, more preferably from 1 to 10 and still more preferably from 1 to 8, e.g. from 2 to 5 or from 5 to 8, carbon atoms, for example the acetyl, propionyl, butyryl, isobutyryl, valeryl, isovaleryl, pivaloyl, hexanoyl, heptanoyl, octanoyl, nonanoyl and decanoyl groups; in the case of those amino acids (e.g. ornithine, lysine, phenylglycine and phenylalanine) which have relatively bulky and lipophilic groups, lower (e.g. $C_2$-$C_5$) alkanoyl groups are preferred; for others (e.g. glycine), higher (e.g. $C_5$-$C_8$) groups are preferred;

alkenoyl and alkynoyl groups, and more preferably such groups having from 3 to 8, more preferably 3 or 4, carbon atoms, for example the acryloyl, methacryloyl, crotonoyl or propioloyl groups;

aromatic acyl groups in which the aryl ring is a carbocyclic ring having from 6 to 14, preferably 6 to 10, carbon atoms and optionally having from 1 to 5, more preferably from 1 to 3, substituents preferably selected from the group consisting of $C_1$-$C_4$ alkyl groups, hydroxy groups, $C_1$-$C_4$ alkoxy groups, amino groups, sulfo groups and halogen atoms, for example the benzoyl and naphthoyl (1- or 2-naphthoyl) groups and the benzoyl and naphthoyl (1- or 2-naphthoyl) groups having one or more of the above substituents, for example the p-toluoyl, m-toluoyl, o-toluoyl, 4-butylbenzoyl, 4-hydroxybenzoyl, 3-hydroxybenzoyl, 2-hydroxybenzoyl, 4-methoxybenzoyl, 3-methoxybenzoyl, 2-methoxybenzoyl, 4-butoxybenzoyl, 4-aminobenzoyl, 3-aminobenzoyl, 2-aminobenzoyl, 3-sulfobenzoyl, 4-chlorobenzoyl, 3-fluorobenzoyl, 2-bromobenzoyl, 3-hydroxy-2-naphthoyl and 1-hydroxy-2-naphthoyl groups;

alicyclic acyl groups in which the carbocyclic ring has from 3 to 8 carbon atoms, more preferably from 3 to 6 carbon atoms, and in which the cycloalkane ring is unsubstituted or has at least one substituent selected from the group consisting of $C_1$-$C_4$ alkyl groups and phenyl groups, for example the cyclopropanecarbonyl, cyclobutanecarbonyl, cyclopentanecarbonyl, cyclohexanecarbonyl, 1-phenyl-1-cyclopropanecarbonyl, 1-phenyl-1-cyclopentanecarbonyl, 1-methyl-1-cyclohexanecarbonyl and 1-phenyl-1-cyclohexanecarbonyl groups;

araliphatic acyl groups in which the aryl ring is a carbocyclic ring having from 6 to 14, preferably 6 to 10, carbon atoms and optionally having from 1 to 5, more preferably from 1 to 3, substituents preferably selected from the group consisting of $C_1-C_4$ alkyl groups, hydroxy groups, $C_1-C_4$ alkoxy groups, amino groups, sulfo groups and halogen atoms, and in which the alkyl moiety has from 1 to 4 carbon atoms, such as the phenylacetyl, α-phenyl-α-methylacetyl, α-phenyl-α-ethylacetyl, α,α-diphenylacetyl, α-phenyl-α-cyclopentylacetyl, 3-phenylpropionyl, 4-phenylbutyryl, 4-tolylacetyl, 4-hydroxyphenylacetyl, 4-aminophenylacetyl, 4-methoxyphenylacetyl, 3-sulfophenylacetyl and 4-chlorophenylacetyl groups;

heterocyclic acyl groups which may have saturated or unsaturated ring systems, the rings having 5 to 6 ring atoms, of which from 1 to 3 are hetero-atoms independently selected fronm the group consisting of nitrogen, sulfur and oxygen atoms and the ring being unsubstituted or having from 1 to 3 substituents selected from the group consisting of $C_1-C_4$ alkyl groups and hydroxy groups, for example the nicotinoyl, 2-thiophenecarbonyl, 2-furoyl, 2-pyrazinecarbonyl, 2-piperidinecarbonyl, N-methylnicotinoyl and 6-hydroxynicotinoyl groups;

alkoxycarbonyl groups having a total of from 2 to 7 carbon atoms, for example the methoxycarbonyl, ethoxycarbonyl, propoxycarbonyl, isopropoxycarbonyl, butoxycarbonyl, t-butoxycarbonyl and pentyloxycarbonyl groups; and aralkyloxycarbonyl groups in which the aralkyl moiety has from 7 to 9 carbon atoms and is unsubstituted or has from 1 to 5, more preferably from 1 to 3, substituents selected from the group consisting of amino groups, $C_1-C_4$ alkyl groups, $C_1-C_4$ alkoxy groups and hydroxy groups, for example the benzyloxycarbonyl, α-methylbenzyloxycarbonyl, phenethyloxycarbonyl, 3-phenylpropoxycarbonyl, 4-methoxybenzyloxycarbonyl, 4-hydroxybenzyloxycarbonyl, p-tolyloxycarbonyl and 4-aminobenzyloxycarbonyl groups.

In addition to the acyl groups listed above, $R^2$, $R^3$ or $R^4$ can also represent an acyl group derived from an amino acid by removal of OH from the carboxylic acid group and N-acylation of the amino group with at least one of the above-mentioned acyl groups. Hence, $R^2$, $R^3$ and $R^4$ can also represent such an acyl group connected to the parent amino acid via one or more amino acid residues, preferably from 0 to 5, more preferably from 0 to 3 and most preferably from 0 to 2, such residues. Hence, $R^2$, $R^3$ or $R^4$ could represent a group derived from an N-acylated amino acid, for example the N-benzoylglycyl or N-benzoylglycylglycyl group. Hence, compounds of formula (I) also include such oligopeptide compounds as N-benzoylglycylglycine, N-benzoylglycylglycylglycine and similar compounds.

Preferred examples of groups which may be represented by $R^2$, $R^3$ and $R^4$ include: saturated aliphatic acyl groups having from 1 to 8 carbon atoms; aromatic acyl groups in which the aryl moiety has from 6 to 10 ring carbon atoms and is unsubstituted or has from 1 to 3 substituents independently selected from the group consisting of $C_1-C_4$ alkyl groups and $C_1-C_4$ alkoxy groups; alicyclic acyl groups in which the cycloalkane ring has from 3 to 6 carbon atoms; araliphatic acyl groups in which the aryl ring has from 6 to 10 ring carbon atoms and the alkyl group has from 1 to 4 carbon atoms, the aryl ring being unsubstituted or having from 1 to 3 substituents independently selected from the group consisting of $C_1-C_4$ alkyl groups and $C_1-C_4$ alkoxy groups; heterocyclic acyl groups in which the heterocyclic ring is saturated or unsaturated and has 5 or 6 ring atoms of which one is a nitrogen, sulfur or oxygen hetero-atom; alkoxycarbonyl groups having a total of from 2 to 7 carbon atoms; and aralkyloxycarbonyl groups in which the aralkyl moiety has from 7 to 9 carbon atoms and the aryl ring is unsubstituted or has from 1 to 3 substituents independently selected from the group consisting of $C_1-C_4$ alkyl groups and $C_1-C_4$ alkoxy groups.

Particularly preferred groups which may be represented by $R^2$, $R^3$ and $R^4$ include: aromatic acyl groups in which the aryl ring has from 6 to 10 ring atoms and which is unsubstituted or has a single substituent selected from the group consisting of $C_1-C_4$ alkyl groups, $C_1-C_4$ alkoxy groups, hydroxy groups and amino groups; alicyclic acyl groups in which the cycloalkane moiety has from 3 to 6 carbon atoms; phenylaliphatic acyl groups in which the phenyl groups is unsubstituted or has a single $C_1-C_4$ alkyl substituent, and in which the alkyl part has from 1 to 4 carbon atoms; alkoxycarbonyl groups having a total of from 4 to 6 carbon atoms; and aralkyloxycarbonyl groups in which the aralkyl part has from 7 to 9 carbon atoms and has 0 or 1 substituent selected from the group consisting of $C_1-C_4$ alkyl groups and $C_1-C_4$ alkoxy groups.

In addition, such acyl groups linked to the amino acid via at least one further amino acid residue are preferred.

Of the groups exemplified above, the following are most preferred: acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, naphthoxyl, toluoyl, benzyloxycarbonyl and 4-methoxybenzyloxycarbonyl groups, of which the acetyl and benzoyl, particularly benzoyl, groups are most preferred.

As explained previously, the lower alkanoyl groups, notably the acetyl group, are only most preferred in relation to their use with those amino acids which have relatively bulky and lipophilic groups.

In the compounds of formula (II), X represents an alkylene group having from 1 to 10, preferably from 1 to 8 and more preferably from 1 to 5, carbon atoms. Such groups may have the "free" valencies attached to different carbon atoms or to the same carbon atom. In the latter case, the groups are sometimes referred to as "alkylidene" groups. Examples include the methylene, ethylidene, ethylene, propylidene, 1-methylethylidene, 1-methylethylene, trimethylene, butylidene, 2-methylpropylidene, 1-methylpropylidene, 1,2-dimethylethylene, 1-ethylethylene, 1-methyltrimethylene, 2-methyltrimethylene, tetramethylene, pentylidene, 3-methylbutylidene, 2-methylbutylidene, 2,2-dimethylpropylidene, 1-ethylpropylidene, 1,2-dimethylpropylidene, 1-propylethylene, 1-(1-methylethyl)ethylene, 1-ethyl-2- methylene, 1-ethyltrimethylene, 2-ethyltrimethylene, 1,3-dimethyltrimethylene, 1-methyltetramethylene, 2-methyltetramethylene, pentamethylene, hexylidene, 4-methylpentylidene, 3-methylpentylidene, 2-methylpentylidene, 1-methylpentylidene, 2-ethylbutylidene, 1-ethylbutylidene, 1,3-dimethylbutylidene, 1,2-dimethylbutylidene, 3,3-dimethylbutylidene, 2,3-dimethylbutylidene, 1-butylethylene, 1-methyl-2-propylethylene, 1,2-diethylethylene, 1-methyl-1-propylethylene, 2-propyltrimethylene, 1-ethyl-3-methyltrimethylene, 1-ethyltetramethylene, 2-ethyltetramethylene, 1,3-dimethyltetramethylene, 1-methylpentamethylene, 2-methylpentamethylene, 3-methylpentamethylene, hexamethylene, heptylidene, 5-methylhexylidene, 4-methylhexylidene, 3-methylhexylidene, 1-methylhexylidene, 3-ethylpentylidene, 1-ethylpentylidene, 4,4-dimethylpentylidene, 2,4-dimethylpentylidene, 1,2-dimethylpentylidene, 1-propylbutylidene, 2-ethyl-1-methylbutylidene, 1-ethyl-2-methylbutylidene, 1,2,2-trimethylbutylidene, 1,2,3-trimethylbutylidene, 1-pentylethylene, 1-butyl-2-methylethylene, 1-ethyl-2-propylethylene, 1-butyl-1-methylethylene, 1-ethyl-1-propylethylene, 1-butyltrimethylene, 2-butyltrimethylene, 1,3-diethyltrimethylene, 1-methyl-3-propyltrimethylene, 1-propyltetramethylene, 2-propyltetramethylene, 1-ethyl-4-methyltetramethylene, 3-ethyl-1-methyltetramethylene, 1-ethylpentamethylene, 3-ethylpentamethylene, 1,3-dimethylpentamethylene, 1-methylhexamethylene, 3-methylhexamethylene, heptamethylene, octylidene, 6-methylheptylidene, 4-methylheptylidene, 2-methylheptylidene, 1-methylheptylidene, 4-ethylhexylidene, 3-ethylhexylidene, 2-ethylhexylidene, 1-ethylhexylidene, 3,5-dimethylhexylidene, 4,5-dimethylhexylidene, 2,4-dimethylhexylidene, 1,5-dimethylhexylidene, 1,4-dimethylhexylidene, 2-propylpentylidene, 1-propylpentylidene, 2-ethyl-4-methylpentylidene, 3-ethyl-2-methylpentylidene, 3-ethyl-1-methylpentylidene, 1-ethyl-3-methylpentylidene, 3-methyl-1-propylbutylidene, 2-methyl-1-propylbutylidene, 1-ethyl-2,3-dimethylbutylidene, 1,2-diethylbutylidene, 1-hexylethylene, 1-methyl-2-pentylethylene, 1-butyl-2-ethylethylene, 1,2-dipropylethylene, 1-pentyltrimethylene, 2-pentyltrimethylene, 1-butyl-3-methyltrimethylene, 1-butyl-2-methyltrimethylene, 1-ethyl-3-propyltrimethylene, 1,2-dimethyl-3-propyltrimethylene, 1-butyltetramethylene, 1-methyl-4-propyltetramethylene, 1-propylpentamethylene, 3-propylpentamethylene, 2-ethyl-4-methylpentamethylene, 1-ethylhexamethylene, 3-ethylhexamethylene, 1,3-dimethylhexamethylene, 1-methylheptamethylene, 4-methylheptamethylene and octamethylene groups.

The alkylene group represented by X, including those alkylene groups exemplified above, may be unsubstituted or may have at least 1, preferably from 1 to 4 and more preferably 1 or 2, substituents selected from the following groups:
  hydroxy groups;
  $C_1$–$C_4$ alkoxy groups, for example the methoxy or ethoxy groups;
  aryloxy groups in which the aryl ring has from 6 to 14, more preferably from 6 to 10, ring carbon atoms and which is unsubstituted or has from 1 to 5, more preferably from 1 to 3, substituents selected from the group consisting of $C_1$–$C_4$ alkyl groups, hydroxy groups, amino groups and $C_1$–$C_4$ alkoxy groups, for example the phenoxy, p-tolyloxy, 4-hydroxyphenoxy, 4-aminophenoxy and 4-methoxyphenoxy groups;
  $C_7$–$C_9$ aralkyloxy groups in which the aryl ring is unsubstituted or has from 1 to 5, more preferably from 1 to 3, substituents selected from the group consisting of $C_1$–$C_4$ alkyl groups, hydroxy groups, amino groups and $C_1$–$C_4$ alkoxy groups, for example the benzyloxy, 4-methylbenzyloxy, 4-hydroxybenzyloxy, 4-aminobenzyloxy and 4-methoxybenzyloxy groups;
  mercapto groups;
  $C_1$–$C_4$ alkylthio groups, for example the methylthio or ethylthio groups;
  arylthio groups in which the aryl ring has from 6 to 14, more preferably from 6 to 10, ring carbon atoms and which is unsubstituted or has from 1 to 5, more preferably from 1 to 3, substituents selected from the group consisting of $C_1$–$C_4$ alkyl groups, hydroxy groups, amino groups and $C_1$–$C_4$ alkoxy groups, for example the phenylthio, p-tolylthio, 4-hydroxyphenylthio, 4-aminophenylthio and 4-methoxyphenylthio groups;
  $C_7$–$C_9$ aralkylthio groups in which the aryl ring is unsubstituted or has from 1 to 5, more preferably from 1 to 3, substituents selected from the group consisting of $C_1$–$C_4$ alkyl groups, hydroxy groups, amino groups and $C_1$–$C_4$ alkoxy groups, for example the benzylthio, 4-methylbenzylthio, 4-hydroxybenzylthio, 4-aminobenzylthio and 4-methoxybenzylthio groups;
  carboxyalkylthio groups having from 1 to 4 carbon atoms in the alkyl moiety, for example the carboxymethylthio and carboxyethylthio groups;
  amino groups;
  amino groups having one or two $C_1$–$C_4$ alkyl substituents, for example the methylamino, ethylamino and dimethylamino groups;
  amino groups having one or two aryl substituents, wherein the aryl ring has from 6 to 14 ring carbon atoms and is unsubstituted or has from 1 to 5, preferbly from 1 to 3, substituents selected from the group consisting of $C_1$–$C_4$ alkyl groups, hydroxy groups, amino groups, and $C_1$–$C_4$ alkoxy groups, such as the phenylamino, p-tolylamino, 4-hydroxyphenylamino, 4-aminophenylamino and 4-methoxyphenylamino groups;
  amino groups having one or two $C_7$–$C_9$ aralkyl substituents wherein the aryl moiety is unsubstituted or has from 1 to 5, preferably from 1 to 3, substituents selected from the group consisting of $C_1$–$C_4$ alkyl groups, hydroxy groups, amino groups and $C_1$–$C_4$ alkyl groups, such as the benzylamino, 4-methylbenzylamino, 4-hydroxybenzylamino, 4-aminobenzylamino and 4-methoxybenzylamino groups;
  amino groups substituted by one or two carboxylic acyl groups as defined in relation to $R^2$, $R^3$ and $R^4$;
  aryl groups having from 6 to 14 ring carbon atoms, and being unsubstituted or having from 1 to 5, preferably from 1 to 3, substituents selected from the group consisting of $C_1$–$C_4$ alkyl groups, hydroxy groups, amino groups and $C_1$–$C_4$ alkoxy groups;
  carboxy groups;

amidino groups;
sulfo groups;
$C_1-C_4$ alkylsulfinyl groups, such as the methanesulfinyl or ethanesulfinyl groups;
$C_1-C_4$ alkylsulfonyl groups, such as the methanesulfonyl or ethanesulfonyl groups; and
heterocyclic groups, such as the pyrrolyl, imidazolyl, pyrazolyl, pyridyl, pyrazinyl, pyrimidinyl, pyridazinyl, indolazinyl, indolyl and indazolyl groups.

Preferred groups which may be represented by X include $C_1-C_5$ alkylene groups which are unsubstituted or have one or two substituents independently selected from the group consisting of: hydroxy groups; $C_1-C_4$ alkoxy groups; aryloxy groups wherein the aryl ring has from 6 to 14 ring carbon atoms and which is unsubstituted or has from 1 to 3 substituents independently selected from the group consisting of $C_1-C_4$ alkyl groups, hydroxy groups, amino groups and $C_1-C_4$ alkoxy groups; $C_7-C_9$ aralkyloxy groups, wherein the aryl moiety is unsubstituted or has from 1 to 3 substituents independently selected from the group consisting of $C_1-C_4$ alkyl groups, hydroxy groups, amino groups and $C_1-C_4$ alkoxy groups; mercapto groups; $C_1-C_4$ alkylthio groups; arylthio groups wherein the aryl ring has from 6 to 14 ring carbon atoms and which is unsubstituted or has from 1 to 3 substituents independently selected from the group consisting of $C_1-C_4$ alkyl groups, hydroxy groups, amino groups and $C_1-C_4$ alkoxy groups; $C_7-C_9$ aralkylthio groups wherein the aryl ring is unsubstituted or has from 1 to 3 substituents independently selected from the group consisting of $C_1-C_4$ alkyl groups, hydroxy groups, amino groups and $C_1-C_4$ alkoxy groups; carboxyalkylthio groups in which the alkyl part has from 1 to 4 carbon atoms; amino groups; amino groups having one or two $C_1-C_4$ alkyl substituents; amino groups having one or two aryl substituents in which the aryl ring has from 6 to 14 ring carbon atoms and is unsubstituted or has from 1 to 3 substituents independently selected from the group consisting of $C_1-C_4$ alkyl groups, hydroxy groups, amino groups and $C_1-C_4$ alkoxy groups; amino groups having one or two $C_7-C_9$ aralkyl substituents in which the aryl part is unsubstituted or has from 1 to 3 substituents selected from the group consisting of $C_1-C_4$ alkyl groups, hydroxy groups, amino groups and $C_1-C_4$ alkoxy groups; amino groups having one or two carboxylic acyl substituents as defined in relation to $R^2$, $R^3$ and $R^4$; aryl groups having from 6 to 14 ring carbon atoms and being unsubstituted or having from 1 to 3 substituents selected from the group consisting of $C_1-C_4$ alkyl groups, hydroxy groups, amino groups and $C_1-C_4$ alkoxy groups; carboxy groups; and heterocyclic groups having from 5 to 9 ring atoms, of which from 1 to 3 are hetero-atoms selected from the group consisting of nitrogen, oxygen and sulfur hetero-atoms.

More preferred groups which may be represented by X are $C_1-C_5$ alkylene groups which are unsubstituted or have 1 or 2 substituents independently selected from the group consisting of: hydroxy groups; $C_1-C_4$ alkoxy groups; mercapto groups; $C_1-C_4$ alkylthio groups; amino groups; amino groups having one or two $C_1-C_4$ alkyl substituents; amino groups having one or two carboxylic acyl substituents as defined for $R^2$, $R^3$ and $R^4$; aryl groups having from 6 to 14 carbon atoms wherein the aryl ring is unsubstituted or has from 1 to 3 substituents selected from the group consisting of $C_1-C_4$ alkyl groups, hydroxy groups, amino groups and $C_1-C_4$ alkoxy groups; carboxy groups; and heterocyclic groups having from 5 to 9 ring atoms, of which from 1 to 3 are hetero-atoms selected from the group consisting of nitrogen and oxygen hetero-atoms.

Preferred amino acids which may be represented by formula (II) include glycine, β-alanine, 4-aminobutyric acid, 5-aminovaleric acid, 6-aminohexanoic acid, 8-aminooctanoic acid, alanine, 2-aminobutyric acid, norvaline, valine, leucine, isoleucine, norleucine, phenylglycine, phenylalanine, tyrosine, O-methyltyrosine, aspartic acid, glutamic acid, 4-carboxyglutamic acid, 3-methylaspartic acid, 2-aminoadipic acid, 2-aminopimelic acid, 2-aminosuberic acid, 3-hydroxyaspartic acid, 3-hydroxyglutamic acid, 2,3-diaminopropionic acid, 2,4-diaminobutyric acid, ornithine, lysine, 5-hydroxylysine, arginine, $N^\delta,N^\delta$-dimethylornithine, $N^\epsilon$-methyllysine, cysteine, methionine, ethionine, S-carboxymethylcysteine, S-benzylcysteine, methionine S-oxide, ethionine S-oxide, methionine S,S-dioxide, cysteic acid, serine, O-methylserine, threonine, O-methylthreonine, homothreonine, ethoxinine (=2-amino-4-ethoxybutyric acid), 3-methoxyvaline, 3-phenylserine, 3-methyl-3-phenylalanine, histidine, tryptophan, 2-methylalanine, 2-methylserine, 2-hydroxyisoleucine, 2-methylmethionine, 2-ethyl-2-phenylglycine, 3-aminobutyric acid, 3-amino-4-methylvaleric acid, 3-amino-3-phenylpropionic acid, 3-amino-2-hydroxypropionic acid and 4-amino-3-hydroxybutyric acid.

More preferred amino acids are glycine, β-alanine, 4-aminobutyric acid, 5-aminovaleric acid, 6-aminohexanoic acid, 8-aminooctanoic acid, alanine, norvaline, valine, leucine, isoleucine, norleucine, $N^\delta,N^\delta$-dimethylornithine, methionine, ethionine, O-methylserine, O-methylthreonine, ethoxinine, 3-methoxyvaline, 3-phenylserine, 3-methyl-3-phenylalanine, histidine, 2-methylalanine, 2-methylserine, 2-hydroxyisoleucine, 2-ethylphenylglycine, 3-aminobutyric acid, 3-amino-4-methylvaleric acid, 3-amino-3-phenylpropionic acid, ornithine, lysine, phenylalanine and phenylglycine.

The most preferred amino acids are β-alanine, 4-aminobutyric acid, 5-aminovaleric acid, 6-aminohexanoic acid, alanine, valine, leucine, norleucine, methionine, histidine, ornithine, glycine, phenylalanine and phenylglycine.

When the amino acid derivative is an oligopeptide compound, such as a dipeptide or tripeptide, this type of compound is preferably formed by suitable combination of such amino acids as glycine, β-alanine, 4-aminobutyric acid, 5-aminovaleric acid, 6-aminohexanoic acid, alanine, valine, leucine, norleucine, phenylglycine, phenylalanine, methionine and histidine. Examples include leucylglycine, glycyl-β-alanine, glycylalanine, valylalanine, leucylalanine, glycylvaline, alanylvaline, leucylvaline, valylleucine, phenylalanylleucine, histidylleucine, glycylphenylalanine, alanylphenylalanine, leucylphenylalanine, glycylmethionine, valylmethionine, glycylhistidine, alanylvalylglycine, glycylalanylvaline, glycylphenylalanylleucine and glycylglycylhistidine.

Specific examples of the amino acid compounds which may be employed in the present invention are given in the following list. It should, of course, be appreciated that these compounds can exist in the D-, L- and DL-forms and any of these forms can be employed. The compounds are hereinafter referred to by the numbers appended to them in this list. In the case of the mono-acylated derivatives of ornithine or substituted ornithine compounds, the acyl group can be present on either the $N^\alpha$- or the $N^\delta$-position, whilst, in the case of mono-acylated derivatives of lysine or substituted lysine compounds, the acyl group can be present on either the $N^\alpha$- or $N^\epsilon$-position. Of course, the respective individual mono-acylated derivatives or a mixture of the $N^\alpha$ and $N^\delta$ or $N^\alpha$ and $N^\epsilon$ derivatives may be used. When the compounds of the invention are hereinafter referred to by the numbers appended to them in the following list, the $N^\alpha$ isomer is identified by the appropriate number followed by the character "$\alpha$", the $N^\delta$ isomer is identified by the number followed by "$\delta$" and the $N^\epsilon$ isomer is identified by the number followed by "$\epsilon$". Where the number alone is given, a mixture is meant. Where the compound is identified by the number followed by "$\alpha/\delta$" or "$\alpha/\epsilon$", this defines specifically the three options: the isolated $N^\alpha$ isomer; the isolated $N^\delta$ isomer or $N^\epsilon$ isomer; or a mixture of these two isomers. Other derivatives of amino acids having 2 or more amino groups (e.g. 2,3-diaminopropionic acid, 2,4-diaminobutyric acid and arginine) are identified similarly.

1. Glycine derivatives
   1-1. N-hexanoylglycine
   1-2. N-heptanoylglycine
   1-3. N-octanoylglycine
   1-4. N-nonanoylglycine
   1-5. N-decanoylglycine
   1-6. N-(p-toluoyl)glycine
   1-7. N-(4-methoxybenzoyl)glycine
   1-8. N-(1-naphthoyl)glycine
   1-9. N-(1-phenyl-1-cyclohexanecarbonyl)glycine
   1-10. N-(α,α-diphenylacetyl)glycine
   1-11. N-(α-phenyl-α-cyclopentylacetyl)glycine
   1-12. N-butoxycarbonylglycine
   1-13. N-octanoylleucylglycine
   1-14. N-benzoylleucylglycine
   1-15. N-butoxycarbonylleucylglycine
   1-16. N-octanylalanylvalylglycine
   1-17. N-benzoylalanylvalylglycine
   1-18. N-cyclohexanecarbonylalanylvalylglycine
   1-19. N-butoxycarbonylalanylvalylglycine 2. β-Alanine derivatives
   2-1. N-hexanoyl-β-alanine
   2-2. N-heptanoyl-β-alanine
   2-3. N-octanoyl-β-alanine
   2-4. N-nonanoyl-β-alanine
   2-5. N-(p-toluoyl)-β-alanine
   2-6. N-(4-methoxybenzoyl)-β-alanine
   2-7. N-(3-hydroxy-2-naphthoyl)-β-alanine
   2-8. N-(1-phenyl-1-cyclopentanecarbonyl)-β-alanine
   2-9. N-(α,α-diphenylacetyl)-β-alanine
   2-10. N-(3-phenylpropionyl)-β-alanine
   2-11. N-(4-phenylbutyryl)-β-alanine
   2-12. N-(4-methoxyphenylacetyl)-β-alanine
   2-13. N-t-butoxycarbonyl-β-alanine
   2-14. N-benzyloxycarbonyl-β-alanine
   2-15. N-(4-methoxybenzyloxycarbonyl)-β-alanine
   2-16. N-(4-methylbenzyloxycarbonyl)-β-alanine
   2-17. N-(α-methylbenzyloxycarbonyl)-β-alanine
   2-18. N-benzoylglycyl-β-alanine
   2-19. N-(1-naphthoyl)glycyl-β-alanine
   2-20. N-cyclohexanecarbonylglycyl-β-alanine
   2-21. N-benzyloxycarbonylglycyl-β-alanine
   2-22. N-benzoyl-β-alanine 3. 4-Aminobutyric acid derivatives.
   3-1. N-hexanoyl-4-aminobutyric acid
   3-2. N-heptanoyl-4-aminobutyric acid
   3-3. N-benzoyl-4-aminobutyric acid
   3-4. N-(p-toluoyl)-4-aminobutyric acid
   3-5. N-(3-methoxybenzoyl)-4-aminobutyric acid
   3-6. N-cyclopentanecarbonyl-4-aminobutyric acid
   3-7. N-cyclohexanecarbonyl-4-aminobutyric acid
   3-8. N-(1-phenyl-1-cyclopropanecarbonyl)-4-aminobutyric acid
   3-9. N-(1-phenyl-1-cyclopentanecarbonyl)-4-aminobutyric acid
   3-10. N-phenylacetyl-4-aminobutyric acid
   3-11. N-(3-phenylpropionyl)-4-aminobutyric acid
   3-12. N-(p-tolylacetyl)-4-aminobutyric acid
   3-13. N-nicotinoyl-4-aminobutyric acid
   3-14. N-butoxycarbonyl-4-aminobutyric acid
   3-15. N-benzyloxycarbonyl-4-aminobutyric acid
   3-16. N-(3-phenylpropoxycarbonyl)-4-aminobutyric acid
   3-17. N-(α-methylbenzyloxycarbonyl)-4-aminobutyric acid
   3-18. N-(1-naphthoyl)-4-aminobutyric acid 4. 5-Aminovaleric acid derivatives
   4-1. N-butyryl-5-aminovaleric acid
   4-2. N-isobutyryl-5-aminovaleric acid
   4-3. N-valeryl-5-aminovaleric acid
   4-4. N-isovaleryl-5-aminovaleric acid
   4-5. N-hexanoyl-5-aminovaleric acid
   4-6. N-benzoyl-5-aminovaleric acid
   4-7. N-(m-toluoyl)-5-aminovaleric acid
   4-8. N-(2-methoxybenzoyl)-5-aminovaleric acid
   4-9. N-cyclopentanecarbonyl-5-aminovaleric acid
   4-10. N-cyclohexanecarbonyl-5-aminovaleric acid
   4-11. N-(1-phenyl-1-cyclopropanecarbonyl)-5-aminovaleric acid
   4-12. N-(1-phenyl-1-cyclohexanecarbonyl)-5-aminovaleric acid
   4-13. N-phenylacetyl-5-aminovaleric acid
   4-14. N-(α-phenyl-α-methylacetyl)-5-aminovaleric acid
   4-15. N-nicotinoyl-5-aminovaleric acid
   4-16. N-(2-thiophenecarbonyl)-5-aminovaleric acid
   4-17. N-(2-furoyl)-5-aminovaleric acid
   4-18. N-isopropoxycarbonyl-5-aminovaleric acid
   4-19. N-pentyloxycarbonyl-5-aminovaleric acid
   4-20. N-benzyloxycarbonyl-5-aminovaleric acid
   4-21. N-(4-methoxybenzyloxycarbonyl)-5-aminovaleric acid
   4-22. N-(4-methylbenzyloxycarbonyl)-5-aminovaleric acid
   4-23. N-(4-hydroxyphenylacetyl)-5-aminovaleric acid
   4-24. N-(N-methylnicotinoyl)-5-aminovaleric acid 5. 6-Aminohexanoic acid derivatives.
   5-1. N-acetyl-6-aminohexanoic acid 5-2. N-propionyl-6-aminohexanoic acid
5-3. N-butyryl-6-aminohexanoic acid
5-4. N-isobutyryl-6-aminohexanoic acid
5-5. N-isovaleryl-6-aminohexanoic acid
5-6. N-hexanoyl-6-aminohexanoic acid
5-7. N-acryloyl-6-aminohexanoic acid
5-8. N-methacryloyl-6-aminohexanoic acid
5-9. N-crotonoyl-6-aminohexanoic acid
5-10. N-propioloyl-6-aminohexanoic acid
5-11. N-benzoyl-6-aminohexanoic acid
5-12. N-(o-toluoyl)-6-aminohexanoic acid
5-13. N-(4-methoxybenzoyl)-6-aminohexanoic acid
5-14. N-(4-aminobenzoyl)-6-aminohexanoic acid
5-15. N-(1-naphthoyl)-6-aminohexanoic acid
5-16. N-cyclobutanecarbonyl-6-aminohexanoic acid
5-17. N-cyclopentanecarbonyl-6-aminohexanoic acid
5-18. N-cyclohexanecarbonyl-6-aminohexanoic acid
5-19. N-phenylacetyl-6-aminohexanoic acid
5-20. N-(3-phenylpropionyl)-6-aminohexanoic acid
5-21. N-nicotinoyl-6-aminohexanoic acid
5-22. N-(2-thiophenecarbonyl)-6-aminohexanoic acid
5-23. N-methoxycarbonyl-6-aminohexanoic acid
5-24. N-ethoxycarbonyl-6-aminohexanoic acid
5-25. N-butoxycarbonyl-6-aminohexanoic acid
5-26. N-pentyloxycarbonyl-6-aminohexanoic acid
5-27. N-benzyloxycarbonyl-6-aminohexanoic acid
5-28. N-phenethyloxycarbonyl-6-aminohexanoic acid
5-29. N-(3-phenylpropoxycarbonyl)-6-aminohexanoic acid
5-30. N-(4-methoxybenzyloxycarbonyl)-6-aminohexanoic acid
5-31. N-(4-methylbenzyloxycarbonyl)-6-aminohexanoic acid
5-32. N-($\alpha$-methylbenzyloxycarbonyl)-6-aminohexanoic acid
5-33. N-(N-methylnicotinoyl)-6-aminohexanoic acid
5-34. N-(4-chlorophenylacetyl)-6-aminohexanoic acid 6. 8-Aminooctanoic acid derivatives.
6-1. N-acetyl-8-aminooctanoic acid
6-2. N-valeryl-8-aminooctanoic acid
6-3. N-benzoyl-8-aminooctanoic acid
6-4. N-(3-hydroxybenzoyl)-8-aminooctanoic acid
6-5. N-(3-sulfobenzoyl)-8-aminooctanoic acid
6-6. N-cyclopropanecarbonyl-8-aminooctanoic acid
6-7. N-(4-aminophenylacetyl)-8-aminooctanoic acid
6-8. N-methoxycarbonyl-8-aminooctanoic acid
6-9. N-propoxycarbonyl-8-aminooctanoic acid
6-10. N-isopropoxycarbonyl-8-aminooctanoic acid
6-11. N-benzyloxycarbonyl-8-aminooctanoic acid
6-12. N-(4-hydroxybenzyloxycarbonyl)-8-aminooctanoic acid
6-13. N-(N-methylnicotinoyl)-8-aminooctanoic acid
6-14. N-(6-hydroxynicotinoyl)-8-aminooctanoic acid 7. Alanine derivatives.
7-1. N-valerylalanine
7-2. N-hexanoylalanine
7-3. N-benzoylalanine
7-4. N-(4-methoxybenzoyl)alanine
7-5. N-(1-naphthoyl)alanine
7-6. N-(1-phenyl-1-cyclopropanecarbonyl)alanine
7-7. N-phenylacetylalanine
7-8. N-butoxycarbonylalanine
7-9. N-benzyloxycarbonylalanine
7-10. N-($\alpha$-methylbenzyloxycarbonyl)alanine
7-11. N-octanoylglycylalanine
7-12. N-benzoylglycylalanine
7-13. N-butoxycarbonylglycylalanine
7-14. N-benzoylvalylalanine
7-15. N-(p-toluoyl)valylalanine
7-16. N-cyclopentanecarbonylvalylalanine
7-17. N-cyclohexanecarbonylvalylalanine
7-18. N-benzyloxycarbonylvalylalanine
7-19. N-benzoylleucylalanine
7-20. N-(4-methoxybenzoyl)leucylalanine
7-21. N-butoxycarbonylleucylalanine
7-22. N-benzyloxycarbonylleucylalanine
7-23. N-(2-bromobenzoyl)alanine 8. 2-Aminobutyric acid derivatives.
8-1. N-pivaloyl-2-aminobutyric acid
8-2. N-hexanoyl-2-aminobutyric acid
8-3. N-heptanoyl-2-aminobutyric acid
8-4. N-benzoyl-2-aminobutyric acid
8-5. N-(p-toluoyl)-2-aminobutyric acid
8-6. N-(1-phenyl-1-cyclopentanecarbonyl)-2-aminobutyric acid
8-7. N-($\alpha,\alpha$-diphenylacetyl)-2-aminobutyric acid
8-8. N-ethoxycarbonyl-2-aminobutyric acid
8-9. N-benzyloxycarbonyl-2-aminobutyric acid
8-10. N-(4-methoxybenzyloxycarbonyl)-2-aminobutyric acid 9. Norvaline derivatives.
9-1. N-valerylnorvaline
9-2. N-decanoylnorvaline
9-3. N-benzoylnorvaline
9-4. N-(m-toluoyl)norvaline
9-5. N-(3-sulfobenzoyl)norvaline
9-6. N-cyclohexanecarbonylnorvaline
9-7. N-(1-phenyl-1-cyclohexanecarbonyl)norvaline
9-8. N-($\alpha$-phenyl-$\alpha$-ethylacetyl)norvaline
9-9. N-(4-methoxyphenylacetyl)norvaline
9-10. N-(2-pyrazinecarbonyl)norvaline
9-11. N-benzyloxycarbonylnorvaline
9-12. N-(4-methylbenzyloxycarbonyl)norvaline 10. Valine derivatives.
10-1. N-propionylvaline
10-2. N-butyrylvaline
10-3. N-isobutyrylvaline
10-4. N-valerylvaline
10-5. N-acryloylvaline
10-6. N-methacryloylvaline
10-7. N-crotonoylvaline
10-8. N-propioloylvaline
10-9. N-(2-methoxybenzoyl)valine
10-10. N-(4-butoxybenzoyl)valine
10-11. N-cyclopentanecarbonylvaline
10-12. N-cyclohexanecarbonylvaline
10-13. N-(1-phenyl-1-cyclopentanecarbonyl)valine
10-14. N-phenylacetylvaline
10-15. N-nicotinoylvaline
10-16. N-(2-piperidinecarbonyl)valine
10-17. N-ethoxycarbonylvaline
10-18. N-isopropoxycarbonylvaline
10-19. N-t-butoxycarbonylvaline
10-20. N-pentyloxycarbonylvaline
10-21. N-benzyloxycarbonylvaline
10-22. N-(p-tolylacetyl)valine
10-23. N-benzoylglycylvaline
10-24. N-(p-toluoyl)glycylvaline
10-25. N-(1-naphthoyl)glycylvaline
10-26. N-cyclopentanecarbonylglycylvaline
10-27. N-butoxycarbonylglycylvaline
10-28. N-octanoylalanylvaline
10-29. N-benzylalanylvaline 10-30. N-(p-toluoyl)alanylvaline
10-31. N-(4-aminobenzoyl)alanylvaline
10-32. N-(1-naphthoyl)alanylvaline
10-33. N-cyclohexanecarbonylalanylvaline
10-34. N-phenylacetylalanylvaline
10-35. N-benzyloxycarbonylalanylvaline
10-36. N-benzoylleucylvaline
10-37. N-benzoylglycylalanylvaline
10-38. N-(p-toluoyl)glycylalanylvaline
10-39. N-(1-naphthoyl)glycylalanylvaline
10-40. N-cyclopentanecarbonylglycylalanylvaline
10-41. N-butoxycarbonylglycylalanylvaline
10-42. N-benzyloxycarbonylglycylalanylvaline
10-43. N-(N-methylnicotinoyl)valine
10-44. N-(3-fluorobenzoyl)valine
10-45. N-benzoylvaline 11. Leucine derivatives.
11-1. N-butyrylleucine
11-2. N-isovalerylleucine
11-3. N-benzoylleucine
11-4. N-(4-butylbenzoyl)leucine
11-5. N-(2-hydroxybenzoyl)leucine
11-6. N-(3-sulfobenzoyl)leucine
11-7. N-cyclopentanecarbonylleucine
11-8. N-cyclohexanecarbonylleucine
11-9. N-(1-phenyl-1-cyclopropanecarbonyl)leucine
11-10. N-phenylacetylleucine
11-11. N-nicotinoylleucine
11-12. N-ethoxycarbonylleucine
11-13. N-benzyloxycarbonylleucine
11-14. N-(4-hydroxyphenylacetyl)leucine
11-15. N-benzoylvalylleucine
11-16. N-ethoxycarbonylvalylleucine
11-17. N-benzoylphenylalanylleucine
11-18. N-phenylacetylphenylalanylleucine
11-19. N-benzyloxycarbonylphenylalanylleucine
11-20. N-benzoylhistidylleucine
11-21. N-(p-toluoyl)histidylleucine
11-22. N-(4-hydroxybenzoyl)histidylleucine
11-23. N-(1-naphthoyl)histidylleucine
11-24. N-benzoylglycylphenylalanylleucine
11-25. N-(4-methoxybenzoyl)glycylphenylalanylleucine
11-26. N-phenylacetylglycylphenylalanylleucine
11-27. N-t-butoxycarbonylleucine 12. Isoleucine derivatives.
12-1. N-valerylisoleucine
12-2. N-pivaloylisoleucine
12-3. N-octanoylisoleucine
12-4. N-benzoylisoleucine
12-5. N-(3-hydroxybenzoyl)isoleucine
12-6. N-cyclopentanecarbonylisoleucine
12-7. N-cyclohexanecarbonylisoleucine
12-8. N-(1-phenyl-1-cyclopentanecarbonyl)isoleucine
12-9. N-phenylacetylisoleucine
12-10. N-methoxycarbonylisoleucine
12-11. N-propoxycarbonylisoleucine
12-12. N-isopropoxycarbonylisoleucine
12-13. N-benzyloxycarbonylisoleucine 13. Norleucine derivatives.
13-1. N-propionylnorleucine
13-2. N-valerylnorleucine
13-3. N-pivaloylnorleucine
13-4. N-nonanoylnorleucine
13-5. N-benzoylnorleucine
13-6. N-(4-hydroxybenzoyl)norleucine
13-7. N-cyclohexanecarbonylnorleucine
13-8. N-(1-phenyl-1-cyclopropanecarbonyl)norleucine
13-9. N-($\alpha$-phenyl-$\alpha$-ethylacetyl)norleucine
13-10. N-ethoxycarbonylnorleucine
13-11. N-propoxycarbonylnorleucine
13-12. N-t-butoxycarbonylnorleucine
13-13. N-benzyloxycarbonylnorleucine 14. Ornithine derivatives.
14-1$\alpha/\delta$. N-Acetylornithine
14-2$\alpha/\delta$. N-Propionylornithine
14-3$\alpha/\delta$. N-Butyrylornithine
14-4$\alpha/\delta$. N-Isobutyrylornithine
14-5$\alpha/\delta$. N-Valerylornithine
14-6$\alpha/\delta$. N-Hexanoylornithine
14-7$\alpha/\delta$. N-Heptanoylornithine
14-8$\alpha/\delta$. N-Octanoylornithine
14-9$\alpha/\delta$. N-Nonanoylornithine
14-10$\alpha/\delta$. N-Decanoylornithine
14-11$\alpha/\delta$. N-Crotonoylornithine
14-12$\alpha/\delta$. N-Benzoylornithine
14-13$\alpha/\delta$. N-Cyclopropanecarbonylornithine
14-14$\alpha/\delta$. N-Cyclohexanecarbonylornithine
14-15. $N^{\alpha},N^{\delta}$-Diacetylornithine
14-16. $N^{\alpha},N^{\delta}$-Dipropionylornithine
14-17. $N^{\alpha},N^{\delta}$-Dibutyrylornithine
14-18. $N^{\alpha},N^{\delta}$-Diisobutyrylornithine
14-19. $N^{\alpha},N^{\delta}$-Divalerylornithine
14-20. $N^{\alpha},N^{\delta}$-Diisovalerylornithine
14-21. $N^{\alpha},N^{\delta}$-Dihexanoylornithine
14-22. $N^{\alpha},N^{\delta}$-Diheptanoylornithine
14-23. $N^{\alpha},N^{\delta}$-Dioctanoylornithine
14-24. $N^{\alpha},N^{\delta}$-Dinonanoylornithine
14-25. $N^{\alpha},N^{\delta}$-Didecanoylornithine
14-26. $N^{\alpha},N^{\delta}$-Dicrotonoylornithine
14-27. $N^{\alpha},N^{\delta}$-Dibenzoylornithine
14-28. $N^{\alpha},N^{\delta}$-Dicyclopropanecarbonylornithine
14-29. $N^{\alpha},N^{\delta}$-Dicyclohexanecarbonylornithine
14-30. $N^{\alpha}$-Isobutyryl-$N^{\delta}$-benzoylornithine
14-31. $N^{\alpha}$-Crotonoyl-$N^{\delta}$-benzoylornithine
14-32. $N^{\alpha}$-Cyclopropanecarbonyl-$N^{\delta}$-isobutyrylornithine
14-33. $N^{\alpha}$-Cyclohexanecarbonyl-$N^{\delta}$-crotonoylornithine
14-34. $N^{\alpha}$-Benzoyl-$N^{\delta}$-isobutyrylornithine
14-35. $N^{\alpha}$-Benzoyl-$N^{\delta}$-crotonoylornithine
14-36. $N^{\alpha}$-Benzoyl-$N^{\delta}$-cyclopropanecarbonylornithine
14-37. $N^{\alpha}$-Benzoyl-$N^{\delta}$-cyclohexanecarbonylornithine
14-38. $N^{\alpha}$-Benzoyl-$N^{\delta}$-acetylornithine
14-39. $N^{\alpha}$-Benzoyl-$N^{\delta}$-propionylornithine
14-40$\alpha/\delta$. N-Methoxycarbonylornithine
14-41$\alpha/\delta$. N-Ethoxycarbonylornithine
14-42$\alpha/\delta$. N-Butoxycarbonylornithine
14-43. $N^{\alpha},N^{\delta}$-Dimethoxycarbonylornithine
14-44. $N^{\alpha},N^{\delta}$-Diethoxycarbonylornithine
14-45. $N^{\alpha},N^{\delta}$-Dibutoxycarbonylornithine
14-46. $N^{\alpha}$-Methoxycarbonyl-$N^{\delta}$-ethoxycarbonylornithine
14-47. $N^{\alpha}$-Methoxycarbonyl-$N^{\delta}$-butoxycarbonylornithine
14-48. $N^{\alpha}$-Ethoxycarbonyl-$N^{\delta}$-methoxycarbonylornithine
14-49. $N^{\alpha}$-Butoxycarbonyl-$N^{\delta}$-ethoxycarbonylornithine
14-50. $N^{\alpha}$-Ethoxycarbonyl-$N^{\delta}$-butoxycarbonylornithine
14-51. $N^{\alpha}$-Ethoxycarbonyl-$N^{\delta}$-crotonoylornithine 14-52. N$^\alpha$-Ethoxycarbonyl-N$^\delta$-cyclopropanecarbonylornithine
14-53. N$^\alpha$-Ethoxycarbonyl-N$^\delta$-benzoylornithine
14-54. N$^\alpha$-Propionyl-N$^\delta$-ethoxycarbonylornithine
14-55. N$^\alpha$-Benzoyl-N$^\delta$-ethoxycarbonylornithine
14-56$\alpha/\delta$. N-(4-Hydroxybenzoyl)ornithine
14-57$\alpha/\delta$. N-Anisoylornithine
14-58$\alpha/\delta$. N-(4-Aminobenzoyl)ornithine
14-59$\alpha/\delta$. N-Naphthoylornithine
14-60$\alpha/\delta$. N-(4-Sulfonylbenzoyl)ornithine
14-61$\alpha/\delta$. N-Toluoylornithine
14-62$\alpha/\delta$. N-Benzyloxycarbonylornithine
14-63$\alpha/\delta$. N-(4-Methoxybenzyloxycarbonyl)ornithine
14-64. N$^\alpha$,N$^\delta$-Di(4-hydroxybenzoyl)ornithine
14-65. N$^\alpha$,N$^\delta$-Dianisoylornithine
14-66. N$^\alpha$,N$^\delta$-Di(4-aminobenzoyl)ornithine
14-67. N$^\alpha$,N$^\delta$-Dinaphthoylornithine
14-68. N$^\alpha$-Cyclohexanecarbonyl-N$^\delta$-acetylornithine
14-69. N$^\alpha$,N$^\delta$-Ditoluoylornithine
14-70. N$^\alpha$,N$^\delta$-Dibenzyloxycarbonylornithine
24-71. N$^\alpha$,N$^\delta$-Di(4-methoxybenzyloxycarbonyl)ornithine 15. Lysine derivatives.
15-1$\alpha/\epsilon$. N-Acetyllysine
15-2$\alpha/\epsilon$. N-Propionyllysine
15-3$\alpha/\epsilon$. N-Butyryllysine
15-4$\alpha/\epsilon$. N-Isobutyryllysine
15-5$\alpha/\epsilon$. N-Valeryllysine
15-6$\alpha/\epsilon$. N-Hexanoyllysine
15-7$\alpha/\epsilon$. N-Heptanoyllysine
15-8$\alpha/\epsilon$. N-Octanoyllysine
15-9$\alpha/\epsilon$. N-Nonanoyllysine
15-10$\alpha/\epsilon$. N-Decanoyllysine
15-11$\alpha/\epsilon$. N-Crotonoyllysine
15-12$\alpha/\epsilon$. N-Benzoyllysine
15-13$\alpha/\epsilon$. N-Cyclopropanecarbonyllysine
15-14$\alpha/\epsilon$. N-Cyclohexanecarbonyllysine
15-15. N$^\alpha$,N$^\epsilon$-Diacetyllysine
15-16. N$^\alpha$,N$^\epsilon$-Dipropionyllysine
15-17. N$^\alpha$,N$^\epsilon$-Dibutyryllysine
15-18. N$^\alpha$,N$^\epsilon$-Diisobutyryllysine
15-19. N$^\alpha$,N$^\epsilon$-Divaleryllysine
15-20. N$^\alpha$,N$^\epsilon$-Diisovaleryllysine
15-21. N$^\alpha$,N$^\epsilon$-Dihexanoyllysine
15-22. N$^\alpha$,N$^\epsilon$-Diheptanoyllysine
15-23. N$^\alpha$,N$^\epsilon$-Dioctanoyllysine
15-24. N$^\alpha$,N$^\epsilon$-Dinonanoyllysine
15-25. N$^\alpha$,N$^\epsilon$-Didecanoyllysine
15-26. N$^\alpha$,N$^\epsilon$-Dicrotonoyllysine
15-27. N$^\alpha$,N$^\epsilon$-Dibenzoyllysine
15-28. N$^\alpha$,N$^\epsilon$-Dicyclopropanecarbonyllysine
15-29. N$^\alpha$,N$^\epsilon$-Dicyclohexanecarbonyllysine
15-30. N$^\alpha$-Isobutyryl-N$^\epsilon$-crotonoyllysine
15-31. N$^\alpha$-Isobutyryl-N$^\epsilon$-benzoyllysine
15-32. N$^\alpha$-Crotonoyl-N$^\epsilon$-benzoyllysine
15-33. N$^\alpha$-Cyclopropanecarbonyl-N$^\epsilon$-isobutyryllysine
15-34. N$^\alpha$-Cyclohexanecarbonyl-N$^\epsilon$-crotonoyllysine
15-35. N$^\alpha$-Cyclopropanecarbonyl-N$^\epsilon$-cyclohexanecarbonyllysine
15-36. N$^\alpha$-Cyclohexanecarbonyl-N$^\epsilon$-benzoyllysine
15-37. N$^\alpha$-Benzoyl-N$^\epsilon$-isobutyryllysine
15-38. N$^\alpha$-Benzoyl-N$^\epsilon$-crotonoyllysine
15-39. N$^\alpha$-Benzoyl-N$^\epsilon$-cyclopropanecarbonyllysine
15-40. N$^\alpha$-Benzoyl-N$^\epsilon$-cyclohexanecarbonyllysine
15-41. N$^\alpha$-Benzoyl-N$^\epsilon$-acetyllysine
15-42. N$^\alpha$-Benzoyl-N$^\epsilon$-propionyllysine
15-43. N-Methoxycarbonyllysine
15-44. N-Ethoxycarbonyllysine
15-45. N-Butoxycarbonyllysine
15-46. N$^\alpha$,N$^\epsilon$-Dimethoxycarbonyllysine
15-47. N$^\alpha$,N$^\epsilon$-Diethoxycarbonyllysine
15-48. N$^\alpha$,N$^\epsilon$-Dibutoxycarbonyllysine
15-49. N$^\alpha$-Methoxycarbonyl-N$^\epsilon$-ethoxycarbonyllysine
15-50. N$^\alpha$-Methoxycarbonyl-N$^\epsilon$-butoxycarbonyllysine
15-51. N$^\alpha$-Ethoxycarbonyl-N$^\epsilon$-methoxycarbonyllysine
15-52. N$^\alpha$-Butoxycarbonyl-N$^\epsilon$-ethoxycarbonyllysine
15-53. N$^\alpha$-Ethoxycarbonyl-N$^\epsilon$-propionyllysine
15-54. N$^\alpha$-Ethoxycarbonyl-N$^\epsilon$-crotonoyllysine
15-55. N$^\alpha$-Ethoxycarbonyl-N$^\epsilon$-cyclohexanecarbonyllysine
15-56. N$^\alpha$-Ethoxycarbonyl-N$^\epsilon$-benzoyllysine
15-57. N$^\alpha$-Isobutyryl-N$^\epsilon$-ethoxycarbonyllysine
15-58. N$^\alpha$-Benzoyl-N$^\epsilon$-ethoxycarbonyllysine
15-59$\alpha/\epsilon$. N-(4-Hydroxybenzoyl)lysine
15-60$\alpha/\epsilon$. N-Anisoyllysine
15-61$\alpha/\epsilon$. N-(4-Aminobenzoyl)lysine
15-62$\alpha/\epsilon$. N-Naphthoyllysine
15-63$\alpha/\epsilon$. N-(4-Sulfonylbenzoyl)lysine
15-64$\alpha/\epsilon$. N-Toluoyllysine
15-65$\alpha/\epsilon$. N-Benzyloxycarbonyllysine
15-66$\alpha/\epsilon$. N-(4-Methoxybenzyloxycarbonyl)lysine
15-67. N$^\alpha$,N$^\epsilon$-Di(4-hydroxybenzoyl)lysine
15-68. N$^\alpha$,N$^\epsilon$-Dianisoyllysine
15-69. N$^\alpha$,N$^\epsilon$-Di(4-aminobenzoyl)lysine
15-70. N$^\alpha$,N$^\epsilon$-Dinaphthoyllysine
15-71. N$^\alpha$-Cyclohexanecarbonyl-N$^\epsilon$-acetyllysine
15-72. N$^\alpha$,N$^\epsilon$-Ditoluoyllysine
15-73. N$^\alpha$,N$^\epsilon$-Dibenzyloxycarbonyllysine
15-74. N$^\alpha$,N$^\epsilon$-Di(4-methoxybenzyloxycarbonyl)lysine 16. Phenylalanine derivatives.
16-1. N-Acetylphenylalanine
16-2. N-Benzoylphenylalanine
16-3. N-(4-methoxybenzoyl)phenylalanine
16-4. N-cyclopropanecarbonylphenylalanine
16-5. N-Propionylphenylalanine
16-6. N-Butyrylphenylalanine
16-7. N-Isobutyrylphenylalanine
16-8. N-Valerylphenylalanine
16-9. N-Hexanoylphenylalanine
16-10. N-Heptanoylphenylalanine
16-11. N-Octanoylphenylalanine
16-12. N-Nonanoylphenylalanine
16-13. N-Decanoylphenylalanine
16-14. N-Crotonoylphenylalanine
16-15. N-Cyclopropanecarbonylphenylalanine
16-16. N-Cyclohexanecarbonylphenylalanine
16-17. N-Methoxycarbonylphenylalanine
16-18. N-Ethoxycarbonylphenylalanine
16-19. N-Butoxycarbonylphenylalanine
16-20. N-(4-Hydroxybenzoyl)phenylalanine
16-21. N-(4-Sulfobenzoyl)phenylalanine
16-22. N-(4-Aminobenzoyl)phenylalanine
16-23. N-(1-Naphthoyl)phenylalanine
16-24. N-Anisoylphenylalanine
16-25. N-(p-Toluoyl)phenylalanine
16-26. N-Benzyloxycarbonylphenylalanine
16-27. N-(4-Methoxybenzyloxycarbonyl)phenylalanine 16-28. N-nicotinoylphenylalanine
16-29. N-(2-thiophenecarbonyl)phenylalanine
16-30. N-(2-furoyl)phenylalanine
16-31. N-benzoylglycylphenylalanine
16-32. N-(4-hydroxybenzoyl)glycylphenylalanine
16-33. N-(1-naphthoyl)glycylphenylalanine
16-34. N-ethoxycarbonylglycylphenylalanine
16-35. N-benzyloxycarbonylglycylphenylalanine
16-36. N-benzoylalanylphenylalanine
16-37. N-(p-toluoyl)alanylphenylalanine
16-38. N-(4-hydroxybenzoyl)alanylphenylalanine
16-39. N-(4-aminobenzoyl)alanylphenylalanine
16-40. N-(1-naphthoyl)alanylphenylalanine
16-41. N-benzyloxycarbonylalanylphenylalanine
16-42. N-benzoylleucylphenylalanine
16-43. N-(4-hydroxybenzoyl)leucylphenylalanine
16-44. N-cyclohexanecarbonylleucylphenylalanine
16-45. N-benzyloxycarbonylleucylphenylalanine 17. Phenylglycine derivatives.
    17-1. N-Acetylphenylglycine
    17-2. N-Benzoylphenylglycine
    17-3. N-Propionylphenylglycine
    17-4. N-Butyrylphenylglycine
    17-5. N-Isobutyrylphenylglycine
    17-6. N-Valerylphenylglycine
    17-7. N-Hexanoylphenylglycine
    17-8. N-Heptanoylphenylglycine
    17-9. N-Octanoylphenylglycine
    17-10. N-Nonanoylphenylglycine
    17-11. N-Decanoylphenylglycine
    17-12. N-Crotonoylphenylglycine
    17-13. N-Cyclopropanecarbonylphenylglycine
    17-14. N-Cyclohexanecarbonylphenylglycine
    17-15. N-Methoxycarbonylphenylglycine
    17-16. N-Ethoxycarbonylphenylglycine
    17-17. N-Butoxycarbonylphenylglycine
    17-18. N-(4-Hydroxybenzoyl)phenylglycine
    17-19. N-Anisoylphenylglycine
    17-20. N-(4-Aminobenzoyl)phenylglycine
    17-21. N-(1-Naphthoyl)phenylglycine
    17-22. N-(4-Sulfobenzoyl)phenylglycine
    17-23. N-(p-Toluoyl)phenylglycine
    17-24. N-Benzyloxycarbonylphenylglycine
    17-25. N-(4-Methoxybenzyloxycarbonyl)phenylglycine
    17-26. N-(4-methoxybenzoyl)phenylglycine
    17-27. N-nicotinoylphenylglycine
    17-28. N-(2-thiophenecarbonyl)phenylglycine
    17-29. N-(2-furoyl)phenylglycine
    17-30. N-(4-chlorobenzoyl)phenylglycine 18. Tyrosine derivatives.
    18-1. N-benzoyltyrosine
    18-2. N-(3-methoxybenzoyl)tyrosine
    18-3. N-cyclohexanecarbonyltyrosine
    18-4. N-benzyloxycarbonyltyrosine
    18-5. N-phenethyloxycarbonyltyrosine 19. O-Methyltyrosine derivatives.
    19-1. N-acetyl-O-methyltyrosine
    19-2. N-propioloyl-O-methyltyrosine
    19-3. N-benzoyl-O-methyltyrosine
    19-4. N-(4-aminobenzoyl)-O-methyltyrosine
    19-5. N-(1-phenyl-1-cyclopentanecarbonyl)-O-methyltyrosine
    19-6. N-(1-phenyl-1-cyclohexanecarbonyl)-O-methyltyrosine
    19-7. N-methoxycarbonyl-O-methyltyrosine
    19-8. N-benzyloxycarbonyl-O-methyltyrosine
    19-9. N-phenethyloxycarbonyl-O-methyltyrosine 20. Aspartic acid derivatives.
    20-1. N-heptanoylaspartic acid
    20-2. N-decanoylaspartic acid
    20-3. N-(4-hydroxybenzoyl)aspartic acid
    20-4. N-(3-hydroxy-2-napthoyl)aspartic acid
    20-5. N-(1-phenyl-1-cyclopentanecarbonyl)aspartic acid
    20-6. N-(1-phenyl-1-cyclohexanecarbonyl)aspartic acid
    20-7. N-benzyloxycarbonylaspartic acid
    20-8. N-(4-methoxybenzyloxycarbonyl)aspartic acid 21. Glutamic acid derivatives.
    21-1. N-nonanoylglutamic acid
    21-2. N-(4-methoxybenzoy)glutamic acid
    21-3. N-(1-naphthoyl)glutamic acid
    21-4. N-(1-phenyl-1-cyclopentanecarbonyl)glutamic acid
    21-5. N-benzyloxycarbonylglutamic acid
    21-6. N-benzoylglutamic acid 22. 4-Carboxyglutamic acid derivatives.
    22-1. N-heptanoyl-4-carboxyglutamic acid
    22-2. N-(4-methoxybenzoyl)-4-carboxyglutamic acid
    22-3. N-(1-naphthoyl)-4-carboxyglutamic acid
    22-4. N-(1-hydroxy-2-naphthoyl)-4-carboxyglutamic acid
    22-5. N-phenylacetyl-4-carboxyglutamic acid 23. 3-Methylaspartic acid derivatives.
    23-1. N-octanoyl-3-methylaspartic acid
    23-2. N-(4-methoxybenzoyl)-3-methylaspartic acid
    23-3. N-(α-phenyl-α-cyclopentylacetyl)-3-methylaspartic acid 24. 2-Aminoadipic acid derivatives.
    24-1. N-hexanoyl-2-aminoadipic acid
    24-2. N-benzoyl-2-aminoadipic acid
    24-3. N-(p-toluoyl)-2-aminoadipic acid
    24-4. N-(1-naphthoyl)-2-aminoadipic acid
    24-5. N-(4-phenylbutyryl)-2-aminoadipic acid
    24-6. N-phenylacetyl-2-aminoadipic acid
    24-7. N-ethoxycarbonyl-2-aminoadipic acid 25. 2-Aminopimelic acid derivatives.
    25-1. N-valeryl-2-aminopimelic acid
    25-2. N-benzoyl-2-aminopimelic acid
    25-3. N-(3-phenylpropionyl)-2-aminopimelic acid
    25-4. N-methoxycarbonyl-2-aminopimelic acid
    25-5. N-ethoxycarbonyl-2-aminopimelic acid
    25-6. N-benzyloxycarbonyl-2-aminopimelic acid 26. 2-Aminosuberic acid derivatives.
    26-1. N-butyryl-2-aminosuberic acid
    26-2. N-benzoyl-2-aminosuberic acid
    26-3. N-(1-naphthoyl)-2-aminosuberic acid
    26-4. N-(α-phenyl-α-cyclopentylacetyl)-2-aminosuberic acid
    26-5. N-methoxycarbonyl-2-aminosuberic acid
    26-6. N-propoxycarbonyl-2-aminosuberic acid 27. 3-Hydroxyaspartic acid derivatives.
    27-1. N-(1-naphthoyl)-3-hydroxyaspartic acid
    27-2. N-(1-phenyl-1-cyclohexanecarbonyl)-3-hydroxyaspartic acid
    27-3. N-(α-phenyl-α-ethylacetyl)-3-hydroxyaspartic acid 28. 3-Hydroxyglutamic acid derivatives.
    28-1. N-(1-naphthoyl)-3-hydroxyglutamic acid
    28-2. N-(1-phenyl-1-cyclohexanecarbonyl)-3-hydroxyglutamic acid
    28-3. N-(α,α-diphenylacetyl)-3-hydroxyglutamic acid 29. 2,3-Diaminopropionic acid derivatives.

29-1. N^α-hexanoyl-2,3-diaminopropionic acid
29-2. N^α-(4-butylbenzoy)-2,3-diaminopropionic acid
29-3. N^α,N^β-dibenzoyl-2,3-diaminopropionic acid
29-4. N^α-(1-phenyl-1-cyclopentanecarbonyl)-2,3-diaminopropionic acid
29-5. N^α-(α-phenyl-α-ethylacetyl)-2,3-diaminopropionic acid
30. 2,4-Diaminobutyric acid derivatives.
  30-1. N^α-(1-naphthoyl)-2,4-diaminobutyric acid
  30-2. N^α,N^γ-dibenzoyl-2,4-diaminobutyric acid
  30-3. N^α-(1-phenyl-1-cyclopentanecarbonyl)-2,4-diaminobutyric acid
  30-4. N^α-(α-phenyl-α-ethylacetyl)-2,4-diaminobutyric acid
31. 5-Hydroxylysine derivatives.
  31-1. N^α-(p-toluoyl)-5-hydroxylysine
  31-2. N^α,N^δ-dibenzoyl-5-hydroxylysine
  31-3. N^α-(1-phenyl-1-cyclopentanecarbonyl)-5-hydroxylysine
  31-4. N^α-(α-phenyl-α-cyclopentylacetyl)-5-hydroxylysine
  31-5. N^α-(1-phenyl-1-cyclopentanecarbonyl)-5-hydroxylysine
32. Arginine derivatives.
  32-1. N^α-heptanoylarginine
  32-2. N^α-(2-methoxybenzoyl)arginine
33. N^δ,N^δ-Dimethylornithine derivatives.
  33-1. N^α-pivaloyl-N^δ,N^δ-dimethylornithine
  33-2. N^α-octanoyl-N^δ,N^δ-dimethylornithine
  33-3. N^α-acryloyl-N^δ,N^δ-dimethylornithine
  33-4. N^α-benzoyl-N^δ,N^δ-dimethylornithine
  33-5. N^α-(4-hydroxybenzoyl)-N^δ,N^δ-dimethylornithine
  33-6. N^α-cyclohexanecarbonyl-N^δ,N^δ-dimethylornithine
  33-7. N^α-(α-phenyl-α-methylacetyl)-N^δ,N^δ-dimethylornithine
  33-8. N^α-ethoxycarbonyl-N^δ,N^δ-dimethylornithine
  33-9. N^α-butoxycarbonyl-N^δ,N^δ-dimethylornithine
  33-10. N^α-benzyloxycarbonyl-N^δ,N^δ-dimethylornithine
34. N^ε-Methyllysine derivatives.
  34-1. N^α-hexanoyl-N^ε-methyllysine
  34-2. N^α-nonanoyl-N^ε-methyllysine
  34-3. N^α-acryloyl-N^ε-methyllysine
  34-4. N^α-benzoyl-N^ε-methyllysine
  34-5. N^α-(4-butoxybenzoyl)-N^ε-methyllysine
  34-6. N^α-(3-sulfobenzoyl)-N^ε-methyllysine
  34-7. N^α-cyclobutanecarbonyl-N^ε-methyllysine
  34-8. N^α-cyclohexanecarbonyl-N^ε-methyllysine
  34-9. N^α-phenylacetyl-N^ε-methyllysine
  34-10. N^α-propoxycarbonyl-N^ε-methyllysine
  34-11. N^α-isopropoxycarbonyl-N^ε-methyllysine
  34-12. N^α-benzyloxycarbonyl-N^ε-methyllysine
35. Cysteine derivatives.
  35-1. N-phenylacetylcysteine
36. Methionine derivatives.
  36-1. N-valerylmethionine
  36-2. N-acryloylmethionine
  36-3. N-methacryloylmethionine
  36-4. N-benzoylmethionine
  36-5. N-(p-toluoyl)methionine
  36-6. N-(4-methoxybenzoyl)methionine
  36-7. N-(4-aminobenzoyl)methionine
  36-8. N-cyclopentanecarbonylmethionine
  36-9. N-cyclohexanecarbonylmethionine
  36-10. N-(1-phenyl-1-cyclohexanecarbonyl)methionine
  36-11. N-phenylacetylmethionine
  36-12. N-(α-phenyl-α-methylacetyl)methionine
  36-13. N-methoxycarbonylmethionine
  36-14. N-ethoxycarbonylmethionine
  36-15. N-butoxycarbonylmethionine
  36-16. N-benzyloxycarbonylmethionine
  36-17. N-(4-methylbenzyloxycarbonyl)methionine
  36-18. N-benzoylglycylmethionine
  36-19. N-(4-methoxybenzoyl)glycylmethionine
  36-20. N-benzyloxycarbonylglycylmethionine
  36-21. N-benzoylvalylmethionine
  36-22. N-cyclopentanecarbonylvalylmethionine
  36-23. N-ethoxycarbonylvalylmethionine
37. Ethionine derivatives.
  37-1. N-butyrylethionine
  37-2. N-benzoylethionine
  37-3. N-(p-toluoyl)ethionine
  37-4. N-(m-toluoyl)ethionine
  37-5. N-(4-butylbenzoyl)ethionine
  37-6. N-(4-hydroxybenzoyl)ethionine
  37-7. N-(4-aminobenzoyl)ethionine
  37-8. N-(3-sulfobenzoyl)ethionine
  37-9. N-(1-phenyl-1-cyclopropanecarbonyl)ethionine
  37-10. N-phenylacetylethionine
  37-11. N-methoxycarbonylethionine
  37-12. N-ethoxycarbonylethionine
  37-13. N-benzyloxycarbonylethionine
  37-14. N-(4-methoxybenzyloxycarbonyl)ethionine
  37-15. N-cyclohexanecarbonylethionine
38. S-Carboxymethylcysteine derivatives.
  38-1. N-propionyl-S-carboxymethylcysteine
  38-2. N-acryloyl-S-carboxymethylcysteine
  38-3. N-benzoyl-S-carboxymethylcysteine
  38-4. N-(p-toluoyl)-S-carboxymethylcysteine
  38-5. N-(4-methoxybenzoyl)-S-carboxymethylcysteine
  38-6. N-(4-butoxybenzoy)-S-carboxymethylcysteine
  38-7. N-cyclohexanecarbonyl-S-carboxymethylcysteine
  38-8. N-(1-phenyl-1-cyclopentanecarbonyl)-S-carboxymethylcysteine
  38-9. N-(α-methylbenzyloxycarbonyl)-S-carboxymethylcysteine
39. S-Benzylcysteine derivatives.
  39-1. N-benzoyl-S-benzylcysteine
  39-2. N-(4-hydroxybenzoy)-S-benzylcysteine
  39-3. N-(3-sulfobenzoyl)-S-benzylcysteine
  39-4. N-cyclopropanecarbonyl-S-benzylcysteine
  39-5. N-methoxycarbonyl-S-benzylcysteine
  39-6. N-ethoxycarbonyl-S-benzylcysteine
  39-7. N-propoxycarbonyl-S-benzylcysteine
  39-8. N-(4-hydroxybenzyloxycarbonyl)-S-benzylcysteine
40. Methionine S-oxide derivatives.
  40-1. N-(p-toluoyl)methionine S-oxide
  40-2. N-pentyloxycarbonylmethionine S-oxide
  40-3. N-benzyloxycarbonylmethionine S-oxide
41. Ethionine S-oxide derivatives.
  41-1. N-benzoylethionine S-oxide
  41-2. N-benzyloxycarbonylethionine S-oxide
42. Methionine S,S-dioxide derivatives.
  42-1. N-(1-naphthoyl)methione S,S-dioxide
  42-2. N-cyclohexanecarbonylmethionine S,S-dioxide
  42-3. N-pentyloxycarbonylmethionine S,S-dioxide
43. Cysteic acid derivatives.

43-1. N-(p-toluoyl)cysteic acid
43-2. N-(1-naphthoyl)cysteic acid
43-3. N-(3-hydroxy-2-naphthoyl)cysteic acid
43-4. N-(1-phenyl-1-cyclohexanecarbonyl)cysteic acid
44. Serine derivatives.
　44-1. N-octanoylserine
　44-2. N-benzoylserine
　44-3. N-(m-toluoyl)serine
　44-4. N-(4-methoxybenzoyl)serine
　44-5. N-(1-naphthoyl)serine
　44-6. N-(1-phenyl-1-cyclopentanecarbonyl)serine
　44-7. N-benzyloxycarbonylserine
　44-8. N-(α-methylbenzyloxycarbonyl)serine
45. O-methylserine derivatives.
　45-1. N-valeryl-O-methylserine
　45-2. N-benzoyl-O-methylserine
　45-3. N-cyclohexanecarbonyl-O-methylserine
　45-4. N-phenylacetyl-O-methylserine
　45-5. N-(α-phenyl-α-methylacetyl)-O-methylserine
　45-6. N-(3-phenylpropionyl)-O-methylserine
　45-7. N-phenethyloxycarbonyl-O-methylserine
46. Threonine derivatives.
　46-1. N-hexanoylthreonine
　46-2. N-nonanoylthreonine
　46-3. N-benzoylthreonine
　46-4. N-(3-hydroxy-2-naphthoyl)threonine
　46-5. N-cyclohexanecarbonylthreonine
　46-6. N-(α,α-diphenylacetyl)threonine
　46-7. N-butoxycarbonylthreonine
　46-8. N-benzyloxycarbonylthreonine
　46-9. N-(4-methoxybenzyloxycarbonyl)threonine
47. O-Methylthreonine derivatives.
　47-1. N-butyryl-O-methylthreonine
　47-2. N-(4-methoxybenzoyl)-O-methylthreonine
　47-3. N-(1-naphthoyl)-O-methylthreonine
　47-4. N-(1-phenyl-1-cyclopentanecarbonyl)-O-methylthreonine
　47-5. N-ethoxycarbonyl-O-methylthreonine
　47-6. N-(3-phenylpropoxycarbonyl)-O-methylthreonine
48. Homoserine derivatives.
　48-1. N-heptanoylhomoserine
　48-2. N-benzoylhomoserine
　48-3. N-(3-methoxybenzoyl)homoserine
　48-4. N-(α-phenyl-α-cyclopentylacetyl)homoserine
　48-5. N-(4-hydroxybenzyloxycarbonyl)homoserine
　48-6. N-(4-methylbenzyloxycarbonyl)homoserine
49. Ethoxinine derivatives.
　49-1. N-benzoylethoxinine
　49-2. N-(4-butoxybenzoyl)ethoxinine
　49-3. N-cyclohexanecarbonylethoxinine
　49-4. N-methoxycarbonylethoxinine
50. 3-Methoxyvaline derivatives.
　50-1 N-isovaleryl-3-methoxyvaline
　50-2. N-(p-toluoyl)-3-methoxyvaline
　50-3. N-(1-naphthoyl)-3-methoxyvaline
　50-4. N-cyclopentanecarbonyl-3-methoxyvaline
　50-5. N-cyclohexanecarbonyl-3-methoxyvaline
　50-6. N-methoxycarbonyl-3-methoxyvaline
　50-7. N-ethoxycarbonyl-3-methoxyvaline
51. 3-Phenylserine derivatives.
　51-1. N-propionyl-3-phenylserine
　51-2. N-(4-aminobenzoyl)-3-phenylserine
　51-3. N-(1-naphthoyl)-3-phenylserine
　51-4. N-benzoyl-3-phenylserine
　51-5. N-cyclohexanecarbonyl-3-phenylserine
　51-6. N-phenylacetyl-3-phenylserine
　51-7. N-methoxycarbonyl-3-phenylserine
　51-8. N-butoxycarbonyl-3-phenylserine
　51-9. N-benzyloxycarbonyl-3-phenylserine
　51-10. N-(α-methylbenzyloxycarbonyl)-3-phenylserine
52. 3-Methyl-3-phenylalanine derivatives.
　52-1. N-acetyl-3-methyl-3-phenylalanine
　52-2. N-hexanoyl-3-methyl-3-phenylalanine
　52-3. N-benzoyl-3-methyl-3-phenylalanine
　52-4. N-(4-aminobenzoyl)-3-methyl-3-phenylalanine
　52-5. N-(3-sulfobenzoyl)-3-methyl-3-phenylalanine
　52-6. N-cyclobutanecarbonyl-3-methyl-3-phenylalanine
　52-7. N-cyclopentanecarbonyl-3-methyl-3-phenylalanine
　52-8. N-phenylacetyl-3-methyl-3-phenylalanine
　52-9. N-isopropoxycarbonyl-3-methyl-3-phenylalanine
　52-10. N-butoxycarbonyl-3-methyl-3-phenylalanine
　52-11. N-(4-aminobenzyloxycarbonyl)-3-methyl-3-phenylalanine
53. Histidine derivatives.
　53-1. N-acetylhistidine
　53-2. N-hexanoylhistidine
　53-3. N-acryloylhistidine
　53-4. N-methacryloylhistidine
　53-5. N-benzoylhistidine
　53-6. N-(p-toluoyl)histidine
　53-7. N-(4-methoxybenzoyl)histidine
　53-8. N-(4-butoxybenzoyl)histidine
　53-9. N-cyclopentanecarbonylhistidine
　53-10. N-cyclohexanecarbonylhistidine
　53-11. N-(1-phenyl-1-cyclopentanecarbonyl)histidine
　53-12. N-phenylacetylhistidine
　53-13. N-(α-phenyl-α-cyclopentylacetyl)histidine
　53-14. N-(4-methoxybenzyloxycarbonyl)histidine
　53-15. N-benzoylglycylhistidine
　53-16. N-(4-butylbenzoyl)glycylhistidine
　53-17. N-phenylacetylglycylhistidine
　53-18. N-ethoxycarbonylglycylhistidine
　53-19. N-benzyloxycarbonylglycylhistidine
　53-20. N-benzoylglycylglycylhistidine
　53-21. N-ethoxycarbonylglycylglycylhistidine
　53-22. N-benzyloxycarbonylglycylglycylhistidine
　53-23. N-t-butoxycarbonylhistidine
54. Tryptophan derivatives.
　54-1. N-(4-hydroxybenzoyl)tryptophan
　54-2. N-benzyloxycarbonyltryptophen
55. 2-Methylalanine derivatives.
　55-1. N-propionyl-2-methylalanine
　55-2. N-benzoyl-2-methylalanine
　55-3. N-(m-toluoyl)-2-methylalanine
　55-4. N-(3-methoxybenzoyl)-2-methylalanine
　55-5. N-cyclobutanecarbonyl-2-methylalanine
　55-6. N-phenylacetyl-2-methylalanine
　55-7. N-phenethyloxycarbonyl-2-methylalanine
56. 2-Methylserine derivatives.
　56-1. N-valeryl-2-methylserine
　56-2. N-octanoyl-2-methylserine
　56-3. N-benzoyl-2-methylserine
　56-4. N-(o-toluoyl)-2-methylserine
　56-5. N-(4-methoxybenzoyl)-2-methylserine
　56-6. N-(1-naphthoyl)-2-methylserine
　56-7. N-cyclopentanecarbonyl-2-methylserine
　56-8. N-(α,α-diphenylacetyl)-2-methylserine
　56-9. N-pentyloxycarbonyl-2-methylserine 57. 2-Hydroxyisoleucine derivatives.
   57-1. N-valeryl-2-hydroxyisoleucine
   57-2. N-heptanoyl-2-hydroxyisoleucine
   57-3. N-benzoyl-2-hydroxyisoleucine
   57-4. N-(4-butoxybenzoyl)-2-hydroxyisoleucine
   57-5. N-(3-hydroxy-2-naphthoyl)-2-hydroxyisoleucine
   57-6. N-cyclohexanecarbonyl-2-hydroxyisoleucine
   57-7. N-phenylacetyl-2-hydroxyisoleucine
58. 2-Methylmethionine derivatives.
   58-1 N-hexanoyl-2-methylmethionine
   58-2. N-benzoyl-2-methylmethionine
   58-3. N-(4-hydroxybenzoyl)-2-methylmethionine
   58-4. N-propoxycarbonyl-2-methylmethionine
   58-5. N-isopropoxycarbonyl-2-methylmethionine
59. 2-Ethyl-2-phenylglycine derivatives.
   59-1. N-acetyl-2-ethyl-2-phenylglycine
   59-2. N-butyryl-2-ethyl-2-phenylglycine
   59-3. N-(3-sulfobenzoyl)-2-ethyl-2-phenylglycine
   59-4. N-ethoxycarbonyl-2-ethyl-2-phenylglycine
   59-5. N-propoxycarbonyl-2-ethyl-2-phenylglycine
60. 3-Aminobutyric acid derivatives.
   60-1. N-hexanoyl-3-aminobutyric acid
   60-2. N-benzoyl-3-aminobutyric acid
   60-3. N-(4-methoxybenzoyl)-3-aminobutyric acid
   60-4. N-(3-sulfobenzoyl)-3-aminobutyric acid
   60-5. N-(1-naphthoyl)-3-aminobutyric acid
   60-6. N-cyclopropanecarbonyl-3-aminobutyric acid
   60-7. N-($\alpha$,$\alpha$-diphenylacetyl)-3-aminobutyric acid
   60-8. N-(4-phenylbutyl)-3-aminobutyric acid
   60-9. N-($\alpha$-methylbenzyloxycarbonyl)-3-aminobutyric acid
61. 3-Amino-4-methylvaleric acid derivatives.
   61-1. N-valeryl-3-amino-4-methylvaleric acid
   61-2. N-isovaleryl-3-amino-4-methylvaleric acid
   61-3. N-heptanoyl-3-amino-4-methylvaleric acid
   61-4. N-benzoyl-3-amino-4-methylvaleric acid
   61-5. N-(m-toluoyl)-3-amino-4-methylvaleric acid
   61-6. N-(3-sulfobenzyl)-3-amino-4-methylvaleric acid
   61-7. N-(1-naphthoyl)-3-amino-4-methylvaleric acid
   61-8. N-phenylacetyl-3-amino-4-methylvaleric acid
   61-9. N-(3-phenylpropionyl)-3-amino-4-methylvaleric acid
   61-10. N-butoxycarbonyl-3-amino-4-methylvaleric acid
   61-11. N-(4-methylbenzyloxycarbonyl)-3-amino-4-methylvaleric acid
62. 3-Amino-3-phenylpropionic acid derivatives.
   62-1. N-butyryl-3-amino-3-phenylpropionic acid
   62-2. N-valeryl-3-amino-3-phenylpropionic acid
   62-3. N-benzoyl-3-amino-3-phenylpropionic acid
   62-4. N-(4-aminobenzoyl)-3-amino-3-phenylpropionic acid
   62-5. N-cyclopropanecarbonyl-3-amino-3-phenylpropionic acid
   62-6. N-cyclobutanecarbonyl-3-amino-3-phenylpropionic acid
   62-7. N-cyclopentanecarbonyl-3-amino-3-phenylpropionic acid
   62-8. N-methoxycarbonyl-3-amino-3-phenylpropionic acid
   62-9. N-propoxycarbonyl-3-amino-3-phenylpropionic acid
   62-10. N-butoxycarbonyl-3-amino-3-phenylpropionic acid
   62-11. N-(4-aminobenzyloxycarbonyl)-3-amino-3-phenylpropionic acid
63. 3-Amino-2-hydroxypropionic acid derivatives.
   63-1. N-valeryl-3-amino-2-hydroxypropionic acid
   63-2. N-heptanoyl-3-amino-2-hydroxypropionic acid
   63-3. N-benzoyl-3-amino-2-hydroxypropionic acid
   63-4. N-(3-methoxybenzoyl)-3-amino-2-hydroxypropionic acid
   63-5. N-cyclohexanecarbonyl-3-amino-2-hydroxypropionic acid
   63-6. N-benzyloxycarbonyl-3-amino-2-hydroxypropionic acid
   63-7. N-(3-phenylpropoxycarbonyl)-3-amino-2-hydroxypropionic acid
64. 4-Amino-3-hydroxybutyric acid
   64-1. N-isobutyryl-4-amino-3-hydroxybutyric acid
   64-2. N-decanol-4-amino-3-hydroxybutyric acid
   64-3. N-benzoyl-4-amino-3-hydroxybutyric acid
   64-4. N-(o-toluoyl)-4-amino-3-hydroxybutyric acid
   64-5. N-(3-aminobenzoyl)-4-amino-3-hydroxybutyric acid
   64-6. N-(1-phenyl-1-cyclohexanecarbonyl)-4-amino-3-hydroxybutyric acid
   64-7. N-($\alpha$-phenyl-$\alpha$-methylacetyl)-4-amino-3-hydroxybutyric acid
   64-8. N-(4-methoxybenzyloxycarbonyl)-4-amino-3-hydroxybutyric acid Of the amino acid derivatives listed above, the following are particularly preferred: Compounds No. 2-5, 2-6, 2-7, 2-18, 2-22, 4-6, 5-11, 5-18, 5-33, 6-3, 7-3, 7-5, 7-14, 8-4, 9-3, 10-4, 10-29, 10-45, 11-3, 11-24, 13-5, 14-27, 14-28, 14-29, 14-37, 14-38, 14-68, 15-27, 15-28, 15-29, 15-40, 15-41, 15-68, 15-71, 16-2, 16-3, 16-9, 16-15, 16-16, 16-24, 16-31, 16-36, 16 -44, 17-2, 17-13, 17-14, 17-19, 17-26, 19-3, 36-4, 36-11, 36-21, 37-2, 37-14, 46-3, 53-5, 53-6, 53-7, 60-3 and 62-1. Of these, Compounds No. 2-22 and 10-45, especially No. 2-22, are most preferred.

The amino acid derivatives employed in the present invention are acids and, as such, are capable of forming salts; any pharmaceutically acceptable salt of these amino acids may be employed. Examples of such salts include: alkali metal salts such as the sodium or potassium salts; alkaline earth metal salts, such as the calcium salt; other metal salts, such as the magnesium, aluminum, iron, zinc, copper, nickel and cobalt salts; the ammonium salt; and salts with amino sugars, such as glucosamine and galactosamine.

The compositions of the invention may be prepared by any suitable method which involves mixing the antibiotic with the amino acid derivative and the invention is not intended to be limited by any particular method of preparation. Since the amino acid derivatives employed in this invention have, in general, very limited solubility in water, it is preferred that they should first be dispersed in water and then converted to a suitable salt by adding an aqueous solution of an appropriate base, for example: a metal compound, such as sodium hydroxide or potassium hydroxide, ammonia; or an amino sugar, such as glucosamine or galactosamine. Sufficient of the base is preferably added to adjust the pH of the mixture to a value within the range from 5.5 to 9, more preferably from 6 to 9.

The penem or carbapenem antibiotic is then added to the resulting solution. The mixed solution thus obtained may be employed as such or it may first be lyophilized to give a powdery mixture, which may be subsequently formulated into an appropriate dosage form suitable for the chosen route of administration, either by the manufacturer or prior to use.

The above mixing and preparation steps may take place at any temperature at which the components are fluid (especially the media) and are not decomposed, e.g. from 0° to 100° C., more conveniently from 0° to 50° C. and most conveniently at about ambient temperature.

Although it is convenient to administer the antibiotic and the amino acid derivative simultaneously in a single composition, it is, of course, clear that the two compounds may be administered separately, provided that they are administered sufficiently closely in time to each other that the amino acid derivative has a suitable concentration in the blood for all or most of the time that the antibiotic is present. Normally, it is anticipated that this will be achieved if the two compounds are administered within about one hour of each other, the amino acid preferably being administered before the antibiotic.

The composition of the invention is particularly suitable for use by intravenous administration.

There is no particular restriction on the relative proportions of the amino acid derivative and the penem or carbapenem antibiotic; in general, we have found that weight proportions of amino acid derivative to antibiotic of from 0.1:1 to 4:1 give good results, but equally proportions outside this range may successfully be employed. Approximately equal weights are generally most convenient.

The invention includes a method of treating a mammal suffering from a bacterial infection by administering to said mammal an antibiotic selected from the group consisting of penem antibiotics and carbapenem antibiotics capable of causing renal damage; and an effective amount of a pharmaceutically acceptable N-acylated derivative of an amino acid wherein the amino group and the carboxylic acid group are attached to a saturated aliphatic carbon chain or carbon atom, or a salt thereof wherein said effective amount is at least sufficient to reduce, alleviate or eliminate said renal damage. A preferred composition comprises (5R,6S)-2-[(3S)-1-acetimidoylpyrrolidin-3-ylthio]-6-[1(R)-hydroxyethyl]-2-carbapenem-3-carboxylic acid; and N-benzoyl-$\beta$-alanine. The weight ratio of said carbapenem to said alanine is from about 1:0.1 to 1:4 and preferably about 1:1.

The invention is further illustrated by the following Examples and Activity Tests. In the following, the penem or carbapenem antibiotics are referred to by the numbers appended to them in the foregoing list and are identified as "(Carba)-Penem Cpd No" whilst the amino acid derivatives are also identified by the numbers appended to them in the foregoing list and are referred to as "Amino Acid Cpd No."

EXAMPLE 1

5 g of $N^\alpha,N^\epsilon$-dibenzoyllysine (Amino Acid Compound No. 15-27) were weighed out and dispersed in 80 ml of water. A 1N aqueous solution of sodium hydroxide was slowly added to this dispersion, and dissolved the $N^\alpha,N^\epsilon$-dibenzoyllysine when the pH of the solution reached a value of 7-8. Then, 5 g of (5R,6S)-2-[(3S)-1-acetimidoylpyrrolidin-3-ylthio]-6-[1(R)-hydroxyethyl]-2-carbapenem-3-carboxylic acid (Carbapenem Compound No. 6) were dissolved in this solution, to give a total volume of 100 ml.

EXAMPLE 2

5 g of N-benzoyl-$\beta$-alanine (Amino Acid Compound No. 2-22) were weighed out and dispersed in 40 ml of water. A 1N aqueous solution of sodium hydroxide was slowly added to this dispersion, and dissolved the N-benzoyl-$\beta$-alanine when the pH of the solution reached a value of 7-8. Then, 5 g of (5R,6S)-2-[(3S)-1-acetimidoylpyrrolidin-3-ylthio]-6-[1(R)-hydroxyethyl]-2-carbapenem-3-carboxylic acid (Carbapenem Compound No. 6) were dissolved in this solution, to give a total volume of 50 ml.

EXAMPLE 3

Similar procedures to those described in Examples 1 and 2 were carried out, using the other penem or carbapenem antibiotic substances and the other acylated amino acid derivatives shown in the following Table, in the amounts shown in that Table.

In this Table, where the amino acid derivatives are not specified as being D- or L-, then they are the DL-form.

ACTIVITY TESTS

The preparation obtained by the procedure described in Example 1 was injected into the ear vein of a rabbit (about 3 kg body weight) in an amount of 3 ml/kg [that is 150 mg/kg of the carba penem Compound No. 6+150 mg/kg of $N^\alpha,N^\epsilon$-dibenzoyllysine (amino acid Compound No. 15-27)]. A preparation which had been obtained by the same procedure as that described in Example 1 but not including the $N^\alpha,N^\epsilon$-dibenzoyllysine was injected into another rabbit, as a control, in a similar manner to the above.

After one week, the kidneys of both rabbits were excised and examined. A change was observed in the renal tissue of the rabbits to which had been administered the preparation without the $N^\alpha,N^\epsilon$-dibenzoyllysine, but no such change at all was observed in the renal tissue of rabbits to which had been administered the preparation containing the $N^\alpha,N^\epsilon$-dibenzoyllysine.

Similar experiments were carried out on other preparations which were prepared from other penem or carbapenem antibiotic substances and other amino acid derivatives. The Table also shows the results of these experiments.

The observed change in the renal tissue of the control rabbits was a degenerative necrosis of the proximal renal tubules in the region of the renal cortex. In the following Table, where the proportion of the total area of this region which exhibited such necrosis was from 0 to 25%, this is shown as +++. Where the area is less than 50% this is shown as ++ and where it is less than 75% this is shown as +. Where different animals within each test group exhibited different responses, this is shown as e.g. +++—++ or ++—+.

It should be noted that, whenever penem or carbapenem antibiotic substances which were not combined with amino acid derivatives were administered, a change in the renal tissue was observed. Hence, all of the experiments carried out (even where the effect is only "+") demonstrated a significant protective effect of the amino acid derivative.

TABLE

| (Carba)-Penem Cpd. No. | Amount mg/kg | Amino Acid Cpd. No. | Amount mg/kg | Effect |
|---|---|---|---|---|
| 6 | 150 | 1-5 | 150 | + |
| 6 | 150 | 1-8 | 150 | ++ |
| 6 | 150 | 1-10 | 150 | + |
| 6 | 150 | 1-11 | 150 | ++ |
| 6 | 150 | 1-12 | 150 | + |
| 6 | 150 | 2-3 | 150 | ++ |
| 6 | 150 | 2-4 | 150 | ++ |
| 6 | 150 | 2-5 | 150 | +++ |
| 6 | 250 | 2-6 | 250 | +++ |
| 6 | 150 | 2-7 | 150 | +++ |
| 6 | 150 | 2-10 | 150 | ++ |
| 6 | 150 | 2-11 | 150 | ++ |
| 6 | 150 | 2-13 | 150 | ++ |
| 6 | 150 | 2-14 | 150 | ++ |
| 6 | 150 | 2-15 | 150 | ++ |
| 6 | 250 | 2-18 | 250 | +++ |
| 6 | 150 | 2-22 | 150 | +++ |
| 6 | 200 | 2-22 | 200 | +++ |
| 6 | 300 | 2-22 | 300 | +++ |
| 6 | 300 | 2-22 | 150 | ++ |
| 6 | 400 | 3-3 | 400 | +++ |
| 6 | 150 | 3-6 | 150 | + |
| 6 | 150 | 3-8 | 150 | + |
| 6 | 150 | 3-15 | 150 | + |
| 6 | 150 | 4-1 | 150 | + |
| 6 | 150 | 4-4 | 150 | + |
| 6 | 150 | 4-5 | 150 | ++ |
| 5 | 150 | 4-6 | 150 | +++ |
| 6 | 150 | 5-3 | 150 | ++ |
| 6 | 150 | 5-11 | 150 | ++ |
| 6 | 150 | 5-14 | 150 | + |
| 6 | 250 | 5-18 | 250 | ++ |
| 6 | 150 | 5-33 | 150 | +++ |
| 6 | 150 | 6-2 | 150 | ++ |
| 6 | 50 | 6-3 | 150 | +++ |
| 6 | 150 | 6-11 | 150 | ++ |
| 6 | 150 | 7-2 | 150 | + |
| 6 | 150 | 7-3 | 150 | +++ |
| 6 | 150 | 7-5 | 150 | +++ |
| 6 | 150 | 7-12 | 150 | ++ |
| 6 | 150 | 7-18 | 150 | ++ |
| 6 | 150 | 8-2 | 150 | + |
| 6 | 150 | 8-4 | 150 | +++ |
| 6 | 150 | 8-8 | 150 | ++ |
| 6 | 150 | 8-10 | 150 | + |
| 6 | 150 | 9-3 | 150 | +++ |
| 6 | 150 | 9-5 | 150 | + |
| 6 | 150 | 10-4 | 150 | +++ |
| 6 | 250 | 10-19 | 250 | ++ |
| 6 | 150 | 10-24 | 150 | + |
| 6 | 150 | 10-30 | 150 | + |
| 6 | 150 | 10-32 | 150 | + |
| 6 | 150 | 10-33 | 150 | + |
| 6 | 150 | 10-34 | 150 | ++ |
| 6 | 150 | 10-35 | 150 | ++ |
| 6 | 150 | 10-45 | 150 | +++ |
| 6 | 400 | 10-45 | 400 | +++ |
| 6 | 400 | 10-45 | 200 | ++ |
| 6 | 150 | 11-3 | 150 | +++ |
| 6 | 150 | 11-6 | 150 | + |
| 6 | 150 | 11-7 | 150 | + |
| 6 | 150 | 11-8 | 150 | + |
| 6 | 150 | 11-24 | 150 | +++ |
| 6 | 150 | 12-1 | 150 | ++ |
| 6 | 150 | 12-4 | 150 | ++ |
| 6 | 150 | 13-1 | 150 | ++ |
| 6 | 150 | 13-2 | 150 | ++ |
| 6 | 150 | 13-5 | 150 | +++ |
| 6 | 150 | 13-12 | 150 | + |
| 6 | 150 | 14-18 | 150 | ++-++ |
| 6 | 150 | 14-21 | 150 | ++-++ |
| 6 | 150 | 14-26 | 150 | ++-++ |
| 6 | 150 | 14-27 | 150 | +++ |
| 6 | 150 | 14-28 | 150 | +++ |
| 6 | 150 | 14-29 | 150 | +++ |
| 6 | 150 | 14-44 | 150 | ++-++ |
| 6 | 150 | 14-65 | 150 | ++ |
| 6 | 150 | 14-71 | 150 | + |
| 6 | 150 | 15-18 | 150 | ++-++ |
| 6 | 150 | 15-21 | 150 | ++-++ |
| 6 | 150 | 15-26 | 150 | ++-++ |
| 6 | 150 | 15-27 | 300 | +++ |
| 6 | 150 | 15-27 | 150 | +++ |
| 6 | 150 | 15-27 | 75 | +++ |
| 6 | 150 | 15-27 | 37.5 | ++-++ |
| 6 | 150 | L-15-27 | 150 | ++-++ |
| 6 | 150 | D-15-27 | 150 | +++ |
| 6 | 150 | 15-28 | 150 | ++-++ |
| 6 | 150 | 15-29 | 150 | +++ |
| 6 | 150 | D-15-29 | 150 | +++ |
| 6 | 150 | 15-30 | 150 | ++-++ |
| 6 | 150 | 15-35 | 150 | ++-++ |
| 6 | 150 | 15-36 | 150 | ++-++ |
| 6 | 150 | 15-42 | 150 | ++-++ |
| 6 | 150 | 15-47 | 150 | ++-++ |
| 6 | 150 | 15-55α | 150 | ++-++ |
| 6 | 150 | 15-67 | 150 | ++ |
| 6 | 150 | 15-68 | 150 | +++ |
| 6 | 150 | 15-69 | 150 | ++ |
| 6 | 150 | 15-70 | 150 | + |
| 6 | 150 | 15-72 | 150 | ++ |
| 6 | 150 | 15-73 | 150 | + |
| 6 | 150 | 16-1 | 150 | ++ |
| 6 | 150 | D-16-1 | 150 | ++ |
| 6 | 150 | L-16-1 | 150 | ++ |
| 6 | 150 | 16-2 | 300 | +++ |
| 6 | 150 | 16-2 | 150 | ++-+++ |
| 6 | 150 | 16-2 | 75 | ++ |
| 6 | 150 | 16-2 | 37.5 | +-++ |
| 6 | 150 | D-16-2 | 150 | ++-+++ |
| 6 | 150 | L-16-2 | 150 | ++-+++ |
| 6 | 150 | 16-3 | 150 | +++ |
| 6 | 150 | 16-9 | 150 | +++ |
| 6 | 150 | 16-15 | 150 | +++ |
| 6 | 150 | 16-16 | 150 | +++ |
| 6 | 150 | 16-18 | 150 | + |
| 6 | 150 | 16-20 | 150 | ++ |
| 6 | 150 | 16-22 | 150 | + |
| 6 | 150 | 16-23 | 150 | + |
| 6 | 150 | 16-24 | 150 | +++ |
| 6 | 150 | 16-25 | 150 | ++ |
| 6 | 150 | 16-27 | 150 | + |
| 6 | 150 | 16-36 | 150 | +++ |
| 6 | 150 | 16-37 | 150 | + |
| 6 | 150 | 16-38 | 150 | ++ |
| 6 | 150 | 16-39 | 150 | + |
| 6 | 150 | 16-41 | 150 | + |
| 6 | 150 | 16-44 | 150 | +++ |
| 6 | 150 | 17-1 | 150 | ++ |
| 6 | 150 | D-17-1 | 150 | ++ |
| 6 | 150 | L-17-1 | 150 | ++ |
| 6 | 150 | 17-2 | 300 | +++ |
| 6 | 150 | 17-2 | 150 | +++ |
| 6 | 150 | 17-2 | 75 | ++-+++ |
| 6 | 150 | 17-2 | 37.5 | ++ |
| 6 | 150 | L-17-2 | 150 | +++ |
| 6 | 150 | 17-4 | 150 | + |
| 6 | 150 | 17-5 | 150 | + |
| 6 | 150 | 17-7 | 150 | ++ |
| 6 | 150 | 17-12 | 150 | ++ |
| 6 | 150 | 17-13 | 150 | +++ |
| 6 | 150 | 17-14 | 150 | +++ |
| 6 | 150 | 17-16 | 150 | ++ |
| 6 | 150 | 17-18 | 150 | ++ |
| 6 | 150 | 17-19 | 150 | +++ |
| 6 | 150 | 17-24 | 150 | + |
| 6 | 150 | 17-26 | 150 | +++ |
| 6 | 150 | 17-30 | 150 | ++ |

TABLE-continued

| (Carba)-Penem Cpd. No. | Amount mg/kg | Amino Acid Cpd. No. | Amount mg/kg | Effect |
|---|---|---|---|---|
| 6 | 150 | 18-1 | 150 | + |
| 6 | 150 | 19-3 | 150 | +++ |
| 6 | 150 | 20-1 | 150 | ++ |
| 6 | 150 | 20-3 | 150 | +++ |
| 6 | 150 | 20-8 | 150 | + |
| 6 | 150 | 21-2 | 150 | + |
| 6 | 150 | 22-2 | 150 | + |
| 6 | 150 | 22-3 | 150 | + |
| 6 | 150 | 24-4 | 150 | + |
| 6 | 150 | 25-6 | 150 | + |
| 6 | 150 | 26-3 | 150 | ++ |
| 6 | 150 | 27-2 | 150 | ++ |
| 6 | 150 | 28-2 | 150 | + |
| 6 | 150 | 29-1 | 150 | + |
| 6 | 150 | 30-3 | 150 | + |
| 6 | 150 | 33-9 | 150 | + |
| 6 | 150 | 34-5 | 150 | + |
| 6 | 400 | 36-4 | 400 | +++ |
| 6 | 150 | 36-5 | 150 | ++ |
| 6 | 150 | 36-7 | 150 | + |
| 6 | 150 | 36-11 | 150 | +++ |
| 6 | 150 | 36-14 | 150 | ++ |
| 6 | 150 | 36-15 | 150 | + |
| 6 | 150 | 36-16 | 150 | + |
| 6 | 150 | 36-20 | 150 | ++ |
| 6 | 150 | 37-2 | 150 | +++ |
| 6 | 150 | 37-3 | 150 | ++ |
| 6 | 150 | 37-6 | 150 | + |
| 6 | 150 | 37-8 | 150 | + |
| 6 | 150 | 37-12 | 150 | ++ |
| 6 | 150 | 37-13 | 150 | ++ |
| 6 | 150 | 37-14 | 150 | +++ |
| 6 | 150 | 38-3 | 150 | + |
| 6 | 150 | 39-3 | 150 | ++ |
| 6 | 150 | 40-3 | 150 | ++ |
| 6 | 150 | 42-2 | 150 | ++ |
| 6 | 150 | 44-2 | 150 | + |
| 6 | 150 | 44-4 | 150 | ++ |
| 6 | 150 | 44-7 | 150 | + |
| 6 | 150 | 45-2 | 150 | ++ |
| 6 | 150 | 46-1 | 150 | + |
| 6 | 150 | 46-3 | 150 | +++ |
| 6 | 150 | 46-5 | 150 | + |
| 6 | 150 | 46-7 | 150 | ++ |
| 6 | 150 | 46-8 | 150 | ++ |
| 6 | 150 | 47-3 | 150 | ++ |
| 6 | 150 | 48-5 | 150 | + |
| 6 | 150 | 49-1 | 150 | ++ |
| 6 | 150 | 50-3 | 150 | ++ |
| 6 | 150 | 51-2 | 150 | + |
| 6 | 150 | 51-5 | 150 | ++ |
| 6 | 150 | 51-9 | 150 | + |
| 6 | 150 | 52-2 | 150 | + |
| 6 | 150 | 52-7 | 150 | + |
| 6 | 400 | 53-5 | 400 | +++ |
| 6 | 150 | 53-6 | 150 | +++ |
| 6 | 150 | 53-7 | 150 | +++ |
| 6 | 150 | 53-10 | 150 | ++ |
| 6 | 150 | 53-12 | 150 | ++ |
| 6 | 150 | 54-1 | 150 | ++ |
| 6 | 150 | 55-6 | 150 | ++ |
| 6 | 150 | 56-1 | 150 | ++ |
| 6 | 150 | 57-1 | 150 | ++ |
| 6 | 150 | 58-3 | 150 | ++ |
| 6 | 150 | 59-3 | 150 | ++ |
| 6 | 150 | 60-3 | 150 | +++ |
| 6 | 150 | 60-4 | 150 | ++ |
| 6 | 150 | 60-6 | 150 | + |
| 6 | 150 | 60-7 | 150 | + |
| 6 | 150 | 61-1 | 150 | + |
| 6 | 150 | 61-3 | 150 | ++ |
| 6 | 150 | 61-6 | 150 | + |
| 6 | 150 | 61-9 | 150 | + |
| 6 | 150 | 62-1 | 150 | +++ |
| 6 | 150 | 62-4 | 150 | ++ |
| 6 | 150 | 62-7 | 150 | ++ |
| 6 | 150 | 63-2 | 150 | + |
| 6 | 150 | 63-6 | 150 | + |
| 6 | 150 | 64-2 | 150 | ++ |
| 1 | 150 | 2-22 | 150 | ++ |
| 1 | 150 | 3-3 | 150 | ++ |
| 1 | 250 | 5-11 | 250 | +++ |
| 1 | 150 | 5-18 | 150 | +++ |
| 1 | 150 | 10-45 | 150 | ++ |
| 1 | 150 | 16-36 | 150 | +++ |
| 1 | 150 | 36-4 | 150 | +++ |
| 1 | 150 | 37-10 | 150 | ++ |
| 1 | 150 | 53-5 | 150 | ++ |
| 2 | 150 | 4-6 | 150 | +++ |
| 2 | 150 | 5-11 | 150 | +++ |
| 2 | 150 | 7-14 | 150 | +++ |
| 2 | 250 | 9-3 | 250 | +++ |
| 2 | 150 | 10-23 | 150 | ++ |
| 2 | 150 | 36-15 | 150 | ++ |
| 2 | 250 | 53-5 | 250 | ++ |
| 2 | 150 | 53-23 | 150 | ++ |
| 3 | 150 | 5-11 | 150 | +++ |
| 3 | 250 | 10-29 | 250 | +++ |
| 3 | 250 | 13-5 | 250 | ++ |
| 3 | 150 | 13-13 | 150 | ++ |
| 3 | 150 | 36-20 | 150 | ++ |
| 3 | 250 | 37-2 | 250 | ++ |
| 3 | 150 | 53-12 | 150 | ++ |
| 7 | 150 | 2-22 | 150 | +++ |
| 7 | 250 | 5-11 | 250 | ++ |
| 7 | 150 | 10-45 | 150 | +++ |
| 7 | 150 | 14-14α | 150 | ++ |
| 7 | 150 | 14-27 | 150 | +++-++ |
| 7 | 150 | 14-28 | 150 | +++-++ |
| 7 | 150 | 15-4ε | 150 | ++-+ |
| 7 | 150 | 15-12α | 150 | ++ |
| 7 | 150 | 15-27 | 150 | +++-++ |
| 7 | 150 | 15-29 | 150 | +++-++ |
| 7 | 150 | 15-44 | 150 | ++-+ |
| 7 | 150 | 16-1 | 150 | ++ |
| 7 | 150 | 16-2 | 150 | ++ |
| 7 | 150 | 16-31 | 150 | +++ |
| 7 | 150 | 17-1 | 150 | ++ |
| 7 | 150 | 17-2 | 150 | ++-+++ |
| 7 | 150 | 53-6 | 150 | +++ |
| 8 | 150 | 2-22 | 150 | ++ |
| 8 | 150 | 6-11 | 150 | +-++ |
| 8 | 150 | 14-29 | 150 | +++-++ |
| 8 | 150 | 15-27 | 150 | +++ |
| 8 | 150 | 16-1 | 150 | ++ |
| 8 | 150 | 16-2 | 150 | ++-+++ |
| 8 | 150 | 17-1 | 150 | ++ |
| 8 | 150 | 17-2 | 150 | +++ |
| 8 | 250 | 53-5 | 250 | ++-+++ |
| 9 | 150 | 36-6 | 150 | + |
| 9 | 250 | 53-5 | 250 | ++ |
| 10 | 150 | 13-5 | 150 | ++ |
| 10 | 150 | 21-6 | 150 | + |
| 11 | 150 | 2-22 | 150 | ++ |
| 11 | 150 | 15-28 | 150 | +++ |
| 11 | 150 | 16-2 | 150 | ++-+++ |
| 11 | 150 | 17-2 | 150 | +++ |
| 15 | 150 | 10-45 | 150 | +++ |
| 15 | 150 | 15-26 | 150 | +++-++ |
| 15 | 150 | 17-2 | 150 | ++ |
| 19 | 150 | L-10-45 | 150 | ++ |
| 19 | 150 | 15-27 | 150 | +++ |
| 19 | 150 | 17-2 | 150 | ++ |
| 22 | 250 | 36-4 | 250 | ++ |
| 22 | 150 | 37-15 | 150 | +-++ |
| 23 | 150 | 2-22 | 150 | +++ |
| 23 | 150 | 15-27 | 150 | +++ |
| 23 | 150 | 15-29 | 150 | +++ |
| 23 | 150 | 16-2 | 150 | ++ |
| 23 | 150 | 17-2 | 150 | +++ |
| 24 | 150 | 2-22 | 150 | +++ |
| 24 | 150 | 10-45 | 150 | +++ |
| 24 | 150 | D-10-45 | 150 | +++ |
| 24 | 150 | L-10-45 | 150 | +++ |
| 24 | 150 | 14-27 | 150 | +++ |
| 24 | 150 | 14-28 | 150 | +++-++ |
| 24 | 150 | 14-29 | 150 | +++-++ |
| 24 | 150 | 15-18 | 150 | ++ |

TABLE-continued

| (Carba)-Penem Cpd. No. | Amount mg/kg | Amino Acid Cpd. No. | Amount mg/kg | Effect |
|---|---|---|---|---|
| 24 | 150 | 15-26 | 150 | ++ |
| 24 | 150 | 15-27 | 150 | ++-++ |
| 24 | 150 | 15-28 | 150 | ++-++ |
| 24 | 150 | 15-29 | 150 | +++ |
| 24 | 150 | 15-47 | 150 | ++ |
| 24 | 150 | 16-1 | 150 | ++ |
| 24 | 150 | 16-2 | 150 | ++-+++ |
| 24 | 150 | 17-1 | 150 | ++ |
| 24 | 150 | 17-2 | 150 | +++ |
| 24 | 150 | 21-5 | 150 | + |
| 25 | 150 | 9-3 | 150 | ++ |
| 28 | 150 | 3-18 | 150 | + |
| 28 | 150 | 36-21 | 150 | +++ |
| 32 | 150 | 2-22 | 150 | ++ |
| 32 | 150 | 14-27 | 150 | +++ |
| 32 | 150 | 15-27 | 150 | +++ |
| 32 | 150 | 16-2 | 150 | ++ |
| 32 | 150 | 17-2 | 150 | ++ |
| 38 | 150 | 2-22 | 150 | +++ |
| 38 | 300 | 14-27 | 150 | ++ |
| 38 | 300 | 15-27 | 150 | ++ |
| 38 | 300 | 16-2 | 150 | ++ |
| 38 | 300 | 17-2 | 150 | ++ |
| 39 | 150 | 10-45 | 150 | ++ |
| 39 | 300 | 14-27 | 150 | ++ |
| 39 | 300 | 15-27 | 150 | ++ |
| 39 | 300 | 16-2 | 150 | ++ |
| 39 | 300 | 17-2 | 150 | ++ |
| 40 | 150 | 2-22 | 150 | +++ |
| 40 | 300 | 14-27 | 150 | +++ |
| 40 | 300 | 15-27 | 150 | +++ |
| 40 | 300 | 16-2 | 150 | ++ |
| 40 | 300 | 17-2 | 150 | ++ |
| 66 | 250 | 3-3 | 250 | ++ |
| 67 | 150 | 5-19 | 150 | ++ |
| 67 | 150 | 12-4 | 150 | +-++ |
| 71 | 250 | 2-18 | 250 | +++ |
| 71 | 250 | 5-21 | 250 | ++ |
| 73 | 150 | 11-27 | 150 | + |
| 73 | 150 | 37-10 | 150 | ++ |
| 75 | 150 | 16-36 | 150 | ++ |
| 75 | 150 | 36-9 | 150 | ++ |

We claim:

1. An antibiotic composition comprising:
an antibiotic selected from the group consisting of penem antibiotics and carbapenem antibiotics having renal toxicity; and
a pharmaceutically acceptable N-acylated derivative of an amino acid wherein the amino group and the carboxylic acid group are attached to a saturated aliphatic carbon chain or carbon atom, or a salt thereof in an amount at least sufficient to reduce or eliminate said renal toxicity.

2. A composition as claimed in claim 1, wherein the weight ratio of said N-acylated amino acid to said antibiotic is from about 0.1:1 to 4:1.

3. A composition as claimed in claim 2, wherein said amino acid is a compound of formula (II):

$$H_2N-X-COOH \qquad (II)$$

wherein X represents a $C_1-C_{10}$ alkylene group or a $C_1-C_{10}$ alkylene group having at least one substituent selected from the group consisting of hydroxy groups, $C_1-C_4$ alkoxy groups, $C_6-C_{14}$ aryloxy groups, substituted $C_6-C_{14}$ aryloxy groups, $C_7-C_9$ aralkyloxy groups, substituted $C_7-C_9$ aralkyloxy groups, mercapto groups, $C_1-C_4$ alkylthio groups, $C_6-C_{14}$ arylthio groups, substituted $C_6-C_{14}$ arylthio groups, $C_7-C_9$ aralkylthio groups, substituted $C_7-C_9$ aralkylthio groups, $C_2-C_5$ carboxyalkylthio groups, amino groups, amino groups having one or two substituents selected from the group consisting of
$C_1-C_4$ alkyl groups, $C_6-C_{14}$ aryl groups, substituted $C_6-C_{14}$ aryl groups, $C_7-C_9$ aralkyl groups, substituted $C_7-C_9$ aralkyl groups and carboxylic acyl groups.
$C_6-C_{14}$ aryl groups, substituted $C_6-C_{14}$ aryl groups, carboxy groups, amidino groups, sulfo groups, $C_1-C_4$ alkylsulfinyl groups, $C_1-C_4$ alkylsulfonyl groups and heterocyclic groups having from 5 to 14 ring atoms of which from 1 to 5 are hetero-atoms selected from the group consisting of nitrogen, oxygen and sulfur atoms, said substituted aryloxy, aralkyloxy, arylthio, aralkylthio, aryl and aralkyl groups having at least one substituent selected from the group consisting of $C_1-C_4$ alkyl groups, hydroxy groups, amino groups and $C_1-C_4$ alkoxy groups,
or a pharmaceutically acceptable salt thereof.

4. A composition as claimed in claim 3, wherein the N-acyl group is selected from the group consisting of: $C_1-C_{18}$ alkanoyl groups; $C_3-C_8$ alkenoyl groups; $C_3-C_8$ alkynoyl groups; aromatic acyl groups wherein the aryl part is $C_6-C_{14}$ carbocyclic aryl and is unsubstituted or has from 1 to 5 substituents is selected from the group consisting of $C_1-C_4$ alkyl groups, hydroxy groups, $C_1-C_4$ alkoxy groups, amino groups, sulfo groups and halogen atoms; cycloalkanecarbonyl groups where the cycloalkane part is $C_3-C_8$ and is unsubstituted or has at least one substituent selected from the group consisting of $C_1-C_4$ alkyl groups and phenyl groups; araliphatic acyl groups in which the aryl ring is a carbocyclic ring having from 6 to 14 carbon atoms and which is unsubstituted or has from 1 to 5 substituents selected from the group consisting of $C_1-C_4$ alkyl groups, hydroxy groups, $C_1-C_4$ alkoxy groups, amino groups, sulfo groups and halogen atoms, and in which the alkyl moiety has from 1 to 4 carbon atoms; heterocyclic acyl groups which have saturated or unsaturated ring systems, the rings having 5 or 6 ring atoms, of which from 1 to 3 are hetero-atoms independently selected from the group consisting of nitrogen, sulfur and oxygen atoms and the ring being unsubstituted or having from 1 to 3 substituents selected from the group consisting of $C_1-C_4$ alkyl groups and hydroxy groups; $C_2-C_7$ alkoxycarbonyl groups; aralkyloxycarbonyl groups where the aralkyl part has from 7 to 9 carbon atoms and is unsubstituted or has from 1 to 5 substituents selected from the group consisting of amino groups, $C_1-C_4$ alkyl groups, $C_1-C_4$ alkoxy groups and hydroxy groups; and acyl groups derived from an amino acid by removal of OH from the carboxylic acid group and N-acylation of the amino group with at least one of the above-mentioned acyl groups.

5. A composition as claimed in claim 3, wherein the N-acyl group is selected from the group consisting of: saturated aliphatic acyl groups having from 1 to 8 carbon atoms; aromatic acyl groups in which the aryl moiety has from 6 to 10 ring carbon atoms and is unsubstituted or has from 1 to 3 substituents independently selected from the group consisting of $C_1$–$C_4$ alkyl groups and $C_1$–$C_4$ alkoxy groups;

alicyclic acyl groups in which the cycloalkane ring has from 3 to 6 carbon atoms; araliphatic acyl groups in which the aryl ring has from 6 to 10 ring carbon atoms and the alkyl group has from 1 to 4 carbon atoms, the aryl ring being unsubstituted or having from 1 to 3 substituents independently selected from the group consisting of $C_1$–$C_4$ alkyl groups and $C_1$–$C_4$ alkoxy groups; heterocyclic acyl groups in which the heterocyclic ring is saturated or unsaturated and has 5 or 6 ring atoms of which one is a nitrogen, sulfur or oxygen hetero-atom; alkoxycarbonyl groups having a total of from 2 to 7 carbon atoms; aralkyloxycarbonyl groups in which the aralkyl moiety has from 7 to 9 carbon atoms and the aryl ring is unsubstituted or has from 1 to 3 substituents independently selected from the group consisting of $C_1$–$C_4$ alkyl groups and $C_1$–$C_4$ alkoxy groups; and acyl groups derived from an amino acid by removal of OH from the carboxylic acid group and N-acylation of the amino group with at least one of the above-mentioned acyl groups.

6. A composition as claimed in claim 3, wherein the N-acyl group is selected from the group consisting of:

aromatic acyl groups in which the aryl ring has from 6 to 10 ring atoms and which is unsubstituted or has a single substituent selected from the group consisting of $C_1$–$C_4$ alkyl groups, $C_1$–$C_4$ alkoxy groups, hydroxy groups and amino groups; alicyclic acyl groups in which the cycloalkane moiety has from 3 to 6 carbon atoms; phenylaliphatic acyl groups in which the phenyl group is unsubstituted or has a single $C_1$–$C_4$ alkyl substituent, and in which the alkyl part has from 1 to 4 carbon atoms; alkoxycarbonyl groups having a total of from 4 to 6 carbon atoms;

aralkyloxycarbonyl groups in which the aralkyl part has from 7 to 9 carbon atoms and has 0 or 1 substituent selected from the group consisting of $C_1$–$C_4$ alkyl groups and $C_1$–$C_4$ alkoxy group; and acyl groups derived from an amino acid by removal of OH from the carboxylic acid group and N-acylation of the amino group with at least one of the above-mentioned acyl groups.

7. A composition as claimed in claim 3, wherein the N-acyl group is selected from the group consisting of: acetyl, benzoyl, cyclohexanecarbonyl, cyclopropanecarbonyl, hexanoyl, isobutyryl, crotonyl, ethoxycarbonyl, 4-hydroxybenzoyl, anisoyl, 4-aminobenzoyl, naphthoyl, toluoyl, benzyloxycarbonyl and 4-methoxybenzyloxycarbonyl groups.

8. A composition as claimed in claim 3, wherein X represents a $C_1$–$C_5$ alkylene group which is unsubstituted or has one or two substituents independently selected from the group consisting of: hydroxy groups; $C_1$–$C_4$ alkoxy groups; aryloxy groups wherein the aryl ring has from 6 to 14 ring carbon atoms and which is unsubstituted or has from 1 to 3 substituents independently selected from the group consisting of $C_1$–$C_4$ alkyl groups, hydroxy groups, amino groups and $C_1$–$C_4$ alkoxy groups; $C_7$–$C_9$ aralkyloxy groups, wherein the aryl moiety is unsubstituted or has from 1 to 3 substituents independently selected from the group consisting of $C_1$–$C_4$ alkyl groups, hydroxy groups, amino groups and $C_1$–$C_4$ alkoxy groups, mercapto groups; $C_1$–$C_4$ alkylthio groups; arylthio groups wherein the aryl ring has from 6 to 14 ring carbon atoms and which is unsubstituted or has from 1 to 3 substituents independently selected from the group consisting of $C_1$–$C_4$ alkyl groups, hydroxy groups, amino groups and $C_1$–$C_4$ alkoxy groups; $C_7$–$C_9$ aralkylthio groups wherein the aryl ring is unsubstituted or has from 1 to 3 substituents independently selected from the group consisting of $C_1$–$C_4$ alkyl groups, hydroxy groups, amino groups and $C_1$–$C_4$ alkoxy groups; carboxyalkylthio groups in which the alkyl part has from 1 to 4 carbon atoms; amino groups, amino groups having one or two $C_1$–$C_4$ alkyl substituents; amino groups having one or two aryl substituents in which the aryl ring has from 6 to 14 ring carbon atoms and is unsubstituted or has from 1 to 3 substituents independently selected from the group consisting of $C_1$–$C_4$ alkyl groups, hydroxy groups, amino groups and $C_1$–$C_4$ alkoxy groups; amino groups having one or two $C_7$–$C_9$ aralkyl substituents in which the aryl part is unsubstituted or has from 1 to 3 substituents selected from the group consisting of $C_1$–$C_4$ alkyl groups, hydroxy groups, amino groups and $C_1$–$C_4$ alkoxy groups; amino groups having one or two carboxylic acyl substituents; aryl groups having from 6 to 14 ring carbon atoms and being unsubstituted or having from 1 to 3 substituents selected from the group consisting of $C_1$–$C_4$ alkyl groups, hydroxy groups, amino groups and $C_1$–$C_4$ alkoxy groups; carboxy groups; and heterocyclic groups having from 5 to 9 ring atoms, of which from 1 to 3 are hetero-atoms selected from the group consisting of nitrogen, oxygen and sulfur hetero-atoms.

9. A composition as claimed in claim 3, wherein X represents a $C_1$–$C_5$ alkylene group which is unsubstituted or has 1 or 2 substituents independently selected from the group consisting of: hydroxy groups; $C_1$–$C_4$ alkoxy groups; mercapto groups; $C_1$–$C_4$ alkylthio groups; amino groups; amino groups having one or two $C_1$–$C_4$ alkyl substituents; amino groups having one or two carboxylic acyl substituents; aryl groups having from 6 to 14 carbon atoms wherein the aryl ring is unsubstituted or has from 1 to 3 substituents selected from the group consisting of $C_1$–$C_4$ alkyl groups, hydroxy groups, amino groups and $C_1$–$C_4$ alkoxy groups; carboxy groups; and heterocyclic groups having from 5 to 9 ring atoms, of which from 1 to 3 are hetero-atoms selected from the group consisting of nitrogen and oxygen hetero-atoms.

10. A composition as claimed in claim 2, wherein said amino acid is glycine, $\beta$-alanine, 4-aminobutyric acid, 5-aminovaleric acid, 6-aminohexanoic acid, 8-aminooctanoic acid, alanine, 2-aminobutyric acid, norvaline, valine, leucine, isoleucine, norleucine, phenylglycine, phenylalanine, tyrosine, O-methyltyrosine, aspartic acid, glutamic acid, 4-carboxyglutamic acid, 3-methylaspartic acid, 2-aminoadipic acid, 2-aminopimelic acid, 2-aminosuberic acid, 3-hydroxyaspartic acid, 3-hydroxyglutamic acid, 2,3-diaminopropionic acid, 2,4-diaminobutyric acid, ornithine, lysine, 5-hydroxylysine, arginine, $N^\delta,N^\delta$-dimethylornithine, $N^\epsilon$-methyllysine, cysteine, methionine, ethionine, S-carboxymethylcysteine, S-benzylcysteine, methionine S-oxide, ethionine S-oxide, methionine S,S-dioxide, cysteic acid, serine, O-methylserine, threonine, O-methylthreonine, homothreonine, ethoxinine, 3-methoxyvaline, 3-phenylserine, 3-methyl-3-phenylalanine, histidine, tryptophan, 2-methylalanine, 2-methylserine, 2-hydroxyisoleucine, 2-methylmethionine, 2-ethyl-2-phenylglycine, 3-aminobutyric acid, 3-amino-4-methylvaleric acid, 3-amino-3-phenylpropionic acid, 3-amino-2-hydroxypropionic acid or 4-amino-3-hydroxybutyric acid.

11. A composition as claimed in claim 2, wherein said amino acid is glycine, β-alanine, 4-aminobutyric acid, 5-aminovaleric acid, 6-aminohexanoic acid, 8-aminooctanoic acid, alanine, norvaline, valine, leucine, isoleucine, norleucine, $N^\delta,N^\delta$-dimethylornithine, methionine, ethionine, O-methylserine, O-methylthreonine, ethoxinine, 3-methoxyvaline, 3-phenylserine, 3-methyl-3-phenylalanine, histidine, 2-methylalanine, 2-methylserine, 2-hydroxyisoleucine, 2-ethylphenylglycine, 3-aminobutyric acid, 3-amino-4-methylvaleric acid, 3-amino-3-phenylpropionic acid, ornithine, lysine, phenylalanine or phenylglycine.

12. A composition as claimed in claim 2, wherein said amino acid is β-alanine, 4-aminobutyric acid, 5-aminovaleric acid, 6-aminohexanoic acid, alanine, valine, leucine, norleucine, methionine, histidine, ornithine, glycine, phenylalanine or phenylglycine.

13. A composition as claimed in claim 2, wherein said amino acid is leucylglycine, glycyl-β-alanine, glycylalanine, valylalanine, leucylalanine, glycylvaline, alanylvaline, leucylvaline, valylleucine, phenylalanylleucine, histidylleucine, glycylphenylalanine, alanylphenylalanine, leucylphenylalanine, glycylmethionine, valylmethionine, glycylhistidine, alanylvalylglycine, glycylalanylvaline, glycylphenylalanylleucine or glycylglycylhistidine.

14. A composition as claimed in claim 2, wherein said amino acid is glycine, β-alanine, 4-aminobutyric acid, 5-aminovaleric acid, 6-aminohexanoic acid, 8-aminooctanoic acid, alanine, norvaline, valine, leucine, isoleucine, norleucine, $N^\delta,N^\delta$-dimethylornithine, methionine, ethionine, O-methylserine, O-methylthreonine, ethoxinine, 3-methoxyvaline, 3-phenylserine, 3-methyl-3-phenylalanine, histidine, 2-methylalanine, 2-methylserine, 2-hydroxyisoleucine, 2-ethylphenylglycine, 3-aminobutyric acid, 3-amino-4-methylvaleric acid, 3-amino-3-phenylpropionic acic, ornithine, lysine, phenylalanine or phenylglycine, and is N-acylated with an N-acyl group selected from the group consisting of: aromatic acyl groups in which the aryl ring has from 6 to 10 ring atoms and which is unsubstituted or has a single $C_1$–$C_4$ alkyl substituent; alicyclic acyl groups in which the cycloalkane moiety has from 3 to 6 carbon atoms; phenylaliphatic acyl groups in which the phenyl group is unsubstituted or has a single $C_1$–$C_4$ alkyl substituent, and in which the alkyl part has from 1 to 4 carbon atoms; alkoxycarbonyl groups having a total of from 4 to 6 carbon atoms; aralkyloxycarbonyl groups in which the aralkyl part has from 7 to 9 carbon atoms; and acyl groups derived from an amino acid by removal of OH from the carboxylic acid group and N-acylation of the amino group with at least one of the above-mentioned acyl groups.

15. A composition as claimed in claim 2, wherein said N-acylated amino acid is selected from the group consisting of:
N-(p-toluoyl)-β-alanine
N-(4-methoxybenzoyl)-β-alanine
N-(3-hydroxy-2-naphthoyl)-β-alanine
N-benzoylglycyl-β-alanine
N-benzoyl-β-alanine
N-benzoyl-5-aminovaleric acid
N-benzoyl-6-aminohexanoic acid
N-cyclohexanecarbonyl-6-aminohexanoic acid
N-(N-methylnicotinoyl)-6-aminohexanoic acid
N-benzoyl-8-aminooctanoic acid
N-benzoylalanine
N-(1-naphthoyl)alanine
N-benzoylvalylalanine
N-benzoyl-2-aminobutyric acid
N-benzoylnorvaline
N-valerylvaline
N-benzoylalanylvaline
N-benzoylvaline
N-benzoylleucine
N-benzoylglycylphenylalanylleucine
N-benzoylnorleucine
$N^{60},N^\delta$-dibenzoylornithine
$N^\alpha,N^\delta$-dicyclopropanecarbonylornithine
$N^\alpha,N^\delta$-dicyclohexanecarbonylornithine
$N^\alpha$-benzoyl-$N^\delta$-cyclohexanecarbonylornithine
$N^\alpha$-benzoyl-$N^\delta$-acetylornithine
$N^\alpha$-cyclohexanecarbonyl-$N^\delta$-acetylornithine
$N^\alpha,N^\epsilon$-dibenzoyllysine
$N^\alpha,N^\epsilon$-dicyclopropanecarbonyllysine
$N^\alpha,N^\epsilon$-dicyclohexanecarbonyllysine
$N^\alpha$-benzoyl-$N^\epsilon$-cyclohexanecarbonyllysine
$N^\alpha$-benzoyl-$N^\epsilon$-acetyllysine
$N^\alpha,N^\epsilon$-dianisoyllysine
$N^\alpha$-cyclohexanecarbonyl-$N^\epsilon$-acetyllysine
N-benzoylphenylalanine
N-(4-methoxybenzoyl)phenylalanine
N-hexanoylphenylalanine
N-cyclopropanecarbonylphenylalanine
N-cyclohexanecarbonylphenylalanine
N-anisoylphenylalanine
N-benzoylglycylphenylalanine
N-benzoylalanylphenylalanine
N-cyclohexanecarbonylleucylphenylalanine
N-benzoylphenylglycine
N-cyclopropanecarbonylphenylglycine
N-cyclohexanecarbonylphenylglycine
N-anisoylphenylglycine
N-(4-methoxybenzoyl)phenylglycine
N-benzoyl-O-methyltyrosine
N-benzoylmethionine
N-phenylacetylmethionine
N-benzoylvalylmethionine
N-benzoylethionine
N-(4-methoxybenzyloxycarbonyl)ethionine
N-benzoylthreonine
N-benzoylhistidine
N-(p-toluoyl)histidine
N-(4-methoxybenzoyl)histidine
N-(4-methoxybenzoyl)-3-aminobutyric acid and
N-butyryl-3-amino-3-phenylpropionic acid.

16. A composition as claimed in claim 2, wherein said antibiotic is selected from the group consisting of compounds of formula (I):

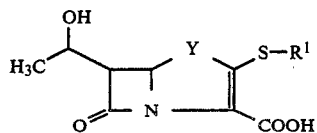

in which:
Y represents a sulfur atom, a methylene group or a methylene group having 1 or 2 substituents selected from the group consisting of methyl and methoxy groups; and
$R^1$ represents a $C_1$-$C_6$ alkyl group, a $C_1$-$C_6$ alkyl group having at least one substituent selected from the group consisting of substituents (i) or a heterocyclic group having from 4 to 14 ring atoms of which from 1 to 5 are hetero-atoms selected from the group consisting of nitrogen, oxygen and sulfur atoms where said heterocyclic group is unsubstituted or has at least one substituent selected from the group consisting of substituents (ii);
substituents (i):
halogen atoms, amino groups, amino groups having at least one substituents selected from the group consisting of substituents (iii), $C_1$-$C_4$ alkylideneamino groups, $C_1$-$C_4$ aminoalkylideneamino groups, amidino groups, amidino groups having from 1 to 3 substituents selected from the group consisting of substituents (iii), heterocyclic groups having from 4 to 14 ring atoms of which from 1 to 5 are hetero-atoms selected from the group consisting of nitrogen, oxygen and sulfur hetero-atoms wherein said heterocyclic group is unsubstituted or has at least one substituent selected from the group consisting of substituents (ii), imino groups, cyano groups, carbamoyl groups and carbamoyl groups having at least one substituent selected from the group consisting of $C_1$-$C_4$ alkyl groups and $C_1$-$C_4$ alkoxy groups;
substituents (ii):
$C_1$-$C_6$ alkanimidoyl groups, $C_1$-$C_6$ alkyl groups, alkoxyalkyl groups where the alkoxy and alkyl parts are each $C_1$-$C_4$, carbamoyl groups, carbamoyl groups having at least one substituent selected from the group consisting of $C_1$-$C_4$ alkyl groups and $C_1$-$C_4$ alkoxy groups, $C_1$-$C_4$ haloalkyl groups, heterocyclic acrylimidoyl groups where the heterocyclic part has from 5 to 9 ring atoms of which from 1 to 3 are hetero-atoms selected from the group consisting of nitrogen, oxygen and sulfur hetero-atoms, amidino groups, amidino groups having from 1 to 3 substituents selected from the group consisting of substituents (iii), imino groups, oxygen atoms, $C_1$-$C_6$ alkanoyl groups, $C_1$-$C_6$ alkanesulfonyl groups, $C_1$-$C_6$ alkanesulfinyl groups, hydroximino groups, $C_1$-$C_4$ alkoximino groups, carbamoyloxy groups, carbamoyloxy groups having at least one substituent selected from the group consisting of $C_1$-$C_4$ alkyl groups and $C_1$-$C_4$ alkoxy groups, carbamoyloxyalkyl groups where the alkyl part is $C_1$-$C_4$ and the carbamoyl part is unsubstituted or has at least one substituent selected from the group consisting of $C_1$-$C_4$ alkyl groups and $C_1$-$C_4$ alkoxy groups and $C_1$-$C_4$ iminoalkyl groups;
substituents (iii):
$C_1$-$C_6$ alkyl groups, $C_2$-$C_6$ alkenyl groups, $C_2$-$C_6$ alkynyl groups, oxygen atoms and said alkyl, alkenyl and alkynyl groups having at least one substituent selected from the group consisting of halogen atoms, carbamoyloxy groups and carbamoyloxy groups having at least one substituent selected from the group consisting of $C_1$-$C_4$ alkyl groups and $C_1$-$C_4$ alkoxy groups;
and pharmaceutically acceptable salts thereof.

17. A composition as claimed in claim 16, wherein Y represents a sulfur atom, a methylene group, or the group $CH_{13}$—CH<, $CH_3O$—CH< or $(CH_3)_2C<$.

18. A composition as claimed in claim 17, wherein $R^1$ represents an ethyl, 2-fluoroethyl, 2-(aminomethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)-$N^1$-methylamidinomethyl, $N^1$-(3-fluoropropyl)-$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidyl-3-pyrrolidinyl, $N^1,N^1$-diallylamidinomethyl, $N^1$-methyl-$N^1$-(2-propynyl)amidino, $N^1$-(2-fluoroethyl)-$N^1$-methylamidino, $N^1$-(3-fluoropropyl)-$N^1$-methylamidino, $N^1$-methyl-$N^1$-(2,2,2-trifluoroethyl)amidino, $N^1$-allyl-$N^1$-methylamidinomethyl, cyanomethyl, 2-cyanoethyl, 1-cyanoethyl, 2-cyano-1-methylethyl, 2-aminoethyl, 1-carbamoylethyl, 2-(1-aminoethylideneamino)ethyl, 1-amidino-3-pyrrolidinyl, 2-methyl-1,3-diazabicyclo[3.3.0]oct-2-en-7-yl, 2-methoxymethyl-1,3-diazabicyclo[3.3.0]oct-2-en-7-yl, 5-imino-2-pyrrolidinyl, 2-imino-5-piperidinyl, 1-acetimidoyl-5-methylcarbamoyl-3-pyrrolidinyl, 1-acetimidoyl-5-methoxycarbamoyl-3-pyrrolidinyl, 2-imino-2-(S-oxothiomorpholino)ethyl, 2-imino-2-(1,1-dioxo-1,3-thiazolidin-3-yl)ethyl, 2-imino-2-(S,S-dioxothiomorpholino)ethyl, 2-imino-2-(3,5-dioxo-1-piperazinyl)ethyl, 2-imino-2-(4-methyl-3,5-dioxo-1-piperazinyl)ethyl, 2-imino-2-(3-oxo-1-piperazinyl)ethyl, 2-imino-2-(4-methyl-3-oxo-1-piperazinyl)ethyl, 2-imino-2-(4-acetyl-3-oxo-1-piperazinyl)ethyl, 2-imino-2-(4-methanesulfonyl-3-oxo-1-piperazinyl)ethyl, $N^1$-(2-carbamoyloxyethyl)-$N^1$-methylamidinomethyl, 2-(3-hydroximino-1-pyrrolidinyl)-2-iminoethyl, 2-imino-2-(3-methoximino-1-pyrrolidinyl)ethyl, 2-(4-hydroximinopiperidino)-2-iminoethyl, 2-imino-2-(4-methoximinopiperidino)ethyl, 2-(3-carbamoyloxy-1-pyrrolidinyl)-2-iminoethyl, 2-imino-2-(3-oxo-1-piperazinyl)ethyl, 2-(3-carbamoylpiperidino)-2-iminoethyl, 2-(3-carbamoyloxypiperidino)-2-iminoethyl, 2-(2-carbamoyloxy-1-pyrrolidinyl)-2-iminoethyl, 2-(2-carbamoyloxymethyl-1-pyrrolidinyl)-2-iminoethyl, 2-(4-carbamoyloxypiperidino)-2-iminoethyl, 2-(4-formyl-1-piperazinyl)-2-iminoethyl, 2-(4-acetyl-1-piperazinyl)-2-iminoethyl, 1-formyl-3-azetidinyl, 1-iminomethyl-3-azetidinyl, 1-methyl-4-piperidyl, 1-acetimidoyl-4-piperidyl or 1-acetyl-3-pyrrolidinyl group.

19. A composition as claimed in claim 16, wherein said antibiotic is selected from the group consisting of:
(5R,6S)-2-{2-[(aminomethylene)amino]ethylthio}-6-[1(R)-hydroxyethyl]-2-carbapenem-3-carboxylic acid
(5R,6S)-2-[(3S)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-1(S)-methyl-2-carbapenem-3-carboxylic acid
(5R,6S)-2-[(3S)-1-acetimidoylpyrrolidin-3-ylthio]-6-[1(R)-hydroxyethyl]-1(R)-methyl-2-carbapenem-3-carboxylic acid
(5R,6S)-2-[(3S)-1-acetimidoylpyrrolidin-3-ylthio]-6-[1(R)-hydroxyethyl]-1(S)-methyl-2-carbapenem-3-carboxylic acid and
(5R,6S)-2-[(3S)-1-acetimidoyl-5(S)-carbamoylpyrrolidin-3-ylthio]-6-[1(R)-hydroxyethyl]-2-carbapenem-3-carboxylic acid.

20. An antibiotic composition comprising:
(a) an N-acylated amino acid selected from the group consisting of N-acylated derivatives of compounds of formula (II):

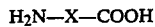   (II)

where X represents a $C_1-C_{10}$ alkylene group or a $C_1-C_{10}$ alkylene group having at least one substituent selected from the group consisting of hydroxy groups, $C_1-C_4$ alkoxy groups, $C_6-C_{14}$ aryloxy groups, substituted $C_6-C_{14}$ aryloxy groups, $C_7-C_9$ aralkyloxy groups, substituted $C_7-C_9$ aralkyloxy groups, mercapto groups, $C_1-C_4$ alkylthio groups, $C_6-C_{14}$ arylthio groups, substituted $C_6-C_{14}$ arylthio groups, $C_7-C_9$ aralkylthio groups, substituted $C_7-C_9$ aralkylthio groups, $C_2-C_5$ carboxyalkylthio groups, amino groups, amino groups having one or two substituents selected from the group consisting of
$C_1-C_4$ alkyl groups, $C_6-C_{14}$ aryl groups, substituted $C_6-C_{14}$ aryl groups, $C_7-C_9$ aralkyl groups, substituted $C_7-C_9$ aralkyl groups and carboxylic acyl groups,
$C_6-C_{14}$ aryl groups, substituted $C_6-C_{14}$ aryl groups, carboxy groups, amidino groups, sulfo groups, $C_1-C_4$ alkylsulfinyl groups, $C_1-C_4$ alkylsulfonyl groups and heterocyclic groups having from 5 to 14 ring atoms of which from 1 to 5 are hetero-atoms selected from the group consisting of nitrogen, oxygen and sulfur atoms, said substituted aryloxy, aralkyloxy, arylthio, aralkylthio, aryl and aralkyl groups having at least one substituent selected from the group consisting of $C_1-C_4$ alkyl groups, hydroxyl groups, amino groups and $C_1-C_4$ alkoxy groups; and pharmaceutically acceptable salt thereof; and (b) an antibiotic selected from the group consisting of compounds of formula (I):

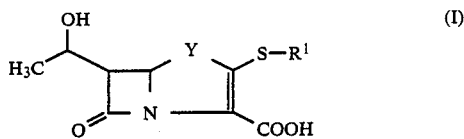   (I)

in which:
Y represents a sulfur atom, a methylene group or a methylene group having 1 or 2 substituents selected from the group consisting of methyl and methoxy groups; and
$R^1$ represents a $C_1-C_6$ alkyl group, a $C_1-C_6$ alkyl group having at least one substituent selected from the group consisting of substituents (i) or a heterocyclic group having from 4 to 14 ring atoms of which from 1 to 5 are hetero-atoms selected from the group consisting of nitrogen, oxygen and sulfur atoms where said heterocyclic group is unsubstituted or has at least one substituent selected from the group consisting of substituents (ii);
substituents (i):
halogen atoms, amino groups, amino groups having at least one substituent selected from the group consisting of substituents (iii), $C_1-C_4$ alkylideneamino groups, $C_1-C_4$ aminoalkylideneamino groups, amidino groups, amidino groups having from 1 to 3 substituents selected from the group consisting of substituents (iii), heterocyclic groups having from 4 to 14 ring atoms of which from 1 to 5 are hetero-atoms selected from the group consisting of nitrogen, oxygen and sulfur hetero-atoms wherein said heterocyclic group is unsubstituted or has at least one substituent selected from the group consisting of substituents (ii), imino groups, cyano groups, carbamoyl groups and carbamoyl groups having at least one substituent selected from the group consisting of $C_1-C_4$ alkyl groups and $C_1-C_4$ alkyl groups;
substituents (ii):
$C_1-C_6$ alkanimidoyl groups, $C_1-C_6$ alkyl groups, alkoxyalkyl groups where the alkoxy and alkyl parts are each $C_1-C_4$, carbamoyl groups, carbamoyl groups having at least one substituent selected from the group consisting of $C_1-C_4$ alkyl groups and $C_1-C_4$ alkoxy groups, $C_1-C_4$ haloalkyl groups, heterocyclic acylimidoyl groups where the heterocyclic part has from 5 to 9 ring atoms of which from 1 to 3 are hetero-atoms selected from the group consisting of nitrogen, oxygen and sulfur hetero-atoms, amidino groups, amidino groups having from 1 to 3 substituents selected from the group consisting of substituents (iii), imino groups, oxygen atoms, $C_1-C_6$ alkanoyl groups, $C_1-C_6$ alkanesulfonyl groups, $C_1-C_6$ alkanesulfinyl groups, hydroximino groups, $C_1-C_4$ alkoximino groups, carbamoyloxy groups, carbamoyloxy groups having at least one substituent selected from the group consisting of $C_1-C_4$ alkyl groups and $C_1-C_4$ alkoxy groups, carbamoyloxyalkyl groups where the alkyl part is $C_1$-$C_4$ and the carbamoyl part is unsubstituted or has at least one substituent selected from the group consisting of $C_1$-$C_4$ alkyl groups and $C_1$-$C_4$ alkoxy groups and $C_1$-$C_4$ iminoalkyl groups;
substituents (iii):
$C_1$-$C_6$ alkyl groups, $C_2$-$C_6$ alkenyl groups, $C_2$-$C_6$ alkynyl groups, oxygen atoms and said alkyl, alkenyl and alkynyl groups having at least one substituent selected from group consisting of halogen atoms, carbamoyloxy groups and carbamoyloxy groups having at least one substituent selected from the group consisting of $C_1$-$C_4$ alkyl groups and $C_1$-$C_4$ alkoxy groups;
and pharmaceutically acceptable salts thereof;
said antibiotic (b) having renal toxicity and said amino acid (a) being in an amount at least sufficient to reduce or eliminate said renal toxicity.

21. A composition as claimed in claim 20, wherein the weight ratio of said N-acylated amino acid to said antibiotic is from about 0.1:1 to 4:1.

22. A composition as claimed in claim 21, wherein the N-acyl group is selected from the group consisting of: saturated aliphatic acyl groups having from 1 to 8 carbon atoms; aromatic acyl groups in which the aryl moiety has from 6 to 10 ring carbon atoms and is unsubstituted or has from 1 to 3 substituents independently selected from the group consisting of $C_1$-$C_4$ alkyl groups and $C_1$-$C_4$ alkoxy group; alicyclic acyl groups in which the cycloalkane ring has from 3 to 6 carbon atoms; araliphatic acyl groups in which the aryl ring has from 6 to 10 ring carbon atoms and the alkyl group has from 1 to 4 carbon atoms, the aryl ring being unsubstituted or having from 1 to 3 substituents independently selected from the group consisting of $C_1$-$C_4$ alkyl groups and $C_1$-$C_4$ alkoxy groups; heterocyclic acyl groups in which the heterocyclic ring is saturated or unsaturated and has 5 or 6 ring atoms of which one is a nitrogen, sulfur or oxygen hetero-atom; alkoxycarbonyl groups having a total of from 2 to 7 carbon atoms; aralkyloxycarbonyl groups in which the aralkyl moiety has from 7 to 9 carbon atoms and the aryl ring is unsubstituted or has from 1 to 3 substituents independently selected from the group consisting of $C_1$-$C_4$ alkyl groups and $C_1$-$C_4$ alkoxy groups; and acyl groups derived from an amino acid by removal of OH from the carboxylic acid group and N-acylation of the amino group with at least one of the above-mentioned acyl groups.

23. A composition as claimed in claim 21, wherein the N-acyl group is selected from the group consisting of: aromatic acyl groups in which the aryl ring has from 6 to 10 ring atoms and which is unsubstituted or has a single substituent selected from the group consisting of $C_1$-$C_4$ alkyl groups, $C_1$-$C_4$ alkoxy group, hydroxy groups and amino groups; alicyclic acyl groups in which the cycloalkane moiety has from 3 to 6 carbon atoms; phenylaliphatic acyl groups in which the phenyl group is unsubstituted or has a single $C_1$-$C_4$ alkyl substituent, and in which the alkyl part has from 1 to 4 carbon atoms; alkoxycarbonyl groups having a total of from 4 to 6 carbon atoms; aralkyloxycarbonyl groups in which the aralkyl part has from 7 to 9 carbon atoms and has 0 or 1 substituent selected from the group consisting of $C_1$-$C_4$ alkyl groups and $C_1$-$C_4$ alkoxy groups; and acyl groups derived from an amino acid by removal of OH from the carboxylic acid group and N-acylation of the amino group with at least one of the above-mentioned acyl groups.

24. A composition as claimed in claim 21, wherein the N-acyl group is selected from the group consisting of: acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, napththoyl, toluoyl, benzyloxycarbonyl and 4-methoxybenzyloxycarbonyl groups.

25. A composition as claimed in claim 21, wherein X represents a $C_1$-$C_5$ alkylene group which is unsubstituted or has 1 to 2 substituents independently selected from the group consisting of: hydroxy groups; $C_1$-$C_4$ alkoxy group; mercapto groups; $C_1$-$C_4$ alkylthio groups; amino groups; amino groups having one or two $C_1$-$C_4$ alkyl substituents; amino groups having one or two carboxylic acyl substituents; aryl groups having from 6 to 14 carbon atoms wherein the aryl ring is unsubstituted or has from 1 to 3 substituents selected from the group consisting of $C_1$-$C_4$ alkyl groups, hydroxy groups, amino groups and $C_1$-$C_4$ alkoxy groups; carboxy groups; and heterocyclic groups having from 5 to 9 ring atoms, of which from 1 to 3 are hetero-atoms selected from the group consisting of nitrogen and oxygen hetero-atoms.

26. A composition as claimed in claim 21, wherein said amino acid is glycine, β-alanine, 4-aminobutyric acid, 5-aminovaleric acid, 6-aminohexanoic acid, 8-aminooctanoic acid, alanine, 2-aminobutyric acid, norvaline, valine, leucine, isoleucine, norleucine, phenyglycine, phenylalanine, tyrosine, O-methyltyrosine, aspartic acid, glutamic acid, 4-carboxyglutamic acid, 3-methylaspartic acid, 2-aminoadipic acid, 2-aminopimelic acid, 2-aminosuberic acid, 3-hydroxyaspartic acid, 3-hydroxyglutamic acid, 2,3-diaminopropionic acid, 2,4-diaminobutyric acid, ornithine, lysine, 5-hydroxylysine, arginine, $N^δ,N^δ$-dimethylornithine, $N^δ$-methyllysine, cysteine, methionine, ethionine, S-carboxymethylcysteine, S-benzylcysteine, methionine S-oxide, ethionine S-oxide, methionine S,S-dioxide, cysteic acid, serine, O-methylserine, threonine, O-methylthreonine, homothreonine, ethoxinine, 3-methoxyvaline, 3-phenylserine, 3-methyl-3-phenylalanine, histidine, tryptophan, 2-methylalanine, 2-methylserine, 2-hydroxyisoleucine, 2-methylmethionine, 2-ethyl-2-phenylglycine, 3-aminobutyric acid, 3-amino-4-methylvaleric acid, 3-amino-3-phenylpropionic acid, 3-amino-2-hydroxypropionic acid or 4-amino-3-hydroxybutyric acid.

27. A composition as claimed in claim 21, wherein said amino acid is β-alanine, 4-aminobutyric acid, 5-aminovaleric acid, 6-aminohexanoic acid, alanine, valine, leucine, norleucine, methionine, histidine, ornithine, glycine, phenylalanine or phenylglycine.

28. A composition as claimed in clsim 21, wherein said amino acid is leucylglycine, glycyl-β-alanine, glycylalanine, valylalanine, leucylalanine, glycylvaline, alanylvaline, leucylvaline, valylleucine, phenylalanylleucine, histidylleucine, glycylphenylalanine, alanylphenylalanine, leucylphenylalanine, glycylmethionine, valylmethionine, glycylhistidine, alanylvalylglycine, glyclylalanylvaline, glycylphenylalanylleucine, or glycylglycylhistidine.

29. A composition as claimed in claim 21, wherein said N-acylated amino acid is selected from the group consisting of:

N-(p-toluoyl)-β-alanine
N-(4-methoxybenzoyl)-β-alanine
N-(3-hydroxy-2-naphthoyl)-β-alanine
N-benzoylglycyl-β-alanine
N-benzoyl-β-alanine
N-benzoyl-5-aminovaleric acid
N-benzoyl-6-aminohexanoic acid
N-cyclohexanecarbonyl-6-aminohexanoic acid
N-(N-methylnicotinoyl)-6-aminohexanoic acid
N-benzoyl-8-aminooctanoic acid
N-benzoylalanine
N-(1-naphthoyl)alanine
N-benzoylvalylalanine
N-benzoyl-2-aminobutyric acid
N-benzoylnorvaline
N-valerylvaline
N-benzoylalanylvaline
N-benzoylvaline
N-benzoylleucine
N-benzoylglycylphenylalanylleucine
N-benzoylnorleucine
$N^\alpha,N^\delta$-dibenzoylornithine
$N^\alpha,N^\delta$-dicyclopropanecarbonylornithine
$N^\alpha,N^\delta$-dicyclohexanecarbonylornithine
$N^\alpha$-benzoyl-$N^\delta$-cyclohexanecarbonylornithine
$N^\alpha$-benzoyl-$N^\delta$-acetylornithine
$N^\alpha$-cyclohexanecarbonyl-$N^\delta$-acetylornithine
$N^\alpha,N^\epsilon$-dibenzoyllysine
$N^\alpha,N^\epsilon$-dicyclopropanecarbonyllysine
$N^\alpha,N^\epsilon$-dicyclohexanecarbonyllysine
$N^\alpha$-benzoyl-$N^\epsilon$-cyclohexanecarbonyllysine
$N^\alpha$-benzoyl-$N^\epsilon$-acetyllysine
$N^\alpha,N^\epsilon$-dianisoyllysine
$N^\alpha$-cyclohexanecarbonyl-$N^\epsilon$-acetyllysine
N-benzoylphenylalanine
N-(4-methoxybenzoyl)phenylalanine
N-hexanoylphenylalanine
N-cyclopropanecarbonylphenylalanine
N-cyclohexanecarbonylphenylalanine
N-anisoylphenylalanine
N-benzoylglycylphenylalanine
N-benzoylalanylphenylalanine
N-cyclohexanecarbonylleucylphenylalanine
N-benzoylphenyglycine
N-cyclopropanecarbonylphenylglycine
N-cyclohexanecarbonylphenylglycine
N-anisoylphenylglycine
N-(4-methoxybenzoyl)phenylglycine
N-benzoyl-O-methyltyrosine
N-benzoylmethionine
N-phenylacetylmethionine
N-benzoylvalylmethionine
N-benzoylethionine
N-(4-methoxybenzyloxycarbonyl)ethionine
N-benzoylthreonine
N-benzoylhistidine
N-(p-toluoyl)histidine
N-(4-methoxybenzoyl)histidine
N-(4-methoxybenzoyl)-3-aminobutyric acid and
N-butyryl-3-amino-3-phenylpropionic acid.

30. A composition as claimed in 21 wherein Y represents a sulfur atom, a methylene group, or the group $CH_3—CH<$, $CH_3O—CH<$ or $(CH_3)_2C<$.

31. A composition as claimed in claim 30, wherein $R^1$ represents an ethyl, 2-fluoroethyl, 2-(aminomethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)-$N^1$-methylamidinomethyl, $N^1$-(3-fluoropropyl)-$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidoyl-3-pyrrolidinyl, $N^1,N^1$-diallylamidinomethyl, $N^1$-methyl-$N^1$-(2-propynyl)amidino, $N^1$-(2-fluoroethyl)-$N^1$-methylamidino, $N^1$-(3-fluoropropyl)-$N^1$-methylamidino, $N^1$-methyl-$N^1$-(2,2,2-trifluoroethyl)amidino, $N^1$-allyl-$N^1$-methylamidinomethyl, cyanomethyl, 2-cyanoethyl, 1-cyanoethyl, 2-cyano-1-methylethyl, 2-aminoethyl, 1-carbamoylethyl, 2-(1-aminoethylideneamino)ethyl, 1-amidino-3-pyrrolidinyl, 2-methyl-1,3-diazabicyclo[3.3.0]oct-2-en-7-yl, 2-methoxymethyl-1,3-diazabicyclo[3.3.0]oct-2-en-7-yl, 5-imino-2-pyrrolidinyl, 2-imino-5-piperidinyl, 1-acetimidoyl-5-methylcarbamoyl-3-pyrrolidinyl, 1-acetimidoyl-5-methoxycarbamoyl-3-pyrrolidinyl, 2-imino-2-(S-oxothiomorpholino)ethyl, 2-imino-2-(1,1-dioxo-1,3-thiazolidin-3-yl)ethyl, 2-imino-2-(S,S-dioxothiomorpholino)ethyl, 2-imino-2-(3,5-dioxo-1-piperazinyl)ethyl, 2-imino-2-(4-methyl-3,5-dioxo-1-piperazinyl)ethyl, 2-imino-2-(3-oxo-1-piperazinyl)ethyl, 2-imino-2-(4-methyl-3-oxo-1-piperazinyl)ethyl, 2-imino-2-(4-acetyl-3-oxo-1-piperazinyl)ethyl, 2-imino-2-(4-methanesulfonyl-3-oxo-1-piperazinyl)ethyl, $N^1$-(2-carbamoyloxyethyl)-$N^1$-methylamidinomethyl, 2-(3-hydroximino-1-pyrrolidinyl)-2-iminoethyl, 2-imino-2-(3-methoximino-1-pyrrolidinyl)ethyl, 2-(4-hydroximinopiperidino)-2-iminoethyl, 2-imino-2-(4-methoximinopiperidino)ethyl, 2-(3-carbamoyloxy-1-pyrrolidinyl)-2-iminoethyl, 2-imino-2-(3-oxo-1-piperazinyl)ethyl, 2-(3-carbamoylpiperidino)-2-iminoethyl, 2-(3-carbamoyloxypiperidino)-2-iminoethyl, 2-(2-carbamoyloxy-1-pyrrolidinyl)-2-iminoethyl, 2-(2-carbamoyloxymethyl-1-pyrrolidinyl)-2-iminoethyl, 2-(4-carbamoyloxypiperidino)-2-iminoethyl, 2-(4-formyl-1-piperazinyl)-2-iminoethyl, 2-(4-acetyl-1-piperazinyl)-2-iminoethyl, 1-formyl-3-azetidinyl, 1-iminomethyl-3-azetidinyl, 1-methyl-4-piperidyl, 1-acetimidoyl-4-piperidyl or 1-acetyl-3-pyrrolidinyl group.

32. A composition as claimed in claim 21, wherein said antibiotic is selected from the group consisting of:
(5R,6S)-2-{2-[(aminomethylene)amino]ethylthio}-6-[1(R)-hydroxyethyl]-2-carbapenem-3-carboxylic acid (5R,6S)-2-[(3S)-1-acetimidoylpyrrolidin-3-ylthio]-6-[1(R)-hydroxyethyl]-2-carbapenem-3-carboxylic acid (5R,6S)-2-[(3R)-1-acetimidoylpyrrolidin-3-ylthio]-6-[1(R)-hydroxyethyl]-2-carbapenem-3-carboxylic acid (5R,6S)-2-[(3R)-1-acetimidoylpyrrolidin-3-ylthio]-6-[1(R)-hydroxyethyl]-1(S)-methyl-2-carbapenem-3-carboxylic acid (5R,6S)-2-[(3S)-1-acetimidoylpyrrolidin-3-ylthio]-6-[1(R)-hydroxyethyl]-1(R)-methyl-2-carbapenem-3-carboxylic acid (5R,6S)-2-[(3S)-1-acetimidoylpyrrolidin-3-ylthio]-6-[1(R)-hydroxyethyl]-1(S)-methyl-2-carbapenem-3-carboxylic acid and (5R,6S)-2-[(3S)-1-acetimidoyl-5(S)-carbamoylpyrrolidin-3-ylthio]-6-[1(R)-hydroxyethyl]-2-carbapenem-3-carboxylic acid.

33. A composition as claimed in claim 32, wherein said amino acid is glycine, β-alanine, 4-aminobutyric acid, 5-aminovaleric acid, 6-aminohexanoic acid, 8-aminooctanoic acid, alanine, 2-aminobutyric acid, norvaline, valine, leucine, isoleucine, norleucine, phenylglycine, phenylalanine, tyrosine, O-methyltyrosine, aspartic acid, glutamic acid, 4-carboxyglutamic acid, 3-methylaspartic acid, 2-aminoadipic acid, 2-aminopimelic acid, 2-aminosuberic acid, 3-hydroxyaspartic acid, 3-hydroxyglutamic acid, 2,3-diaminopropionic acid, 2,4-diaminobutyric acid, ornithine, lysine, 5-hydroxylysine, arginine, $N^\delta,N^\delta$-dimethylornithine, $N^\epsilon$-methyllysine, cysteine, methionine, ethionine, S-carboxymethylcysteine, S-benzylcysteine, methionine S-oxide, ethionine S-oxide, methionine S,S-dioxide, cysteic acid, serine, O-methylserine, threonine, O-methylthreonine, homothreonine, ethoxinine, 3-methoxyvaline, 3-phenylserine, 3-methyl-3-phenylalanine, histidine, tryptophan, 2-methylalanine, 2-methylserine, 2-hydroxyisoleucine, 2-methylmethionine, 2-ethyl-2-phenylglycine, 3-aminobutyric acid, 3-amino-4-methylvaleric acid, 3-amino-3-phenylpropionic acid, 3-amino-2-hydroxypropionic acid or 4-amino-3-hydroxybutyric acid.

34. A composition as claimed in claim 32, wherein said amino acid is β-alanine, 4-aminobutyric acid, 5-aminovaleric acid, 6-aminohexanoic acid, alanine, valine, leucine, norleucine, methionine, histidine, ornithine, glycine, phenylalanine or phenylglycine.

35. A composition as claimed in claim 32, wherein said amino acid is leucylglycine, glycyl-β-alanine, glycylalanine, valylalanine, leucylalanine, glycylvaline, alanylvaline, leucylvaline, valylleucine, phenylalanylleucine, histidylleucine, glycylphenylalanine, alanylphenylalanine, leucylphenylalanine, glycylmethionine, valylmethionine, glycylhistidine, alanylvalylglycine, glycylalanylvaline, glycylphenylalanylleucine or glycylglycylhistidine.

36. An antibiotic composition comprising:
an antibiotic selected from the group consisting of penem antibiotics and carbapenem antibiotics having renal toxicity; and
a pharmaceutically acceptable N-acylated derivative of an amino acid wherein said derivative is selected from the group consisting of N-benzoylvaline and N-benzoyl-β-alanine in an amount at least sufficient to reduce or eliminate said renal toxicity.

37. A composition as claimed in claim 36, wherein the weight ratio of said N-acylated amino acid to said antibiotic is from about 0.1:1 to 4:1.

38. A composition as claimed in claim 37, wherein said antibiotic is selected from the group consisting of compounds of formula (I):

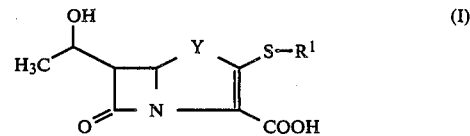

in which:
Y represents a sulfur atom, a methylene group or a methylene group having 1 or 2 substituents selected from the group consisting of methyl and methoxy groups; and
$R^1$ represents a $C_1$–$C_6$ alkyl group, a $C_1$–$C_6$ alkyl group having at least one substituent selected from the group consisting of substituents (i) or a heterocyclic group having from 4 to 14 ring atoms of which from 1 to 5 are hetero-atoms selected from the group consisting of nitrogen, oxygen and sulfur atoms where said heterocyclic group is unsubstituted or has at least one substituent selected from the group consisting of substituents (ii);
substituents (i):
halogen atoms, amino groups, amino groups having at least one substituent selected from the group consisting of substituents (iii), $C_1$–$C_4$ alkylideneamino groups, $C_1$–$C_4$ aminoalkylideneamino groups, amidino groups, amidino groups having from 1 to 3 substituents selected from the group consisting of substituents (iii), heterocyclic groups having from 4 to 14 ring atoms of which from 1 to 5 are hetero-atoms selected from the group consisting of nitrogen, oxygen and sulfur hetero-atoms wherein said heterocyclic group is unsubstituted or has at least one substituent selected from the group consisting of substituents (ii), imino groups, cyano groups, carbamoyl groups and carbamoyl groups having at least one substituent selected from the group consisting of $C_1$–$C_4$ alkyl groups and $C_1$–$C_4$ alkoxy groups;
substituents (ii):
$C_1$–$C_6$ alkanimidoyl groups, $C_1$–$C_6$ alkyl groups, alkoxyalkyl groups where the alkoxy and alkyl parts are each $C_1$–$C_4$, carbamoyl groups, carbamoyl groups having at least one substituent selected from the group consisting of $C_1$–$C_4$ alkyl groups and $C_1$–$C_4$ alkoxy groups, $C_1$–$C_4$ haloalkyl groups, heterocyclic acylimidoyl groups where the heterocyclic part has from 5 to 9 ring atoms of which from 1 to 3 are hetero-atoms selected from the group consisting of nitrogen, oxygen and sulfur hetero-atoms, amidino groups, amidino groups having from 1 to 3 substituents selected from the group consisting of substituents (iii), imino groups, oxygen atoms, $C_1$–$C_6$ alkanoyl groups, $C_1$–$C_6$ alkanesulfonyl groups, $C_1$–$C_6$ alkanesulfinyl groups, hydroximino groups, $C_1$–$C_4$ alkoximino groups, carbamoyloxy groups, carbamoyloxy groups having at least one substituent selected from the group consisting of $C_1$–$C_4$ alkyl groups and $C_1$–$C_4$ alkoxy groups, carbamoyloxyalkyl groups where the alkyl part is $C_1$–$C_4$ and the carbamoyl part is unsubstituted or has at least one substituent selected from the group consisting of $C_1$–$C_4$ alkyl groups and $C_1$–$C_4$ alkoxy groups and $C_1$–$C_4$ iminoalkyl groups;

substituents (iii):
$C_1$–$C_6$ alkyl groups, $C_2$–$C_6$ alkenyl groups, $C_2$–$C_6$ alkynyl groups, oxygen atoms and said alkyl, alkenyl and alkynyl groups having at least one substituent selected from the group consisting of halogen atoms, carbamoyloxy groups and carbamoyloxy groups having at least one substituent selected from the group consisting of $C_1$–$C_4$ alkyl groups and $C_1$–$C_4$ alkoxy groups;

and pharmaceutically acceptable salts thereof.

39. A composition as claimed in claim 38, wherein Y represents a sulfur atom, a methylene group, or the group $CH_3$—CH<, $CH_3O$—CH< or $(CH_3)_2C<$.

40. A composition as claimed in claim 39, wherein $R^1$ represents an ethyl, 2-fluoroethyl, 2-(aminomethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)-$N^1$-methylamidinomethyl, $N^1$-(3-fluoropropyl)-$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidoyl-3-pyrrolidinyl, $N^1,N^1$-diallylamidinomethyl, $N^1$-allyl-$N^1$-methylamidinomethyl, cyanomethyl, 2-cyanoethyl, 1-cyanoethyl, 2-cyano-1-methylethyl, 2-aminoethyl or 1-carbamoylethyl group.

41. A composition as claimed in claim 37, wherein said antibiotic is selected from the group consisting of:
(5R,6S)-2-{2-[(aminomethylene)amino]ethylthio}-6-[1(R)-hydroxyethyl]-2-carbapenem-3-carboxylic acid
(5R,6S)-2-[(3S)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-1(S)-methyl-2-carbapenem-3-carboxylic acid
(5R,6S)-2-[(3S)-1-acetimidoylpyrrolidin-3-ylthio]-6-[1(R)-hydroxyethyl]-1(R)-methyl-2-carbapenem-3-carboxylic acid
(5R,6S)-2-[(3S)-1-acetimidoylpyrrolidin-3-ylthio]-6-[1(R)-hydroxyethyl]-1(S)-methyl-2-carbapenem-3-carboxylic acid and (5R,6S)-2-[(3S)-1-acetimidoyl-5(S)-carbamoylpyrrolidin-3-ylthio]-6-[1(R)-hydroxyethyl]-2-carbapenem-3-carboxylic acid.

42. An antibiotic composition comprising:
an antibiotic selected from the group consisting of penem antibiotics and carbapenem antibiotics having renal toxicity; and
a pharmaceutically acceptable N-acylated amino acid wherein the amino acid is selected from the group consisting of ornithine, lysine, phenylglycine and phenylalanine and salts thereof in an amount at least sufficient to reduce or eliminate said renal toxicity.

43. A composition as claimed in claim 42, wherein the weight ratio of said N-acylated amino acid to said antibiotic is from about 0.1:1 to 4:1.

44. A composition as claimed in claim 43, wherein said N-acylated amino acid is a compound of formula (IV):

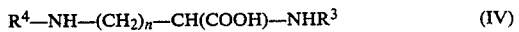

wherein:
n is 3 or 4; and
$R^3$ and $R^4$ are independently selected from the group consisting of hydrogen atoms and carboxylic acyl groups, provided that $R^3$ and $R^4$ are not both hydrogen; or a pharmaceutically acceptable salt thereof.

45. A composition as claimed in claim 44, wherein $R^3$ and $R^4$ are independently selected from the group consisting of: hydrogen atoms; $C_1$–$C_{18}$ alkanoyl groups; $C_3$–$C_8$ alkenoyl groups; $C_3$–$C_8$ alkynoyl groups; aromatic acyl groups wherein the aryl part is $C_6$–$C_{14}$ carbocyclic aryl and is unsubstituted or has from 1 to 5 substituents selected from the group consisting of $C_1$–$C_4$ alkyl groups, hydroxy groups, $C_1$–$C_4$ alkoxy groups, amino groups and sulfo groups; cycloalkanecarbonyl groups where the cycloalkane part is $C_3$–$C_8$; $C_2$–$C_7$ alkoxycarbonyl groups; and aralkyloxycarbonyl groups where the aralkyl part has from 7 to 9 carbon atoms and is unsubstituted or has from 1 to 5 substituents selected from the group consisting of amino groups, $C_1$–$C_4$ alkyl groups, $C_1$–$C_4$ alkoxy groups and hydroxy groups; provided that $R^3$ and $R^4$ are not both hydrogen.

46. A composition as claimed in claim 44, wherein $R^3$ and $R^4$ are independently selected from the group consisting of hydrogen atoms and acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, naphthoyl, toluoyl, benzyloxycarbonyl and 4-methoxybenzyloxycarbonyl groups, provided that $R^3$ and $R^4$ are not both hydrogen atoms.

47. A composition as claimed in claim 44, wherein at least one of $R^3$ and $R^4$ represents an acyl group selected from the group consisting of acetyl and benzoyl groups.

48. A composition as claimed in claim 43, wherein said N-acylated amino acid is a compound of formula (V):

wherein:
Ph represents a phenyl group;
m is 0 or 1; and
$R^2$ represents a carboxylic acyl group;
or a pharmaceutically acceptable salt thereof.

49. A composition as claimed in claim 48, wherein $R^2$ is selected from the group consisting of: $C_1$-$C_{18}$ alkanoyl groups; $C_3$-$C_8$ alkenoyl groups; $C_3$-$C_8$ alkynoyl groups; aromatic acyl groups wherein the aryl part is $C_6$-$C_{14}$ carbocyclic aryl and is unsubstituted or has from 1 to 5 substituents selected from the group consisting of $C_1$-$C_4$ alkyl groups, hydroxy groups, $C_1$-$C_4$ alkoxy groups, amino groups and sulfo groups; cycloalkanecarbonyl groups where the cycloalkane part is $C_3$-$C_8$; $C_2$-$C_7$ alkoxycarbonyl groups; and aralkyloxycarbonyl groups where the aralkyl part has from 7 to 9 carbon atoms and is unsubstituted or has from 1 to 5 substituents selected from the group consisting of amino groups, $C_1$-$C_4$ alkyl groups, $C_1$-$C_4$ alkoxy groups and hydroxy groups.

50. A composition as claimed in claim 48, wherein $R^2$ is selected from the group consisting of acetyl, benzoyl, cyclohexanecarbonyl, cyclopropanecarbonyl, hexanoyl, isobutyryl crotonoyl, ethoxycarbonyl, 4-hydroxybenzoyl, anisoyl, 4-aminobenzoyl, naphthoyl, toluoyl, benzyloxycarbonyl and 4-methoxybenzyloxycarbonyl groups.

51. A composition as claimed in claim 48, wherein $R^2$ represents an acyl group selected from the group consisting of acetyl and benzoyl groups.

52. A composition as claimed in claim 43, wherein said N-acylated amino acid is selected from the group consisting of:
$N^\alpha,N^\delta$-Dibenzoylornithine
$N^\alpha,N^\delta$-Dicyclohexanecarbonylornithine
$N^\alpha$-Benzoyl-$N^\delta$-cyclohexanecarbonylornithine
$N^\alpha$-Benzoyl-$N^\delta$-acetylornithine
$N^\alpha,N^\epsilon$-Dibenzoyllysine
$N^\alpha,N^\epsilon$-Dicyclohexanecarbonyllysine
$N^\alpha$-Benzoyl-$N^\epsilon$-cyclohexanecarbonyllysine
$N^\alpha$-Benzoyl-$N^\epsilon$-acetyllysine
N-Benzoylphenylglycine
N-Benzoylphenylalanine
N-Cyclohexanecarbonylphenylglycine
N-Cyclohexanecarbonylphenylalanine
$N^\alpha$-Cyclohexanecarbonyl-$N^\epsilon$-acetyllysine and
$N^\alpha$-Cyclohexanecarbonyl-$N^\delta$-acetylornithine.

53. A composition as claimed in claim 43, wherein said antibiotic is selected from the group consisting of compounds of formula (I):

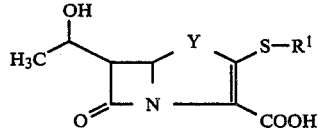
(I)

wherein:
Y represents a sulfur atom, a methylene group, or a methylene group having 1 or 2 methyl substituents; and
$R^1$ represents an ethyl, 2-fluoroethyl, 2-(aminoethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)$N^1$-methylamidinomethyl, $N^1$-(3-fluoropropyl)$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidoyl-3-pyrrolidinyl, $N^1,N^1$-diallylamidinomethyl, $N^1$-methyl-$N^1$-(2-propynyl)amidino, $N^1$-(2-fluoroethyl)-$N^1$-methylamidino, $N^1$-(3-fluoro-propyl)-$N^1$-methylamidino, $N^1$-methyl-$N^1$-(2,2,2-trifluoroethyl)amidino, $N^1$-allyl-$N^1$-methylamidinomethyl, cyanomethyl, 2-cyanoethyl, 1-cyanoethyl, 2-cyano-1-methylethyl, 2-aminoethyl or 1-carbamoylethyl group.

54. A composition as claimed in claim 53, wherein said antibiotic is selected from the group consisting of:
(5R,6S)-2-{2-[(aminomethylene)amino]ethylthio}-6-[1(R)-hydroxyethyl]-2-carbapenem-3-carboxylic acid
(5R,6S)-2-[(3S)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-1(S)-methyl-2-carbapenem-3-carboxylic acid
(5R,6S)-2-[(3S)-1-acetimidoylpyrrolidin-3-ylthio]-6-[1(R)-hydroxyethyl]-1(R)-methyl-2-carbapenem-3-carboxylic acid
(5R,6S)-2-[(3S)-1-acetimidoylpyrrolidin-3-ylthio]-6-[1(R)-hydroxyethyl]-1(S)-methyl-2-carbapenem-3-carboxylic acid and
(5R,6S)-2-[(3S)-1-acetimidoyl-5(S)-carbamoylpyrrolidin-3-ylthio]-6[1(R)-hydroxyethyl]-2-carbapenem-3-carboxylic acid.

55. An antibiotic composition comprising:
(a) an N-acylated amino acid selected from the group consisting of compounds of formula (IV):

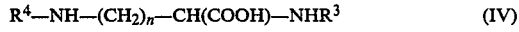
(IV)

wherein:
n is 3 or 4; and
$R^3$ and $R_4$ are independently selected from the group consisting of hydrogen atoms and carboxylic acyl groups, provided that $R^3$ and $R^4$ are not both hydrogen, and compounds of formula (V):

(V)

wherein:
Ph represents the phenyl group;
m is 0 or 1; and
$R^2$ represents a carboxylic acyl group;
or a pharmaceutically acceptable salt thereof; and (b) an antibiotic selected from the group consisting of compounds of formula (I):

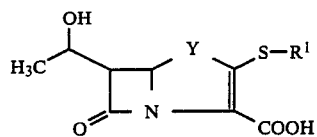

wherein:

Y represents a sulfur atom, a methylene group, or a methylene group having 1 or 2 methyl substituents; and $R^1$ represents an ethyl, 2-fluoroethyl, 2-(aminomethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)$N^1$-methylamidinomethyl, $N^1$-(3-fluoropropyl)$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidoyl-3-pyrrolidinyl, $N^1,N^1$-diallylamidinomethyl, $N^1$-methyl-$N^1$-(2-propynyl)amidino, $N^1$-(2-fluoroethyl)-$N^1$-methylamidino, $N^1$-(3-fluoropropyl)-$N^1$-methylamidino, $N^1$-methyl-$N^1$-(2,2,2-trifluoroethyl)amidino, $N^1$-allyl-$N^1$-methylamidinomethyl, cyanomethyl, 2-cyanoethyl, 1-cyanoethyl, 2-cyano-1-methylethyl, 2-aminoethyl or 1-carbamoylethyl group and pharmaceutically acceptable salts thereof;

said antibiotic (b) having renal toxicity and said amino acid (a) being in an amount at least sufficient to reduce or eliminate said renal toxicity.

56. The composition as claimed in claim 55, wherein the weight ratio of said N-acylated amino acid to said antibiotic is about from 0.1:1 to 4:1.

57. A composition as claimed in claim 56, wherein $R^3$ and $R^4$ are independently selected from the group consisting of: hydrogen atoms; $C_1$–$C_{18}$ alkanoyl groups; $C_3$–$C_8$ alkenoyl groups; $C_3$–$C_8$ alkynoyl groups; aromatic acyl groups wherein the aryl part is $C_6$–$C_{14}$ carbocyclic aryl and is unsubstituted or has from 1 to 5 substituents selected from the group consisting of $C_1$–$C_4$ alkyl groups, hydroxy groups, $C_1$–$C_4$ alkoxy groups, amino groups and sulfo groups; cycloalkanecarbonyl groups where the cycloalkane part is $C_3$–$C_8$; $C_2$–$C_7$ alkoxycarbonyl groups; and aralkyloxycarbonyl groups where the aralkyl part has from 7 to 9 carbon atoms and is unsubstituted or has from 1 to 5 substituents selected from the group consisting of amino groups, $C_1$–$C_4$ alkyl groups, $C_1$–$C_4$ alkoxy groups and hydroxy groups; provided that $R^3$ and $R^4$ are not both hydrogen.

58. A composition as claimed in claim 56, wherein $R^3$ and $R^4$ are independently selected from the group consisting of hydrogen atoms and acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, naphthoyl, toluoyl, benzyloxycarbonyl and 4-methoxybenzyloxycarbonyl groups, provided that $R^3$ and $R^4$ are not both hydrogen atoms.

59. A composition as claimed in claim 56, wherein at least one of $R^3$ and $R^4$ represents an acyl group selected from the group consisting of acetyl and benzoyl groups.

60. A composition as claimed in claim 56, wherein $R^2$ is selected from the group consisting of: $C_1$–$C_{18}$ alkanoyl groups; $C_3$–$C_8$ alkenoyl groups; $C_3$–$C_8$ alkynoyl groups; aromatic acyl groups wherein the aryl part is $C_6$–$C_{14}$ carbocyclic aryl and is unsubstituted or has from 1 to 5 substituents selected from the group consisting of $C_1$–$C_4$ alkyl groups, hydroxy groups, $C_1$–$C_4$ alkoxy groups, amino groups and sulfo groups; cycloalkanecarbonyl groups where the cycloalkane part is $C_3$–$C_8$; $C_2$–$C_7$ alkoxycarbonyl groups; and aralkyloxycarbonyl groups where the aralkyl part has from 7 to 9 carbon atoms and is unsubstituted or has from 1 to 5 substituents selected from the group consisting of amino groups, $C_1$–$C_4$ alkyl groups, $C_1$–$C_4$ alkoxy groups and hydroxy groups.

61. A composition as claimed in claim 56, wherein $R^2$ is selected from the group consisting of acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, naphthoyl, toluoyl, benzyloxycarbonyl and 4-methoxybenzyloxycarbonyl groups.

62. A composition as claimed in claim 56, wherein $R^2$ represents an acyl group selected from the group consisting of acetyl and benzoyl groups.

63. A composition as claimed in claim 56, wherein said N-acylated amino acid is selected from the group consisting of:

$N^\alpha,N^\delta$-Dibenzoylornithine
$N^\alpha,N^\delta$-Dicyclohexanecarbonylornithine
$N^\alpha$-Benzoyl-$N^\delta$-cyclohexanecarbonylornithine
$N^\alpha$-Benzoyl-$N^\delta$-acetylornithine
$N^\alpha,N^\epsilon$-Dibenzoyllysine
$N^\alpha,N^\epsilon$-Dicyclohexanecarbonyllysine
$N^\alpha$-Benzoyl-$N^\epsilon$-cyclohexanecarbonyllysine
$N^\alpha$-Benzoyl-$N^\epsilon$-acetyllysine
N-Benzoylphenylglycine
N-Benzoylphenylalanine
N-Cyclohexanecarbonylphenylglycine
N-Cyclohexanecarbonylphenylalanine
$N^\alpha$-Cyclohexanecarbonyl-$N^\epsilon$-acetyllysine and
$N^\alpha$-Cyclohexanecarbonyl-$N^\epsilon$-acetylornithine and said antibiotic is selected from the group consisting of:

(5R,6S)-2-{2-[(aminomethylene)amino]ethylthio}-6-[1(R)-hydroxyethyl]-2-carbapenem-3-carboxylic acid (5R,6S)-2-[(3S)-1-acetimidoylpyrrolidin-3-ylthio]-6-[1(R)-hydroxyethyl]-2-carbapenem-3-carboxylic acid (5R,6S)-2-[(3R)-1-acetimidoylpyrrolidin-3-ylthio]-6-[1(R)-hydroxyethyl]-2-carbapenem-3-carboxylic acid (5R,6S)-2-[(3R)-1-acetimidoylpyrrolidin-3-ylthio]-6-[1(R)-hydroxyethyl]-1(S)-methyl-2-carbapenem-3-carboxylic acid (5R,6S)-2-[(3S)-1-acetimidoylpyrrolidin-3-ylthio]-6-[1(R)-hydroxyethyl]-1(R)-methyl-2-carbapenem-3-carboxylic acid (5R,6S)-2-[(3S)-1-acetimidoylpyrrolidin-3-ylthio]-6-[1(R)-hydroxyethyl]-1(S)-methyl-2-carbapenem-3-carboxylic acid and (5R,6S)-2-[(3S)-1-acetimidoyl-5(S)-carbamoylpyrrolidin-3-ylthio]-6-[1(R)-hydroxyethyl]-2-carbapenem-3-carboxylic acid.

64. The antibiotic composition comprising:
(a) (5R,6S)-2-[(3S)-1-acetimidoylpyrrolidin-3-ylthio]-6-[1(R)hydroxyethyl]-2-carbapenem-3-carboxylic acid; and
(b) N-benzoyl-valine, wherein the weight ratio of (a) to (b) is from about 1:0.1 to 1:4.

65. A composition as claimed in claim 64, wherein said weight ratio is about 1:1.

66. An antibiotic composition comprising:
(a) (5R,6S)-2-[(3S)-1-acetimidoylpyrrolidin-3-ylthio]-6-[1(R)hydroxyethyl]-2-carbapenem-3-carboxylic acid; and
(b) an amount of N-benzoyl-$\beta$-alanine at least sufficient to reduce or eliminate renal toxicity of said carbapenem.

67. A composition as claimed in claim 66, wherein the weight ratio of (a) to (b) is from about 1:0.1 to 1:4.

68. A composition as claimed in claim 67, wherein said weight ratio is about 1:1.

69. A method of treating a mammal suffering from a bacterial infection by administering to said mammal:
an antibiotic selected from the group consisting of penem antibiotics and carbapenem antibiotics capable of causing renal damage in an amount effective to treat said bacterial infection; and
an amount of a pharmaceutically acceptable N-acylated derivative of an amino acid wherein the amino group and the carboxylic acid group are attached to a saturated aliphatic carbon chain or carbon atom, or a salt thereof at least sufficient to reduce, alleviate or prevent said renal damage;
said antibiotic and said amino acid derivative being administered to said mammal sufficiently closely in time to each other that the amino acid derivative has a suitable concentration in the blood while said antibiotic is in the blood to reduce, alleviate or prevent said renal damage.

70. The method as claimed in claim 69, wherein said antibiotic and said N-acylated derivative of an amino acid are administered concurrently.

71. The method as claimed in claim 70, wherein the weight ratio of said N-acylated amino acid to said antibiotic is from about 0.1:1 to 4:1.

72. The method as claimed in claim 69, wherein the weight ratio of said N-acylated amino acid to said antibiotic is from about 0.1:1 to 4:1.

73. A method as claimed in claim 72, wherein said amino acid is a compound of formula (II):

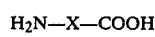

H$_2$N—X—COOH         (II)

wherein X represents a $C_1$–$C_{10}$ alkylene group or a $C_1$–$C_{10}$ alkylene group having at least one substituent selected from the group consisting of hydroxy groups, $C_1$–$C_4$ alkoxy groups, $C_6$–$C_{14}$ aryloxy groups, substituted $C_6$–$C_{14}$ aryloxy groups, $C_7$–$C_9$ aralkyloxy groups, substituted $C_7$–$C_9$ aralkyloxy groups, mercapto groups, $C_1$–$C_4$ alkylthio groups, $C_6$–$C_{14}$ arylthio groups, substituted $C_6C_{14}$ arylthio groups, $C_7$–$C_9$ aralkylthio groups, substituted $C_7$–$C_9$ aralkylthio groups, $C_2$–$C_5$ carboxyalkylthio groups, amino groups, amino groups having one or two substituents selected from the group consisting of
$C_1$–$C_4$ alkyl groups, $C_6$–$C_{14}$ aryl groups, substituted $C_6$–$C_{14}$ aryl groups, $C_7$–$C_9$ aralkyl groups, substituted $C_7$–$C_9$ aralkyl groups and carboxylic acyl groups,
$C_6$–$C_{14}$ aryl groups, substituted $C_6$–$C_{14}$ aryl groups, carboxy groups, amidino groups, sulfo groups, $C_1$–$C_4$ alkylsulfinyl groups, $C_1$–$C_4$ alkylsulfonyl groups and heterocyclic groups having from 5 to 14 ring atoms of which from 1 to 5 are hetero-atoms selected from the group consisting of nitrogen, oxygen and sulfur atoms, said substituted aryloxy, aralkyloxy, arylthio, aralkylthio, aryl and aralkyl groups having at least one substituent selected from the group consisting of $C_1$–$C_4$ alkyl groups, hydroxy groups, amino groups and $C_1$–$C_4$ alkoxy groups, or a pharmaceutically acceptable salt thereof.

74. A method as claimed in claim 73, wherein the N-acyl group is selected from the group consisting of: saturated aliphatic acyl groups having from 1 to 8 carbon atoms; aromatic acyl groups in which the aryl moiety has from 6 to 10 ring carbon atoms and is unsubstituted or has from 1 to 3 substituents independently selected from the group consisting of $C_1$–$C_4$ alkyl groups and $C_1$–$C_4$ alkoxy groups; alicyclic acyl groups in which the cycloalkane ring has from 3 to 6 carbon atoms; araliphatic acyl groups in which the aryl ring has from 6 to 10 ring carbon atoms and the alkyl group has from 1 to 4 carbon atoms, the aryl ring being unsubstituted or having from 1 to 3 substituents independently selected from the group consisting of $C_1$–$C_4$ alkyl groups and $C_1$–$C_4$ alkoxy groups; heterocyclic acyl groups in which the heterocyclic ring is saturated or unsaturated and has 5 or 6 ring atoms of which one is a nitrogen, sulfur or oxygen hetero-atom; alkoxycarbonyl groups having a total of from 2 to 7 carbon atoms; aralkyloxycarbonyl groups in which the aralkyl moiety has from 7 to 9 carbon atoms and the aryl ring is unsubstituted or has from 1 to 3 substituents independently selected from the group consisting of $C_1$–$C_4$ alkyl groups and $C_1$–$C_4$ alkoxy groups; and acyl groups derived from an amino acid by removal of OH from the carboxylic acid group and N-acylation of the amino group with at least one of the above-mentioned acyl groups.

75. A method as claimed in claim 73, wherein the N-acyl group is selected from the group consisting of: aromatic acyl groups in which the aryl ring has from 6 to 10 ring atoms and which is unsubstituted or has a single substituent selected from the group consisting of $C_1$–$C_4$ alkyl groups, $C_1$–$C_4$ alkoxy groups, hydroxy groups and amino groups; alicyclic acyl groups in which the cycloalkane moiety has from 3 to 6 carbon atoms; phenylaliphatic acyl groups in which the phenyl group is unsubstituted or has a single $C_1$–$C_4$ alkyl substituent, and in which the alkyl part has from 1 to 4 carbon atoms; alkoxycarbonyl groups having a total of from 4 to 6 carbon atoms; aralkyloxycarbonyl groups in which the aralkyl part has from 7 to 9 carbon atoms and has 0 to 1 substituent selected from the group consisting of $C_1$–$C_4$ alkyl groups and $C_1$–$C_4$ alkoxy groups; and acyl groups derived from an amino acid by removal of OH from the carboxylic acid group and N-acylation of the amino group with at least one of the above-mentioned acyl groups.

76. A method as claimed in claim 73, wherein the N-acyl group is selected from the group consisting of: acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, napththoyl, toluoyl, benzyloxycarbonyl and 4-methoxybenzyloxycarbonyl groups.

77. A method as claimed in claim 73, wherein X represents a $C_1$–$C_5$ alkylene group which is unsubstituted or has 1 or 2 substituents independently selected from the group consisting of: hydroxy groups; $C_1$–$C_4$ alkoxy groups; mercapto groups; $C_1$–$C_4$ alkylthio groups; amino groups; amino groups having one or two $C_1$–$C_4$ alkyl substituents; amino groups having one or two carboxylic acyl substituents; aryl groups having from 6 to 14 carbon atoms wherein the aryl ring is unsubstituted or has from 1 to 3 substituents selected from the group consisting of $C_1$–$C_4$ alkyl groups, hydroxy groups, amino groups and $C_1$–$C_4$ alkoxy groups; carboxy groups; and heterocyclic groups having from 5 to 9 ring atoms, of which from 1 to 3 are hetero-atoms selected from the group consisting of nitrogen and oxygen hetero-atoms.

78. A method as claimed in claim 72, wherein said amino acid is glycine, β-alanine, 4-aminobutyric acid, 5-aminovaleric acid, 6-aminohexanoic acid, 8-aminooctanoic acid, alanine, 2-aminobutyric acid, norvaline, valine, leucine, isoleucine, norleucine, phenylglycine, phenylalanine, tyrosine, O-methyltyrosine, aspartic acid, glutamic acid, 4-carboxyglutamic acid, 3-methylaspartic acid, 2-aminoadipic acid, 2-aminopimelic acid, 2-aminosuberic acid, 3-hydroxyaspartic acid, 3-hydroxyglutamic acid, 2,3-diaminopropionic acid, 2,4-diaminobutyric acid, ornithine, lysine, 5-hydroxylysine, arginine, $N^\delta,N^\delta$-dimethylornithine, $N^\epsilon$-methyllysine, cysteine, methionine, ethionine, S-carboxymethylcysteine, S-benzylcysteine, methionine S-oxide, ethionine S-oxide, methionine S,S-dioxide, cysteic acid, serine, O-methylserine, threonine, O-methylthreonine, homothreonine, ethoxinine, 3-methoxyvaline, 3-phenylserine, 3-methyl-3-phenylalanine, histidine, tryptophan, 2-methylalanine, 2-methylserine, 2-hydroxyisoleucine, 2-methylmethionine, 2-ethyl-2-phenylglycine, 3-aminobutyric acid, 3-amino-4-methylvaleric acid, 3-amino-3-phenylpropionic acid, 3-amino-2-hydroxypropionic acid or 4-amino-3-hydroxybutyric acid.

79. A method as claimed in claim 72, wherein said amino acid is β-alanine, 4-aminobutyric acid, 5-aminovaleric acid, 6-aminohexanoic acid, alanine, valine, leucine, norleucine, methionine, histidine, ornithine, glycine, phenylalanine or phenylglycine.

80. A method as claimed in claim 72, wherein said amino acid is leucylglycine, glycyl-β-alanine, glycylalanine, valylalanine, leucylalanine, glycylvaline, alanylvaline, leucylvaline, valylleucine, phenylalanylleucine, histidylleucine, glycylphenylalanine, alanylphenylalanine, leucylphenylalanine, glycylmethionine, valylmethionine, glycylhistidine, alanylvalylglycine, glycylalanylvaline, glycylphenylalanylleucine or glycylglycylhistidine.

81. A method as claimed in claim 72, wherein said antibiotic is selected from the group consisting of compounds of formula (I):

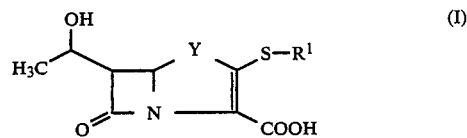

in which:
Y represents a sulfur atom, a methylene group or a methylene group having 1 or 2 substituents selected from the group consisting of methyl and methoxy groups; and
$R^1$ represents a $C_1$–$C_6$ alkyl group, a $C_1$–$C_6$ alkyl group having at least one substituent selected from the group consisting of substituents (i) or a heterocyclic group having from 4 to 14 ring atoms of which from 1 to 5 are hetero-atoms selected from the group consisting of nitrogen, oxygen and sulfur atoms where said heterocyclic group is unsubstituted or has at least one substituent selected from the group consisting of substituents (ii);

substituents (i):
halogen atoms, amino groups, amino groups having at least one substituent selected from the group consisting of substituents (iii), $C_1$–$C_4$ alkylideneamino groups, $C_1$–$C_4$ aminoalkylideneamino groups, amidino groups, amidino groups having from 1 to 3 substituents selected from the group consisting of substituents (iii), heterocyclic groups having from 4 to 14 ring atoms of which from 1 to 5 are hetero-atoms selected from the group consisting of nitrogen, oxygen and sulfur hetero-atoms wherein said heterocyclic group is unsubstituted or has at least one substituent selected from the group consisting of substituents (ii), imino groups, cyano groups, carbamoyl groups and carbamoyl groups having at least one substituent selected from the group consisting of $C_1$–$C_4$ alkyl groups and $C_1$–$C_4$ alkoxy groups;

substituents (ii):
$C_1$–$C_6$ alkanimidoyl groups, $C_1$–$C_6$ alkyl groups, alkoxyalkyl groups where the alkoxy and alkyl parts are each $C_1$–$C_4$, carbamoyl groups, carbamoyl groups having at least one substituent selected from the group consisting of $C_1$–$C_4$ alkyl groups and $C_1$-$C_4$ alkoxy groups, $C_1$-$C_4$ haloalkyl groups, heterocyclic acylimidoyl groups where the heterocyclic part has from 5 to 9 ring atoms of which from 1 to 3 are heteroatoms selected from the group consisting of nitrogen, oxygen and sulfur hetero-atoms, amidino groups, amidino groups having from 1 to 3 substituents selected from the group consisting of substituents (iii), imino groups, oxygen atoms, $C_1$-$C_6$ alkanoyl groups, $C_1$-$C_6$ alkanesulfonyl groups, $C_1$-$C_6$ alkanesulfinyl groups, hydroximino groups, $C_1$-$C_4$ alkoximino groups, carbamoyloxy groups, carbamoyloxy groups having at least one substituent selected from the group consisting of $C_1$-$C_4$ alkyl groups and $C_1$-$C_4$ alkoxy groups, carbamoyloxyalkyl groups where the alkyl part is $C_1$-$C_4$ and the carbamoyl part is unsubstituted or has at least one substituent selected from the group consisting of $C_1$-$C_4$ alkyl groups and $C_1$-$C_4$ alkoxy groups and $C_1$-$C_4$ iminoalkyl groups;

substituents (iii):

$C_1$-$C_6$ alkyl groups, $C_2$-$C_6$ alkenyl groups, $C_2$-$C_6$ alkynyl groups, oxygen atoms and said alkyl, alkenyl and alkynyl groups having at least one substituent selected from the group consisting of halogen atoms, carbamoyloxy groups and carbamoyloxy groups having at least one substituent selected from the group consisting of $C_1$-$C_4$ alkyl groups and $C_1$-$C_4$ alkoxy groups;

and pharmaceutically acceptable salts thereof.

82. A method as claimed in claim 81, wherein Y represents a sulfur atom, a methylene group, or the group $CH_3$—CH<, $CH_3O$—CH< or $(CH_3)_2C<$.

83. A method as claimed in claim 82, wherein $R^1$ represents an ethyl, 2-fluoroethyl, 2-(aminomethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)-$N^1$-methylamidinomethyl, $N^1$-(3-fluoropropyl)-$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidoyl-3-pyrrolidinyl, $N^1,N^1$-diallylamidinomethyl, $N^1$-methyl-$N^1$-(2-propynyl)amidino, $N^1$-(2-fluoroethyl)-$N^1$-methylamidino, $N^1$-(3-fluoropropyl)-$N^1$-methylamidino, $N^1$-methyl-$N^1$-(2,2,2-trifluoroethyl)amidino, $N^1$-allyl-$N^1$-methylamidinomethyl, cyanomethyl, 2-cyanoethyl, 1-cyanoethyl, 2-cyano-1-methylethyl, 2-aminoethyl, 1-carbamoylethyl, 2-(1-aminoethylideneamino)ethyl, 1-amidino-3-pyrrolidinyl, 2-methyl-1,3-diazabicyclo[3.3.0]oct-2-en-7-yl, 2-methoxymethyl-1,3-diazabicyclo[3.3.0]oct-2-en-7-yl, 5-imino-2-pyrrolidinyl, 2-imino-5-piperidinyl, 1-acetimidoyl-5-methylcarbamoyl-3-pyrrolidinyl, 1-acetimidoyl-5-methoxycarbamoyl-3-pyrrolidinyl, 2-imino-2-(S-oxothiomorpholino)ethyl, 2-imino-2-(1,1-dioxo-1,3-thiazolidin-3-yl)ethyl, 2-imino-2-(S,S-dioxothiomorpholino)ethyl, 2-imino-2-(3,5-dioxo-1-piperazinyl)ethyl, 2-imino-2-(4-methyl-3,5-dioxo-1-piperazinyl)ethyl, 2-imino-2-(3-oxo-1-piperazinyl)ethyl, 2-imino-2-(4-methyl-3-oxo-1-piperazinyl)ethyl, 2-imino-2-(4-acetyl-3-oxo-1-piperazinyl)ethyl, 2-imino-2-(4-methanesulfonyl-3-oxo-1-piperazinyl)ethyl, $N^1$-(2-carbamoyloxyethyl)-$N^1$-methylamidinomethyl, 2-(3-hydroximino-1-pyrrolidinyl)-2-iminoethyl, 2-imino-2-(3-methoximino-1-pyrrolidinyl)ethyl, 2-(4-hydroximinopiperidino)-2-iminoethyl, 2-imino-2-(4-methoximinopiperidino)ethyl, 2-(3-carbamoyloxy-1-pyrrolidinyl)-2-iminoethyl, 2-imino-2-(3-oxo-1-piperazinyl)ethyl, 2-(3-carbamoylpiperidino)-2-iminoethyl, 2-(3-carbamoyloxypiperidino)-2-iminoethyl, 2-(2-carbamoyloxy-1-pyrrolidinyl)-2-iminoethyl, 2-(2-carbamoyloxymethyl-1-pyrrolidinyl)-2-iminoethyl, 2-(4-carbamoyloxypiperidino)-2-iminoethyl, 2-(4-formyl-1-piperazinyl)-2-iminoethyl, 2-(4-acetyl-1-piperazinyl)-2-iminoethyl, 1-formyl-3-azetidinyl, 1-iminomethyl-3-azetidinyl, 1-methyl-4-piperidyl, 1-acetimidoyl-4-piperidyl or 1-acetyl-3-pyrrolidinyl group.

84. A method as claimed in claim 82, wherein said N-acylated derivative of an amino acid is selected from the group consisting of N-benzoylvaline and N-benzoyl-β-alanine.

85. A method as claimed in claim 81, wherein said antibiotic is selected from the group consisting of:

(5R,6S)-2-{2-[(aminomethylene)amino]ethylthio}-6-[1(R)-hydroxyethyl]-2-carbapenem-3-carboxylic acid (5R,6S)-2-[(3S)-1-acetimidoylpyrrolidin-3-ylthio]-6-[1(R)-hydroxyethyl]-2-carbapenem-3-carboxylic acid (5R,6S)-2-[(3R)-1-acetimidoylpyrrolidin-3-ylthio]-6-[1(R)-hydroxyethyl]-2-carbapenem-3-carboxylic acid (5R,6S)-2-[(3R)-1-acetimidoylpyrrolidin-3-ylthio]-6-[1(R)-hydroxyethyl]-1(S)-methyl-2-carbapenem-3-carboxylic acid (5R,6S)-2-[(3S)1-acetimidoylpyrrolidin-3-ylthio]-6-[1(R)-hydroxyethyl]-1(R)-methyl-2-carbapenem-3-carboxylic acid (5R,6S)-2[(3S)-1-acetimidoylpyrrolidin-3-ylthio]-6-[1(R)-hydroxyethyl]-1(S)-methyl-2-carbapenem-3-carboxylic acid and (5R,6S)-2-[(3S)-1-acetimidoyl-5(S)-carbamoylpyrrolidin-3-ylthio]-6-[1(R)-hydroxyethyl]-2-carbapenem-3-carboxylic acid and said N-acylated amino acid is selected from the group consisting of:

N-(p-toluoyl)-β-alanine
N-(4-methoxybenzoyl)-β-alanine
N-(3-hydroxy-2-naphthoyl)-β-alanine
N-benzoylglycyl-β-alanine
N-benzoyl-β-alanine
N-benzoyl-5-aminovaleric acid  N-benzoyl-6-aminohexanoic acid
N-cyclohexanecarbonyl-6-aminohexanoic acid
N-(N-methylnicotinoyl)-6-aminohexanoic acid
N-benzoyl-8-aminooctanoic acid
N-benzoylalanine
N-(1-naphthoyl)alanine
N-benzoylvalylalanine
N-benzoyl-2-aminobutyric acid N-benzoylnorvaline
N-valerylvaline
N-benzoylalanylvaline
N-benzoylvaline
N-benzoylleucine
N-benzoylglycylphenylalanylleucine
N-benzoylnorleucine
$N^\alpha,N^\delta$-dibenzoylornithine
$N^\alpha,N^\delta$-dicyclopropanecarbonylornithine
$N^\alpha,N^\delta$-dicyclohexanecarbonylornithine
$N^\alpha$-benzoyl-$N^\delta$-cyclohexanecarbonylornithine
$N^\alpha$-benzoyl-$N^\delta$-acetylornithine
$N^\alpha$-cyclohexanecarbonyl-$N^\delta$-acetylornithine
$N^\alpha,N^\epsilon$-dibenzoyllysine
$N^\alpha,N^\epsilon$-dicyclopropanecarbonyllysine
$N^\alpha,N^\epsilon$-dicyclohexanecarbonyllysine
$N^\alpha$-benzoyl-$N^\epsilon$-cyclohexanecarbonyllysine
$N^\alpha$-benzoyl-$N^\epsilon$-acetyllysine
$N^\alpha,N^\epsilon$-dianisoyllysine
$N^\alpha$-cyclohexanecarbonyl-$N^\epsilon$-acetyllysine
N-benzoylphenylalanine
N-(4-methoxybenzoyl)phenylalanine
N-hexanoylphenylalanine
N-cyclopropanecarbonylphenylalanine
N-cyclohexanecarbonylphenylalanine
N-anisoylphenylalanine
N-benzoylglycylphenylalanine
N-benzoylalanylphenylalanine
N-cyclohexanecarbonylleucylphenylalanine
N-benzoylphenylglycine
N-cyclopropanecarbonylphenylglycine
N-cyclohexanecarbonylphenylglycine
N-anisoylphenylglycine
N-(4-methoxybenzoyl)phenylglycine
N-benzoyl-O-methyltyrosine
N-benzoylmethionine
N-phenylacetylmethionine
N-benzoylvalylmethionine
N-benzoylethionine
N-(4-methoxybenzyloxycarbonyl)ethionine
N-benzoylthreonine
N-benzoylhistidine
N-(p-toluoyl)histidine
N-(4-methoxybenzoyl)histidine
N-(4-methoxybenzoyl)-3-aminobutyric acid and
N-butyryl-3-amino-3-phenylpropionic acid.

86. A method as claimed in claim 81, wherein said N-acylated derivative of an amino acid is selected from the group consisting of N-benzoylvaline and N-benzoyl-β-alanine.

87. A method as claimed in claim 86, wherein said antibiotic and said N-acylated derivative of an amino acid are administered together.

88. A method as claimed in claim 86, wherein said antibiotic and said N-acylated derivative of an amino acid are administered sequentially within 1 hour of each other.

89.
The method as claimed in claim 86, wherein said antibiotic and said N-acylated derivatives of an amino acid are administered concurrently.

90. A method as claimed in claim 72, wherein said N-acylated derivative of an amino acid is selected from the group consisting of N-benzoylvaline and N-benzoyl-β-alanine.

91. A method as claimed in claim 69, wherein said antibiotic and said N-acylated derivative of an amino acid are administered together.

92. The method as claimed in claim 91, wherein the weight ratio of said N-acylated amino acid to said antibiotic is from about 0.1:1 to 4:1.

93. A method as claimed in claim 69, wherein said antibiotic and said N-acylated derivative of an amino acid are administered sequentially within 1 hour of each other.

94. The method as claimed in claim 93, wherein the weight ratio of said N-acylated amino acid to said antibiotic is from about 0.1:1 to 4:1.

95. A method of treating a mammal suffering from a bacterial infection by administering to said mammal:
(a) an antibiotic in an amount effective to treat said bacterial infection, said antibiotic selected from the group consisting of penem antibiotics and carbapenem antibiotics having renal toxicity; and
(b) an amount of pharmaceutically acceptable N-acylated derivative of an amino acid selected from the group consisting of ornithine, lysine, phenylglycine and phenylalanine at least sufficient to reduce or eliminate said renal toxicity;
said antibiotic and said amino acid derivative being administered sequentially within one hour of each other.

96. A method as claimed in claim 95, wherein the weight ratio of said N-acylated amino acid to said antibiotic is from about 0.1:1 to 4:1.

97. A method as claimed in claim 96, wherein said N-acylated amino acid is a compound of formula (IV):

$$R^4-NH-(CH_2)_n-CH(COOH)-NHR^3 \qquad (IV)$$

wherein:
n is 3 or 4; and
$R^3$ and $R^4$ are independently selected from the group consisting of hydrogen atoms and carboxylic acyl groups, provided that $R^3$ and $R^4$ are not both hydrogen; or a pharmaceutically acceptable salt thereof.

98. A method as claimed in claim 97, wherein $R^3$ and $R^4$ are independently selected from the group consisting of: hydrogen atoms; $C_1-C_{18}$ alkanoyl groups; $C_3-C_8$ alkenoyl groups; $C_3-C_8$ alkynoyl groups; aromatic acyl groups wherein the aryl part is $C_6-C_{14}$ carbocyclic aryl and is unsubstituted or has from 1 to 5 substituents selected from the group consisting of $C_1-C_4$ alkyl groups, hydroxy groups, $C_1-C_4$ alkoxy groups, amino groups and sulfo groups; cycloalkanecarbonyl group where the cycloalkane part is $C_3-C_8$; $C_2-C_7$ alkoxycarbonyl groups; and aralkyloxycarbonyl groups where the aralkyl part has from 7 to 9 carbon atoms and is unsubstituted or has from 1 to 5 substituents selected from the group consisting of amino groups; $C_1-C_4$ alkyl groups, $C_1-C_4$ alkoxy groups and hydroxyl groups; provided that $R^3$ and $R^4$ are not both hydrogen.

99. A method as claimed in claim 97, wherein $R^3$ and $R^4$ are independently selected from the group consisting of hydrogen atoms and acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, naphthoyl, toluoyl, benzyloxycarbonyl and 4-methoxybenzyloxycarbonyl groups, provided that $R^3$ and $R^4$ are not both hydrogen atoms.

100. A method as claimed in claim 97, wherein at least one of $R^3$ and $R^4$ represents an acyl group selected from the group consisting of acetyl and benzoyl groups.

101. A method as claimed in claim 96, wherein said N-acylated amino acid is a compound of formula (V):

$$Ph-(CH_2)_m-CH(COOH)-NHR^2 \qquad (V)$$

wherein:
Ph represents a phenyl group;
m is 0 or 1; and
$R^2$ represents a carboxylic acyl groups; or a pharmaceutically acceptable salt thereof.

102. A method as claimed in claim 101, wherein $R^2$ is selected from the group consisting of: $C_1$–$C_{18}$ alkanoyl groups; $C_3$–$C_8$ alkenoyl groups; $C_3$–$C_8$ alkynoyl groups; aromatic acyl groups wherein the aryl part is $C_6$–$C_{14}$ carbocyclic aryl and is unsubstituted or has from 1 to 5 substituents selected from the group consisting of $C_1$–$C_4$ alkyl groups, hydroxy groups, $C_1$–$C_4$ alkoxy groups, amino groups and sulfo groups; cycloalkanecarbonyl groups where the cycloalkane part is $C_3$–$C_8$; $C_2$–$C_7$ alkoxycarbonyl groups; and aralkyloxycarbonyl groups where the aralkyl part has from 7 to 9 carbon atoms and is unsubstituted or has from 1 to 5 substituents selected from the group consisting of amino groups, $C_1$–$C_4$ alkyl groups, $C_1$–$C_4$ alkoxy groups and hydroxy groups.

103. A method as claimed in claim 101, wherein $R^2$ is selected from the group consisting of acetyl, benzoyl, cyclohexanecarbonyl, cyclopropanecarbonyl, hexanoyl, isobutyryl, crotonoyl, ethoxycarbonyl, 4-hydroxybenzoyl, anisoyl, 4-aminobenzoyl, naphthoyl, toluoyl, benzyloxycarbonyl and 4-methoxybenzyloxycarbonyl groups.

104. A method as claimed in claim 101, wherein $R^2$ represents an acyl group selected from the group consisting of acetyl and benzoyl groups.

105. A method as claimed in claim 96, wherein said N-acylated amino acid is selected from the group consisting of:
$N^\alpha,N^\delta$-Dibenzoylornithine
$N^\alpha,N^\delta$-Dicyclohexanecarbonylornithine
$N^\alpha$-Benzoyl-$N^\delta$-cyclohexanecarbonylornithine
$N^\alpha$-Benzoyl-$N^\delta$-acetylornithine
$N^\alpha,N^\epsilon$-Dibenzoyllysine
$N^\alpha,N^\epsilon$-Dicyclohexanecarbonyllysine
$N^\alpha$-Benzoyl-$N^\epsilon$-cyclohexanecarbonyllysine
$N^\alpha$-Benzoyl-$N^\epsilon$-acetyllysine
N-Benzoylphenylglycine
N-Benzoylphenylalanine
N-Cyclohexanecarbonylphenylglycine
N-Cyclohexanecarbonylphenylalanine
$N^\alpha$-Cyclohexanecarbonyl-$N^\epsilon$-acetyllysine and
$N^\alpha$-Cyclohexanecarbonyl-$N^\delta$-acetylornithine.

106. A method as claimed in claim 96, wherein said antibiotic is a compound of formula (I):

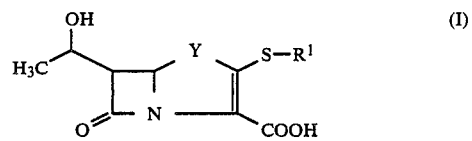

wherein:
Y represents a sulfur atom, a methylene group, or a methylene group having 1 or 2 methyl substituents; and
$R^1$ represents an ethyl, 2-fluoroethyl, 2-(aminomethyleneamino)ethyl, $N^1,N^1$-dimethylamidinomethyl, $N^1,N^1,N^2$-trimethylamidinomethyl, 3-pyrrolidinyl, 1-formimidoyl-3-pyrrolidinyl, 1-acetimidoyl-3-pyrrolidinyl, 1-propionimidoyl-3-pyrrolidinyl, 2-methyl-1,4,5,6-tetrahydro-5-pyrimidinyl, 2-methoxymethyl-1,4,5,6-tetrahydro-5-pyrimidinyl, 3-azetidinyl, 1-acetimidoyl-3-azetidinyl, $N^1$-methyl-$N^1$-(2-propynyl)amidinomethyl, $N^1$-(2-fluoroethyl)-$N^1$-methylamidinomethyl, $N^1$-(3-fluoropropyl)-$N^1$-methylamidinomethyl, $N^1$-methyl-$N^1$-(2,2,2-trifluoroethyl)amidinomethyl, 1-(3-azetidinyl)ethyl, 1-(1-acetimidoyl-3-azetidinyl)ethyl, 1,4,5,6-tetrahydro-2-pyrimidinylmethyl, 1-(4,5-dihydro-2-thiazolyl)ethyl, 5-carbamoyl-3-pyrrolidinyl, 1-acetimidoyl-5-carbamoyl-3-pyrrolidinyl, 2-chloromethyl-1,4,5,6-tetrahydro-5-pyrimidinyl, 1-butyrimidoyl-3-pyrrolidinyl, 1-nicotinimidoyl-3-pyrrolidinyl, $N^1,N^1$-diallyl-amidinomethyl, $N^1$-methyl-$N^1$-(2-propynyl)amidino, $N^1$-(2-fluoroethyl)-$N^1$-methylamidino, $N^1$-(3-fluoro-propyl)-$N^1$-methylamidino, $N^1$-methyl-$N^1$-(2,2,2-trifluoroethyl)amidino, $N^1$-allyl-$N^1$-methylamidinomethyl, cyanomethyl, 2-cyanoethyl, 1-cyanoethyl, 2-cyano-1-methylethyl, 2-aminoethyl or 1-carbamoylethyl group
and pharmaceutically acceptable salts thereof.

107. A method as claimed in claim 106, wherein said antibiotic is selected from the group consisting of:
(5R,6S)-2-{2-[(aminomethylene)amino]ethylthio}-6-[1(R)-hydroxyethyl]-2-carbapenem-3-carboxylic acid
(5R,6S)-2-[(3S)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-2-carbapenem-3-carboxylic acid
(5R,6S)-2-[(3R)-1-acetimidoylpyrrolidin-3-ylthio]-6-[1(R)-hydroxyethyl]-1(S)-methyl-2-carbapenem-3-carboxylic acid
(5R,6S)-2-[(3S)-1-acetimidoylpyrrolidin-3-ylthio]-6-[1(R)-hydroxyethyl]-1(R)-methyl-2-carbapenem-3-carboxylic acid
(5R,6S)-2-[(3S)-1-acetimidoylpyrrolidin-3-ylthio]-6-[1(R)-hydroxyethyl]-1(S)-methyl-2-carbapenem-3-carboxylic acid and
(5R,6S)-2-[(3S)-1-acetimidoyl-5(S)-carbamoylpyrrolidin-3-ylthio]-6-[1(R)-hydroxyethyl]-2-carbapenem-3-carboxylic acid.

108. A method as claimed in claim 96, wherein said antibiotic and said N-acylated derivative of an amino acid are administered together.

109. A method as claimed in claim 96, wherein said antibiotic and said N-acylated derivative of an amino acid are administered sequentially within 1 hour of each other.

110. The method of treating a mammal suffering from a bacterial infection by administering to said mammal:
   (a) (5R,6S)-2-[(3S)-1-acetimidoylpyrrolidin-3-ylthio]-6-[1(R)-hydroxyethyl]-2-carbapenem-3-carboxylic acid in an amount effective to treat said bacterial infection; and
   (b) N-benzoyl-β-alanine in an amount sufficient to reduce or eliminate renal toxicity of said carbapenem; and
   said carbapenem and said alanine being administered to said mammal sufficiently closely in time to each other that concentration in the blood while said antibiotic is in the blood, is sufficient to reduce or eliminate said renal toxicity.

111. The method as claimed in claim 110, wherein the weight ratio of (a) to (b) is from about 1:0.1 to 1:4.

112. The method as claimed in claim 111, wherein said weight ratio is about 1:1.

113. The method as claimed in claim 111, wherein (a) and (b) are administered together.

114. The method as claimed in claim 110, wherein (a) and (b) are administered concurrently.

115. The method as claimed in claim 110, wherein (a) and (b) are administered sequentially within one hour of each other.

116. The method as claimed in claim 110, wherein (a) and (b) are administered together.

* * * * *

UNITED STATES PATENT AND TRADEMARK OFFICE
CERTIFICATE OF CORRECTION

PATENT NO. : 4,757,066

DATED : July 12, 1988

INVENTOR(S) : SHIOKARI et al

It is certified that error appears in the above-identified patent and that said Letters Patent is hereby corrected as shown below:

Title page, under Section [56] References Cited, insert the following:

U.S. PATENT DOCUMENTS -

4,616,038  10/1986  F. Kahan et al  514/563

FOREIGN PATENT DOCUMENTS -

48301  3/1982  European 91594  10/1983  European

Column 36, line 36: change "carba penem" to --carbapenem--.

Column 37, line 41: under the first occurrence of the heading of "Amount mg/kg" of the Table, change "50" to --150--.

Column 46, line 28 (Claim 15): change "$N^{60}$" to --$N^a$--.

Column 48, line 16 (Claim 17): change "$CH_{13}$" to --$CH_3$--.

Signed and Sealed this

Fifth Day of January, 1993

Attest:

DOUGLAS B. COMER

Attesting Officer

Acting Commissioner of Patents and Trademarks